US 11,578,073 B2

(12) United States Patent
Pathak et al.

(10) Patent No.: US 11,578,073 B2
(45) Date of Patent: Feb. 14, 2023

(54) XANTHINE ANALOGS AS POTENT ANTI-WEST NILE VIRAL AGENTS

(71) Applicants: Southern Research Institute, Birmingham, AL (US); Oregon Health and Science University, Portland, OR (US)

(72) Inventors: Ashish Kumar Pathak, Birmingham, AL (US); Theresa Ha Nguyen, Birmingham, AL (US); Corinne E. Augelli-Szafran, Homewood, AL (US); Alec Jay Hirsch, Portland, OR (US); Jessica Lee Smith, Beaverton, OR (US)

(73) Assignees: Southern Research Institute, Birmingham, AL (US); Oregon Health and Science University, Portland, OR (US)

( * ) Notice: Subject to any disclaimer, the term of this patent is extended or adjusted under 35 U.S.C. 154(b) by 0 days.

(21) Appl. No.: 16/905,857

(22) Filed: Jun. 18, 2020

(65) Prior Publication Data
US 2020/0399271 A1    Dec. 24, 2020

Related U.S. Application Data

(60) Provisional application No. 62/864,277, filed on Jun. 20, 2019.

(51) Int. Cl.
C07D 473/08    (2006.01)
A61P 31/14    (2006.01)

(52) U.S. Cl.
CPC ............ *C07D 473/08* (2013.01); *A61P 31/14* (2018.01)

(58) Field of Classification Search
CPC .......................... C07D 473/06; C07D 473/08
See application file for complete search history.

(56) References Cited

U.S. PATENT DOCUMENTS

2006/0094733 A1* 5/2006 Boggs .................. C07D 473/06
514/263.2

FOREIGN PATENT DOCUMENTS

WO    WO 2005-037779 A2    4/2005

OTHER PUBLICATIONS

U.S. Appl. No. 62/864,277, filed Jun. 20, 2019, Ashish Kumar Pathak, et al.

* cited by examiner

*Primary Examiner* — Susanna Moore
(74) *Attorney, Agent, or Firm* — Ballard Spahr LLP

(57) ABSTRACT

The present disclosure is concerned with xanthine analogs, methods of making xanthine analogs, and methods of treating West Nile virus using these analogs. This abstract is intended as a scanning tool for purposes of searching in the particular art and is not intended to be limiting of the present invention.

2 Claims, No Drawings

XANTHINE ANALOGS AS POTENT ANTI-WEST NILE VIRAL AGENTS

CROSS-REFERENCE TO RELATED APPLICATIONS

This application claims the benefit of U.S. Provisional Application No. 62/864,277, filed on Jun. 20, 2019, the contents of which are hereby incorporated by reference in their entirety.

STATEMENT REGARDING FEDERALLY SPONSORED RESEARCH

This invention was made with government support under grant number 1U19AI109680-01 awarded by the National Institute of Allergy and Infectious Diseases and the National Institutes of Health. The government has certain rights in the invention.

BACKGROUND

West Nile virus (WNV) is the leading cause of mosquito-borne illness in the continental United States. It is most commonly spread to people by the bite of a mosquito. Most human infections are mild, causing fever, headache, and body aches, often accompanied by a skin rash and swollen lymph glands. If the virus crosses the blood-brain barrier, however, it can cause life-threatening conditions that include inflammation of the brain and spinal cord. Despite the severe implications of this disease, there is currently no vaccine or antiviral treatment available for WNV. Thus, there remains a need for antiviral agents useful for the treatment and/or prevention of WNV.

SUMMARY

In accordance with the purpose(s) of the invention, as embodied and broadly described herein, the invention, in one aspect, relates to xanthine compounds useful in the treatment of West Nile virus.

Disclosed are compounds having a structure represented by a formula:

wherein n is selected from 0, 1, and 2; wherein each occurrence of A, when present, is individually selected from —C(O)— and —CH$_2$—, provided that no more than one occurrence of A, when present, is —C(O)—; wherein Z is selected from N and CR$^{10}$; wherein R$^{10}$, when present, is selected from hydrogen and C1-C4 alkyl; wherein R$^1$ is selected from hydrogen, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^2$ is selected from —OH, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^3$ is selected from C1-C4 alkyl and Ar$^1$, provided that when R$^3$ is methyl then R$^{10}$ is not hydrogen and provided that when Z is N then R$^3$ is Cy$^2$; wherein Ar$^1$, when present, is selected from 6-membered aryl and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl); and wherein each of R$^{4a}$, R$^{4b}$, R$^{4c}$, and R$^{4d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, —CO$_2$H, and —CO$_2$(C1-C4 alkyl); wherein Cy$^1$ is selected from cyclohexyl, 6-membered aryl, and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl), provided that when n is 1, A is CH$_2$, R$^1$ is hydrogen or methyl, R$^2$ is methyl, R$^3$ is 6-membered aryl, and Cy$^1$ is 6-membered aryl, then R$^1$, when present, is C1-C4 alkyl, and provided that when each occurrence of A, when present, is CH$_2$, R$^1$ is hydrogen, R$^2$ is methyl, R$^3$ is 6-membered aryl, and Cy$^1$ is 6-membered aryl, then Z is CR$^{10}$, or a pharmaceutically acceptable salt thereof.

Also disclosed are compounds selected from:

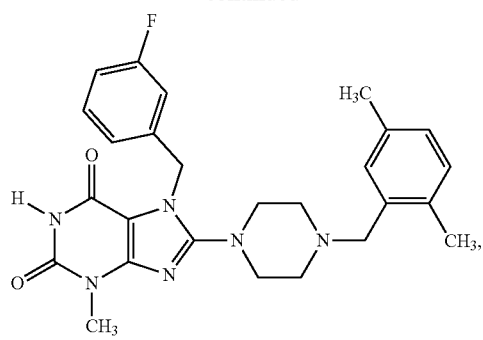

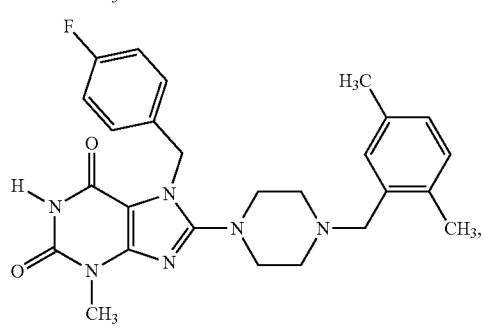

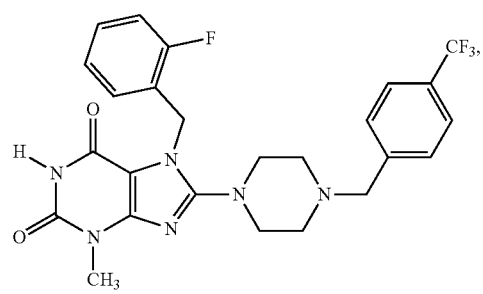

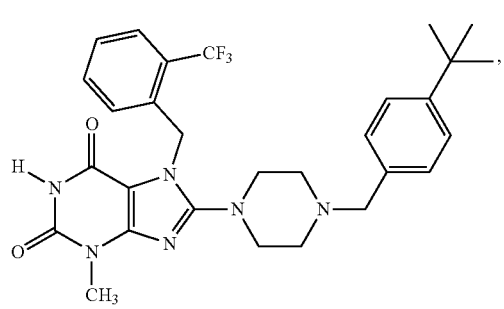

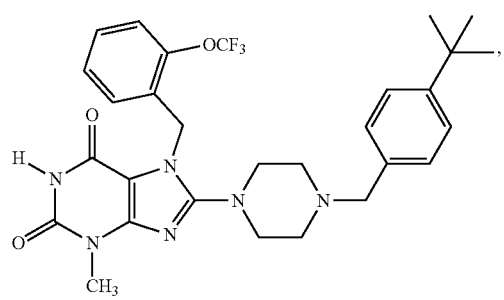

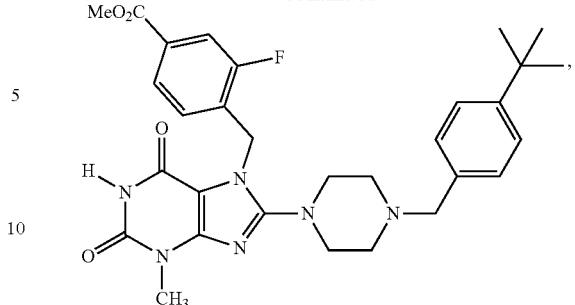

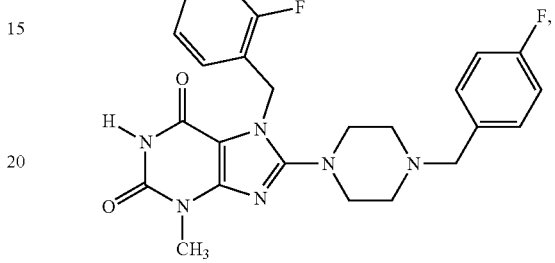

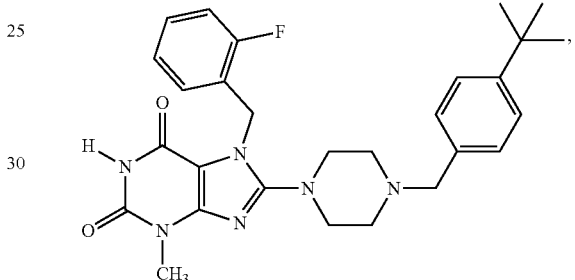

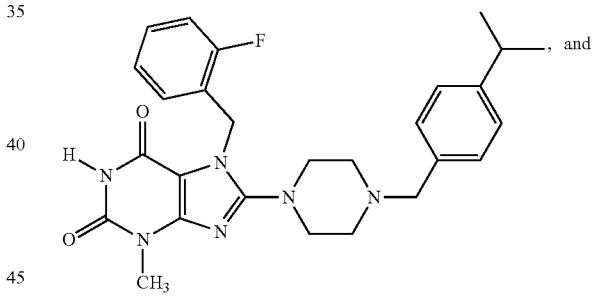

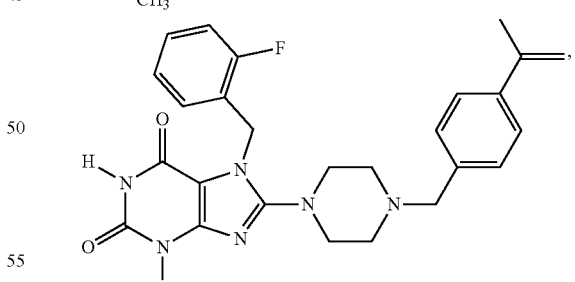

, and

or a pharmaceutically acceptable salt thereof.

Also disclosed are pharmaceutical compositions comprising a therapeutically effective amount of a disclosed compound and a pharmaceutically acceptable carrier.

Also disclosed are methods for treating West Nile virus (WNV) in a subject, the method comprising administering to the subject an effective amount of at least one compound having a structure represented by a formula:

wherein n is selected from 0, 1, and 2; wherein each occurrence of A, when present, is individually selected from —C(O)— and —CH$_2$—, provided that no more than one occurrence of A, when present, is —C(O)—; wherein Z is selected from N and CR$^{10}$; wherein R$^{10}$, when present, is selected from hydrogen and C1-C4 alkyl; wherein R$^1$ is selected from hydrogen, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^2$ is selected from —OH, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^3$ is selected from C1-C4 alkyl and Ar$^1$; wherein Ar$^1$, when present, is selected from 6-membered aryl and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl); and wherein each of R$^{4a}$, R$^{4b}$, R$^{4c}$, and R$^{4d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, —CO$_2$H, and —CO$_2$(C1-C4 alkyl); wherein Cy$^1$ is selected from cyclohexyl, 6-membered aryl, and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl), provided that when n is 1, A is CH$_2$, R$^1$ is hydrogen or methyl, R$^2$ is methyl, R$^3$ is 6-membered aryl, and Cy$^1$ is 6-membered aryl, then R$^1$, when present, is C1-C4 alkyl, or a pharmaceutically acceptable salt thereof, thereby treating West Nile virus.

Also disclosed are kits comprising a compound having a structure represented by a formula:

wherein n is selected from 0, 1, and 2; wherein each occurrence of A, when present, is individually selected from —C(O)— and —CH$_2$—, provided that no more than one occurrence of A, when present, is —C(O)—; wherein Z is selected from N and CR$^{10}$; wherein R$^{10}$, when present, is selected from hydrogen and C1-C4 alkyl; wherein R$^1$ is selected from hydrogen, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^2$ is selected from —OH, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^3$ is selected from C1-C4 alkyl and Ar$^1$; wherein Ar$^1$, when present, is selected from 6-membered aryl and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl); and wherein each of R$^{4a}$, R$^{4b}$, R$^{4c}$, and R$^{4d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, —CO$_2$H, and —CO$_2$(C1-C4 alkyl); wherein Cy$^1$ is selected from cyclohexyl, 6-membered aryl, and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl), provided that when n is 1, A is CH$_2$, R$^1$ is hydrogen or methyl, R$^2$ is methyl, R$^3$ is 6-membered aryl, and Cy$^1$ is 6-membered aryl, then R$^1$, when present, is C1-C4 alkyl, and provided that when n is 0, R$^1$ is hydrogen, R$^2$ is methyl, R$^3$ is 6-membered aryl, and Cy$^1$ is 6-membered aryl, then Z is CR$^{10}$, or a pharmaceutically acceptable salt thereof, and one or more of: (a) at least one antiviral agent; (b) instructions for administering the compound in connection with treating West Nile virus; (c) instructions for administering the compound in connection with reducing the risk of viral infection; and (d) instructions for treating West Nile virus.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

Listed below are definitions of various terms used to describe this invention. These definitions apply to the terms as they are used throughout this specification, unless otherwise limited in specific instances, either individually or as part of a larger group.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component x and 5 parts by weight component Y, x and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a viral infection. The term "patient" includes human and veterinary subjects. In some aspects of the disclosed methods, the subject has been diagnosed with a need for treatment of one or more viral infections prior to the administering step. In various aspects, the viral infection is West Nile virus.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a viral infection such as, for example, West Nile virus, prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{90}$," is intended to refer to the concentration of a substance (e.g., a compound or a drug) that is required for 90% inhibition of a biological process, or component of a process, including a protein, subunit, organelle, ribonucleoprotein, etc. In one aspect, an $EC_{90}$ can refer to the concentration of a substance that is required for 90% inhibition in vivo, as further defined elsewhere herein.

The term "comprising" (and its grammatical variations) as used herein is used in the inclusive sense of "having" or "including" and not in the exclusive sense of "consisting of."

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and include the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric acid, and the like. Salts derived from organic acids, such as aliphatic mono- and dicarboxylic acids, phenyl substituted alkanoic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

It is understood that the compounds of the present disclosure relate to all optical isomers and stereo-isomers at the various possible atoms of the molecule, unless specified otherwise. Compounds may be separated or prepared as their pure enantiomers or diasteriomers by crystallization, chromatography or synthesis.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula ($A^1$O-$A^2$O)$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where A and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula $—N_3$.

The term "nitro" as used herein is represented by the formula $—NO_2$.

The term "nitrile" as used herein is represented by the formula —CN.

The term "silyl" as used herein is represented by the formula $—SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $—S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; —CH=CHPh, which may be substituted with $R^\circ$; $—(CH_2)_{0-4}O(CH_2)_{0-1}$-pyridyl which may be substituted with $R^\circ$; $—NO_2$; —CN; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched alkylene)$O—N(R^\circ)_2$; or $—(C_{1-4}$ straight or branched alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, -(halo$R^\bullet$), $—(CH_2)_{0-2}OH$, $—(CH_2)_{0-2}OR^\bullet$, $—(CH_2)_{0-2}CH(OR^\bullet)_2$; $—O(haloR^\bullet)$, —CN, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^◊$, —NR$^◊$$_2$, —C(O)R$^◊$, —C(O)OR$^◊$, —C(O)C(O)R$^◊$, —C(O)CH$_2$C(O)R$^◊$, —S(O)$_2$R$^◊$, —S(O)$_2$NR$^◊$$_2$, —C(S)NR$^◊$$_2$, —C(NH)NR$^◊$$_2$, or —N(R$^◊$)S(O)$_2$R$^◊$; wherein each R$^◊$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^◊$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

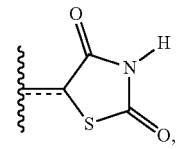

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. "Solvates" refers to the compound formed by the interaction of a solvent and a solute and includes hydrates. Solvates are usually crystalline solid adducts containing solvent molecules within the crystal structure, in either stoichiometric or nonstoichiometric proportions. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules, which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids, which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

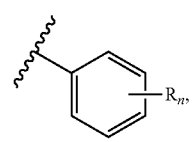

which is understood to be equivalent to a formula:

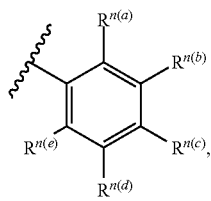

wherein n is typically an integer. That is, $R^n$ is understood to represent five independent substituents, $R^{n(a)}$, $R^{n(b)}$, $R^{n(c)}$, $R^{n(d)}$, $R^{n(e)}$. In each such case, each of the five $R^n$ can be hydrogen or a recited substituent. By "independent substituents," it is meant that each R substituent can be independently defined. For example, if in one instance $R^{n(a)}$ is halogen, then $R^{n(b)}$ is not necessarily halogen in that instance.

In some yet further aspects, a structure of a compound can be represented by a formula:

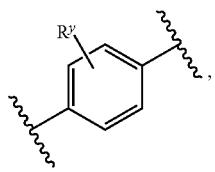

wherein $R^y$ represents, for example, 0-2 independent substituents selected from $A^1$, $A^2$, and $A^3$, which is understood to be equivalent to the groups of formulae:

wherein $R^y$ represents 0 independent substituents

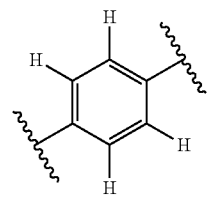

wherein $R^y$ represents 1 independent substituent

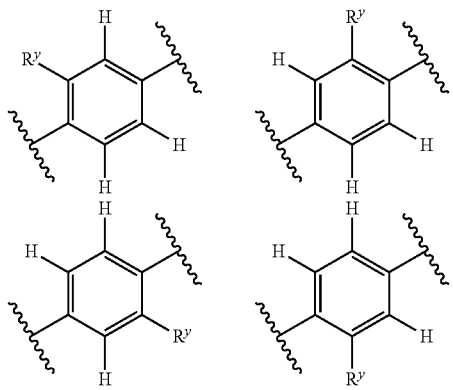

wherein $R^y$ represents 2 independent substituents

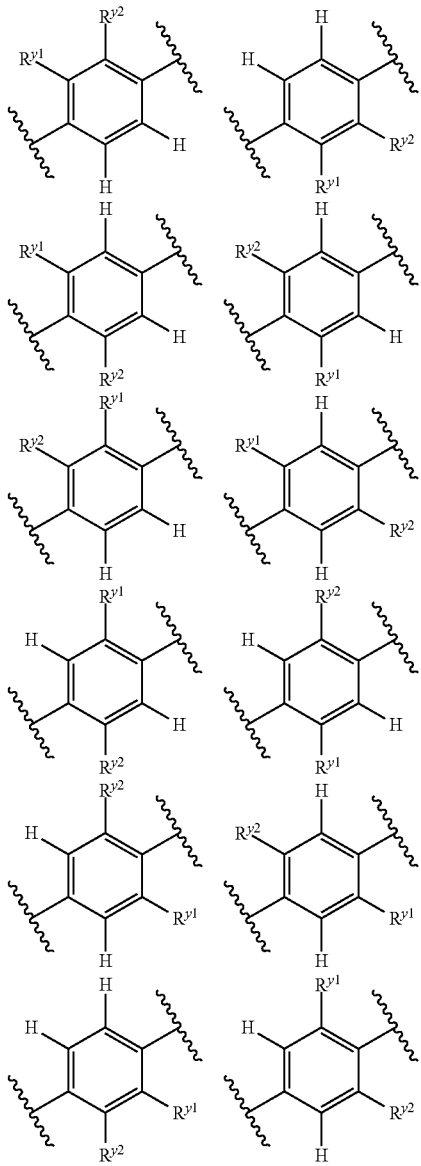

Again, by "independent substituents," it is meant that each R substituent can be independently defined. For example, if in one instance $R^{y1}$ is $A^1$, then $R^{y2}$ is not necessarily $A^1$ in that instance.

In some further aspects, a structure of a compound can be represented by a formula,

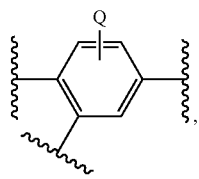

wherein, for example, Q comprises three substituents independently selected from hydrogen and A, which is understood to be equivalent to a formula:

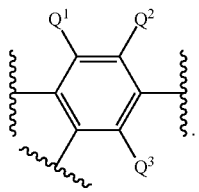

Again, by "independent substituents," it is meant that each Q substituent is independently defined as hydrogen or A, which is understood to be equivalent to the groups of formulae:

wherein Q comprises three substituents independently selected from H and A

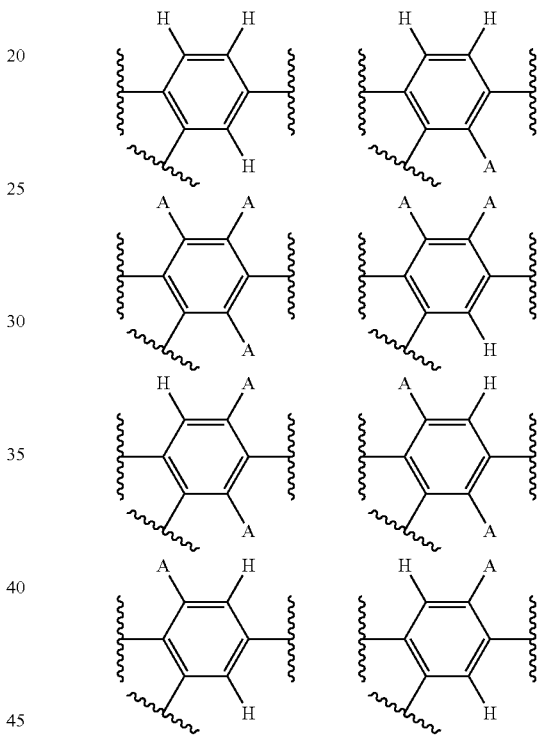

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in treating West Nile virus.

In one aspect, the compounds are useful in treating West Nile virus in a mammal. In a further aspect, the compounds are useful in treating West Nile virus in a human.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

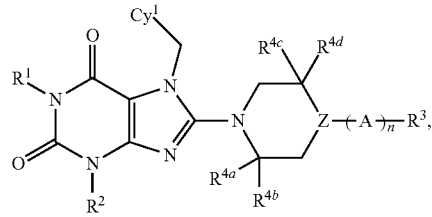

wherein n is selected from 0, 1, and 2; wherein each occurrence of A, when present, is individually selected from —C(O)— and —CH$_2$—, provided that no more than one occurrence of A, when present, is —C(O)—; wherein Z is selected from N and CR$^{10}$; wherein R$^{10}$, when present, is selected from hydrogen and C1-C4 alkyl; wherein R$^1$ is selected from hydrogen, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^2$ is selected from —OH, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^3$ is selected from C1-C4 alkyl and Ar$^1$, provided that when R$^3$ is methyl then R$^{10}$ is not hydrogen and provided that when Z is N then R$^3$ is Cy$^2$; wherein Ar$^1$, when present, is selected from 6-membered aryl and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl); and wherein each of R$^{4a}$, R$^{4b}$, R$^{4c}$, and R$^{4d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, —CO$_2$H, and —CO$_2$(C1-C4 alkyl); wherein Cy$^1$ is selected from cyclohexyl, 6-membered aryl, and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl), provided that when n is 1, A is CH$_2$, R$^1$ is hydrogen or methyl, R$^2$ is methyl, R$^3$ is 6-membered aryl, and Cy$^1$ is 6-membered aryl, then R$^1$, when present, is C1-C4 alkyl, and provided that when each occurrence of A, when present, is CH$_2$, R$^1$ is hydrogen, R$^2$ is methyl, R$^3$ is 6-membered aryl, and Cy$^1$ is 6-membered aryl, then Z is CR$^{10}$, or a pharmaceutically acceptable salt thereof.

In one aspect, disclosed are compounds selected from:

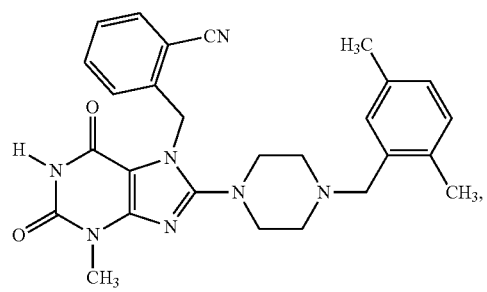

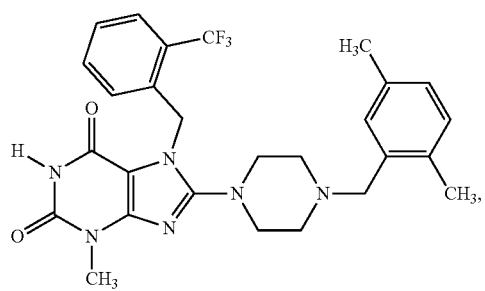
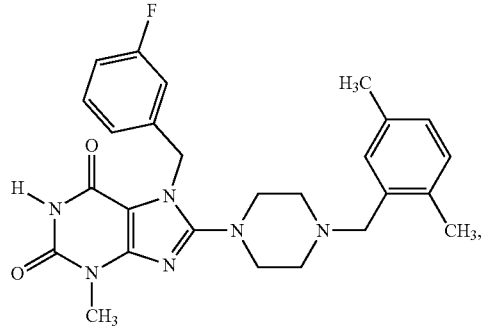
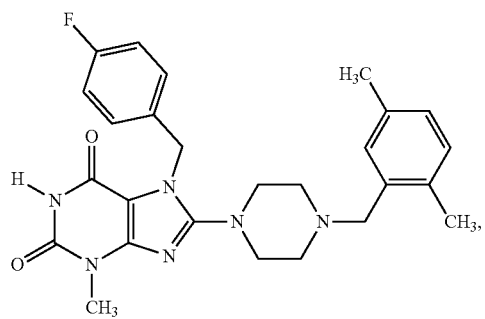
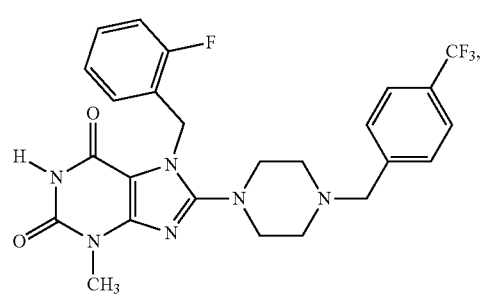
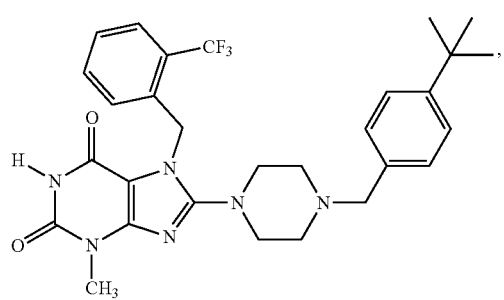
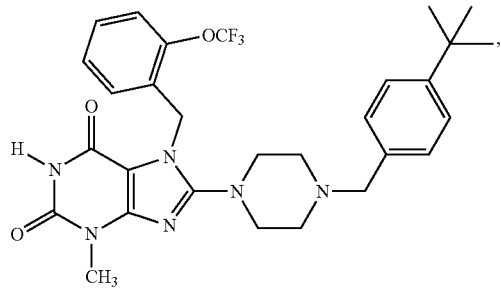
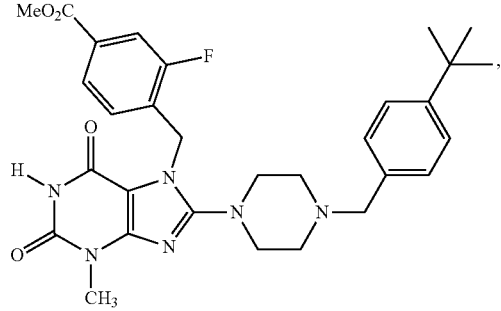
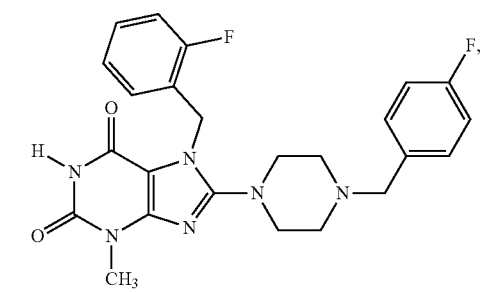
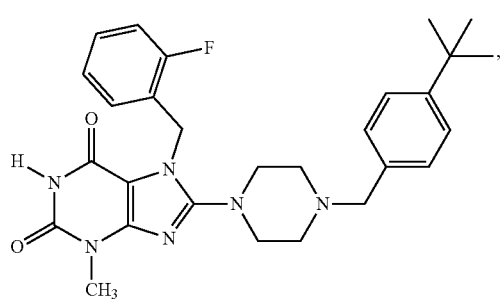
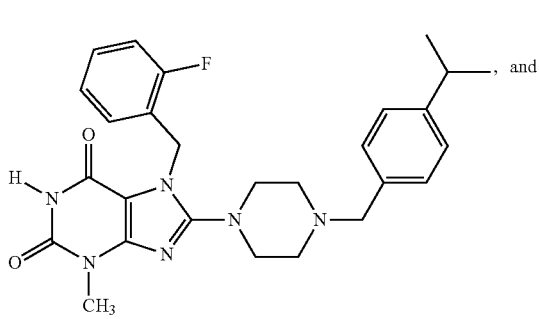

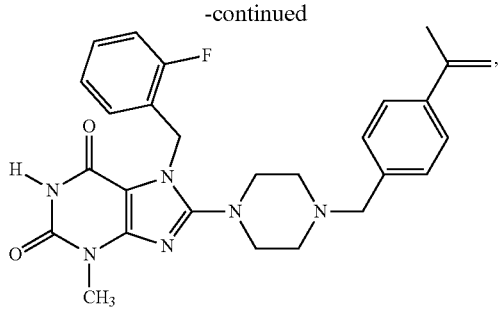

or a pharmaceutically acceptable salt thereof.

In a further aspect, the compound has a structure represented by a formula:

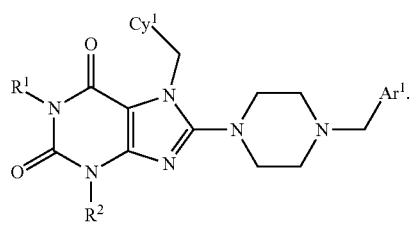

In a further aspect, the compound has a structure represented by a formula:

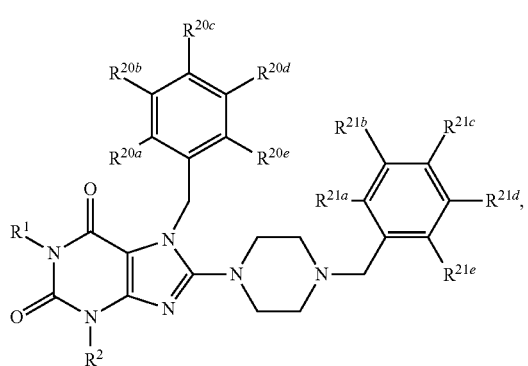

In a further aspect, the compound has a structure represented by a formula:

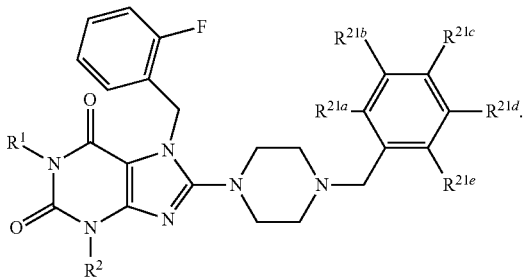

wherein each of $R^{20a}$, $R^{20b}$, $R^{20c}$, $R^{20d}$, and $R^{20e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl), provided at least two of $R^{20a}$, $R^{20b}$, $R^{20c}$, $R^{20d}$, and $R^{20e}$ are hydrogen, and wherein each of $R^{21a}$, $R^{21b}$, $R^{21c}$, $R^{21d}$, and $R^{21e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl), provided at least two of $R^{21a}$, $R^{21b}$, $R^{21c}$, $R^{21d}$, and $R^{21e}$ are hydrogen.

In a further aspect, the compound has a structure represented by a formula:

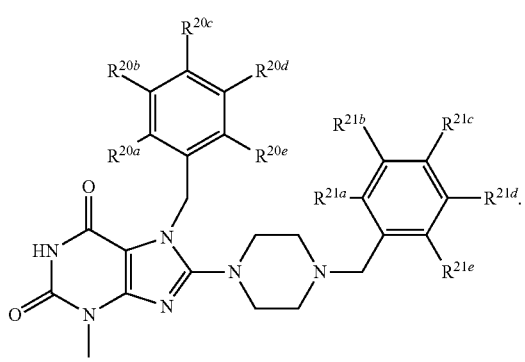

In a further aspect, the compound has a structure represented by a formula:

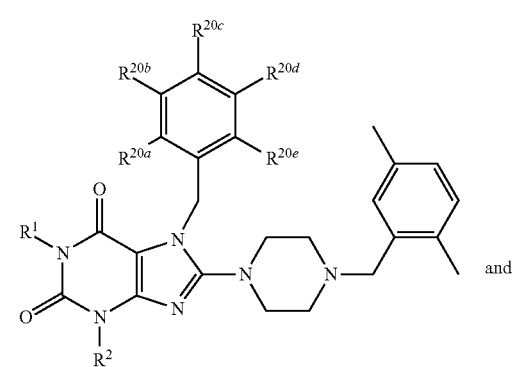

In a further aspect, the compound as a structure represented by a formula selected from:

-continued

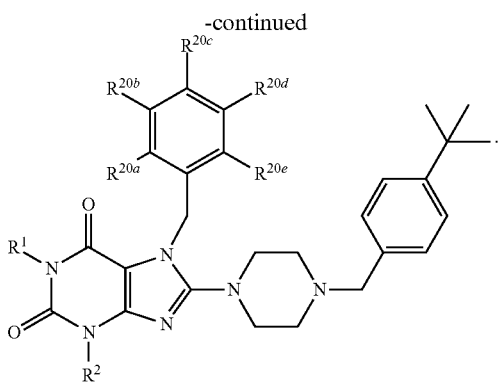

In a further aspect, the compound has a structure represented by a formula selected from:

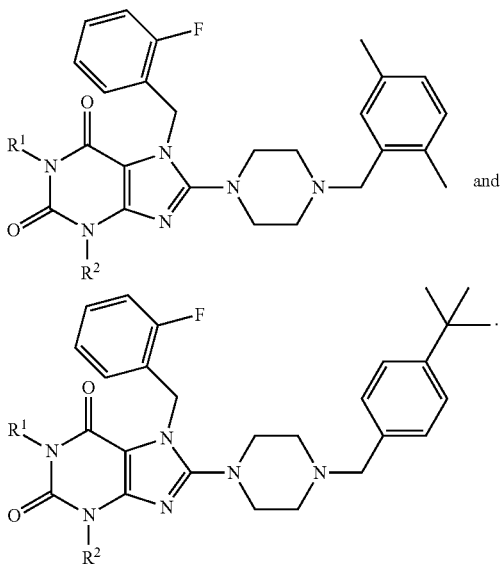

In a further aspect, $R^1$ is hydrogen and $R^2$ methyl.

In one aspect, n is selected from 0, 1, and 2. In a further aspect, n is selected from 0 and 1. In a still further aspect, n is selected from 0 and 2. In yet a further aspect, n is selected from 1 and 2. In an even further aspect, n is 0. In a still further aspect, n is 1. In yet a further aspect, n is 2.

a. A Groups

In one aspect, each occurrence of A, when present, is individually selected from —C(O)— and —CH$_2$—, provided that no more than one occurrence of A, when present, is —C(O)—. In a further aspect, each occurrence of A, when present, is —C(O)—. In a still further aspect, each occurrence of A, when present, is —CH$_2$—.

In a further aspect, one occurrence of A, when present, is —C(O)— and one occurrence of A, when present, is —CH$_2$—.

In a further aspect, A is absent.

b. Z Groups

In one aspect, Z is selected from N and CR$^{10}$. In a further aspect, Z is selected from N, CH, and C(CH$_3$). In a still further aspect, Z is selected from N and CH. In yet a further aspect, Z is selected from N and C(CH$_3$).

In a further aspect, Z is N.

In a further aspect, Z is CR$^{10}$. In a still further aspect, Z is selected from CH and C(CH$_3$). In yet a further aspect, Z is CH. In an even further aspect, Z is C(CH$_3$).

c. $R^1$ Groups

In one aspect, $R^1$ is selected from hydrogen, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH.

In a further aspect, $R^1$ is hydrogen.

In a further aspect, $R^1$ is selected from hydrogen, C1-C4 alkyl, C1-C4 cyanoalkyl, C1-C4 hydroxyalkyl, C1-C4 alkoxy, —(C1-C4 alkyl)-CO$_2$H, and —(C1-C4 alkyl)-O—(C-C4 alkyl)-OH. In a still further aspect, $R^1$ is selected from hydrogen, methyl, ethyl, n-propyl, i-propyl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)CH$_3$, —CH$_2$CO$_2$H, —CH$_2$CH$_2$CO$_2$H, —CH$_2$CH$_2$CH$_2$CO$_2$H, —CH(CH$_3$)CH$_2$CO$_2$H, —CH$_2$OCH$_2$OH, —CH$_2$CH$_2$OCH$_2$OH, and —CH$_2$CH$_2$CH$_2$OCH$_2$OH. In yet a further aspect, $R^1$ is selected from hydrogen, methyl, ethyl, —CH$_2$CN, —CH$_2$CH$_2$CN, —CH$_2$OH, —CH$_2$CH$_2$OH, —OCH$_3$, —OCH$_2$CH$_3$, —CH$_2$CO$_2$H, —CH$_2$CH$_2$CO$_2$H, —CH$_2$OCH$_2$OH, and —CH$_2$CH$_2$OCH$_2$OH. In an even further aspect, $R^1$ is selected from hydrogen, methyl, —CH$_2$CN, —CH$_2$OH, —OCH$_3$, —CH$_2$CO$_2$H, and —CH$_2$OCH$_2$OH.

In a further aspect, $R^1$ is selected from hydrogen, C1-C4 alkyl, C1-C4 hydroxyalkyl, C1-C4 alkoxy, and —(C1-C4 alkyl)-O—(C1-C4 alkyl)-OH. In a still further aspect, $R^1$ is selected from hydrogen, methyl, ethyl, n-propyl, i-propyl, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)CH$_3$, —CH$_2$OCH$_2$OH, —CH$_2$CH$_2$OCH$_2$OH, and —CH$_2$CH$_2$CH$_2$OCH$_2$OH. In yet a further aspect, $R^1$ is selected from hydrogen, methyl, ethyl, —CH$_2$OH, —CH$_2$CH$_2$OH, —OCH$_3$, —OCH$_2$CH$_3$, —CH$_2$OCH$_2$OH, and —CH$_2$CH$_2$CH$_2$OH. In an even further aspect, $R^1$ is selected from hydrogen, methyl, —CH$_2$OH, —OCH$_3$, and —CH$_2$OCH$_2$OH.

In a further aspect, $R^1$ is selected from hydrogen, C1-C4 alkyl, C1-C4 hydroxyalkyl, C1-C4 alkoxy, C3-C6 cycloalkyl, and —CH$_2$(C3-C6 cycloalkyl). In a still further aspect, $R^1$ is selected from hydrogen, methyl, ethyl, n-propyl, i-propyl, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)CH$_3$, C3-C6 cycloalkyl, and —CH$_2$(C3-C6 cycloalkyl). In yet a further aspect, $R^1$ is selected from hydrogen, methyl, ethyl, n-propyl, i-propyl, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)CH$_3$, cyclopropyl, cyclobutyl, cyclopentyl, —CH$_2$(cyclopropyl), —CH$_2$(cyclobutyl), and —CH$_2$(cyclopentyl). In an even further aspect, $R^1$ is selected from hydrogen, methyl, ethyl, —CH$_2$OH, —CH$_2$CH$_2$OH, —OCH$_3$, —OCH$_2$CH$_3$, cyclopropyl, cyclobutyl, —CH$_2$(cyclopropyl), and —CH$_2$(cyclobutyl). In a still further aspect, $R^1$ is selected from hydrogen, methyl, ethyl, —CH$_2$OH, —CH$_2$CH$_2$OH, —OCH$_3$, —OCH$_2$CH$_3$, cyclopropyl, and —CH$_2$(cyclopropyl).

In a further aspect, $R^1$ is selected from hydrogen and C1-C4 alkyl. In a still further aspect, $R^1$ is selected from hydrogen, methyl, ethyl, n-propyl, and isopropyl. In yet a further aspect, $R^1$ is selected from hydrogen, methyl, and ethyl. In an even further aspect, $R^1$ is selected from hydrogen and ethyl. In a still further aspect, $R^1$ is selected from hydrogen and methyl.

In a further aspect, $R^1$ is C1-C4 alkyl. In a still further aspect, $R^1$ is selected from methyl, ethyl, n-propyl, and isopropyl. In yet a further aspect, $R^1$ is selected from methyl and ethyl. In an even further aspect, $R^1$ is ethyl. In a still further aspect, $R^1$ is methyl.

d. $R^2$ Groups

In one aspect, $R^2$ is selected from —OH, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH. In a further aspect, $R^2$ is hydrogen.

In a further aspect, $R^2$ is selected from hydrogen, C1-C4 alkyl, C1-C4 cyanoalkyl, C1-C4 hydroxyalkyl, C1-C4 alkoxy, —(C1-C4 alkyl)-CO$_2$H, and —(C1-C4 alkyl)-O—(C1-C4 alkyl)-OH. In a still further aspect, $R^2$ is selected from hydrogen, methyl, ethyl, n-propyl, i-propyl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)CH$_3$, —CH$_2$CO$_2$H, —CH$_2$CH$_2$CO$_2$H, —CH$_2$CH$_2$CH$_2$CO$_2$H, —CH(CH$_3$)CH$_2$CO$_2$H, —CH$_2$OCH$_2$OH, —CH$_2$CH$_2$OCH$_2$OH, and —CH$_2$CH$_2$CH$_2$OCH$_2$OH. In yet a further aspect, $R^2$ is selected from hydrogen, methyl, ethyl, —CH$_2$CN, —CH$_2$CH$_2$CN, —CH$_2$OH, —CH$_2$CH$_2$OH, —OCH$_3$, —OCH$_2$CH$_3$, —CH$_2$CO$_2$H, —CH$_2$CH$_2$CO$_2$H, —CH$_2$OCH$_2$OH, and —CH$_2$CH$_2$OCH$_2$OH. In an even further aspect, $R^2$ is selected from hydrogen, methyl, —CH$_2$CN, —CH$_2$OH, —OCH$_3$, —CH$_2$CO$_2$H, and —CH$_2$OCH$_2$OH.

In a further aspect, $R^2$ is selected from hydrogen, C1-C4 alkyl, C1-C4 hydroxyalkyl, C1-C4 alkoxy, and —(C1-C4 alkyl)-O—(C1-C4 alkyl)-OH. In a still further aspect, $R^2$ is selected from hydrogen, methyl, ethyl, n-propyl, i-propyl, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)CH$_3$, —CH$_2$OCH$_2$OH, —CH$_2$CH$_2$OCH$_2$OH, and —CH$_2$CH$_2$CH$_2$OCH$_2$OH. In yet a further aspect, $R^2$ is selected from hydrogen, methyl, ethyl, —CH$_2$OH, —CH$_2$CH$_2$OH, —OCH$_3$, —OCH$_2$CH$_3$, —CH$_2$OCH$_2$OH, and —CH$_2$CH$_2$OH. In an even further aspect, $R^2$ is selected from hydrogen, methyl, —CH$_2$OH, —OCH$_3$, and —CH$_2$OCH$_2$OH.

In a further aspect, $R^2$ is selected from hydrogen, C1-C4 alkyl, C1-C4 hydroxyalkyl, C1-C4 alkoxy, C3-C6 cycloalkyl, and —CH$_2$(C3-C6 cycloalkyl). In a still further aspect, $R^2$ is selected from hydrogen, methyl, ethyl, n-propyl, i-propyl, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)CH$_3$, C3-C6 cycloalkyl, and —CH$_2$(C3-C6 cycloalkyl). In yet a further aspect, $R^2$ is selected from hydrogen, methyl, ethyl, n-propyl, i-propyl, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)CH$_3$, cyclopropyl, cyclobutyl, cyclopentyl, —CH$_2$(cyclopropyl), —CH$_2$(cyclobutyl), and —CH$_2$(cyclopentyl). In an even further aspect, $R^2$ is selected from hydrogen, methyl, ethyl, —CH$_2$OH, —CH$_2$CH$_2$OH, —OCH$_3$, —OCH$_2$CH$_3$, cyclopropyl, cyclobutyl, —CH$_2$(cyclopropyl), and —CH$_2$(cyclobutyl). In a still further aspect, $R^2$ is selected from hydrogen, methyl, ethyl, —CH$_2$OH, —CH$_2$CH$_2$OH, —OCH$_3$, —OCH$_2$CH$_3$, cyclopropyl, and —CH$_2$(cyclopropyl).

In a further aspect, $R^2$ is selected from hydrogen and C1-C4 alkyl. In a still further aspect, $R^2$ is selected from hydrogen, methyl, ethyl, n-propyl, and isopropyl. In yet a further aspect, $R^2$ is selected from hydrogen, methyl, and ethyl. In an even further aspect, $R^2$ is selected from hydrogen and ethyl. In a still further aspect, $R^2$ is selected from hydrogen and methyl.

In a further aspect, $R^2$ is C1-C4 alkyl. In a still further aspect, $R^2$ is selected from methyl, ethyl, n-propyl, and isopropyl. In yet a further aspect, $R^2$ is selected from methyl and ethyl. In an even further aspect, $R^2$ is ethyl. In a still further aspect, $R^2$ is methyl.

e. $R^3$ Groups

In one aspect, $R^3$ is selected from C1-C4 alkyl and $Ar^1$, provided that when $R^3$ is methyl then $R^{10}$ is not hydrogen and provided that when Z is N then $R^3$ is $Cy^2$.

In a further aspect, $R^3$ is selected from methyl, ethyl, n-propyl, isopropyl, and $Ar^1$. In a still further aspect, $R^3$ is selected from methyl, ethyl, and $Ar^1$. In yet a further aspect, $R^3$ is selected from ethyl and $Ar^1$. In an even further aspect, $R^3$ is selected from methyl and $Ar^1$.

In a further aspect, $R^3$ is C1-C4 alkyl. In a still further aspect, $R^3$ is selected from methyl, ethyl, n-propyl, and isopropyl. In yet a further aspect, $R^3$ is selected from methyl and ethyl. In an even further aspect, $R^3$ is ethyl. In an even further aspect, $R^3$ is methyl.

In a further aspect, $R^3$ is $Ar^1$. In a further aspect, $R^3$ is selected from 6-membered aryl and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, $R^3$ is 6-membered aryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, $R^3$ is 6-membered heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl).

f. $R^{4a}$, $R^{4b}$, $R^{4c}$, and $R^{4d}$ Groups

In one aspect, each of $R^{4a}$, $R^{4b}$, $R^{4c}$, and $R^{4d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, —CO$_2$H, and —CO$_2$(C1-C4 alkyl). In a further aspect, each of $R^{4a}$, $R^{4a}$, $R^{4b}$, $R^{4c}$, and $R^{4d}$ is hydrogen.

In a further aspect, each of $R^{4a}$, $R^{4b}$, $R^{4c}$, and $R^{4d}$ is independently selected from hydrogen, halogen, —CN, —NH$_2$, —OH, —NO$_2$, methyl, ethyl, n-propyl, isopropyl, ethenyl, propenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$C, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CO$_2$H, —CO$_2$CH$_3$, —CO$_2$CH$_2$CH$_3$, —C$_2$CH$_2$CH$_2$CH$_3$, and —C$_2$CH(CH$_3$)CH$_3$. In a still further aspect, each of $R^{4a}$, $R^{4b}$, $R^{4c}$, and $R^{4d}$ is independently selected from hydrogen, —F, —Cl, —CN, —NH$_2$, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CO$_2$H, —CO$_2$CH$_3$, and —CO$_2$CH$_2$CH$_3$. In yet a further aspect, each of R$^{4a}$, R$^{4b}$, R$^{4c}$, and R$^{4d}$ is independently selected from hydrogen, —F, —Cl, —CN, —NH$_2$, —OH, —NO$_2$, methyl, —CH$_2$F, —CH$_2$Cl, —CH$_2$CN, —CH$_2$OH, —OCF$_3$, —OCH$_3$, —NHCH$_3$, —N(CH$_3$)$_2$, —CO$_2$H, and —CO$_2$CH$_3$.

In a further aspect, each of R$^{4a}$, R$^{4b}$, R$^{4c}$, and R$^{4d}$ is independently selected from hydrogen and C1-C4 alkyl. In a still further aspect, each of R$^{4a}$, R$^{4b}$, R$^{4c}$, and R$^{4d}$ is independently selected from hydrogen, methyl, ethyl, n-propyl, and isopropyl. In yet a further aspect, each of R$^{4a}$, R$^{4b}$, R$^{4c}$, and R$^{4d}$ is independently selected from hydrogen, methyl, and ethyl. In an even further aspect, each of R$^{4a}$, R$^{4b}$, R$^{4c}$, and R$^{4d}$ is independently selected from hydrogen and ethyl. In a still further aspect, each of R$^{4a}$, R$^{4b}$, R$^{4c}$, and R$^{4d}$ is independently selected from hydrogen and methyl.

In a further aspect, each of R$^{4a}$, R$^{4b}$, R$^{4c}$, and R$^{4d}$ is independently selected from hydrogen and halogen. In a still further aspect, each of R$^{4a}$, R$^{4b}$, R$^{4c}$, and R$^{4d}$ is independently selected from hydrogen, —F, —Cl, and —I. In yet a further aspect, each of R$^{4a}$, R$^{4b}$, R$^{4c}$, and R$^{4d}$ is independently selected from hydrogen, —F, and —Cl. In an even further aspect, each of R$^{4a}$, R$^{4b}$, R$^{4c}$, and R$^{4d}$ is independently selected from hydrogen and —F. In a still further aspect, each of R$^{4a}$, R$^{4b}$, R$^{4c}$, and R$^{4d}$ is independently selected from hydrogen and —Cl.

In a further aspect, each of R$^{4a}$, R$^{4b}$, R$^{4c}$, and R$^{4d}$ is —CO$_2$H.

g. R$^{10}$ Groups

In one aspect, R$^{10}$, when present, is selected from hydrogen and C1-C4 alkyl. In a further aspect, R$^{10}$, when present, is hydrogen.

In a further aspect, R$^{10}$, when present, is selected from hydrogen, methyl, ethyl, n-propyl, and isopropyl. In a still further aspect, R$^{10}$, when present, is selected from hydrogen, methyl, and ethyl. In yet a further aspect, R$^{10}$, when present, is selected from hydrogen and ethyl. In an even further aspect, R$^{10}$, when present, is selected from hydrogen and methyl.

In a further aspect, R$^{10}$, when present, is selected from methyl, ethyl, n-propyl, and isopropyl. In a still further aspect, R$^{10}$, when present, is selected from methyl and ethyl. In yet a further aspect, R$^{10}$, when present, is ethyl. In an even further aspect, R$^{10}$, when present, is methyl.

h. R$^{20a}$, R$^{20b}$, R$^{20c}$, R$^{20d}$, and R$^{20e}$ Groups

In one aspect, each of R$^{20a}$, R$^{20b}$, R$^{20c}$, R$^{20d}$, and R$^{20e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —C$_2$(C1-C4 alkyl), provided at least two of R$^{20a}$, R$^{20b}$, R$^{20c}$, R$^{20d}$, and R$^{20e}$ are hydrogen. In a further aspect, each of R$^{20a}$, R$^{20b}$, R$^{20c}$, R$^{20d}$, and R$^{20e}$ is hydrogen.

In a further aspect, each of R$^{20a}$, R$^{20b}$, R$^{20c}$, R$^{20d}$, and R$^{20e}$ is independently selected from hydrogen, halogen, —CN, —NH$_2$, —OH, —NO$_2$, methyl, ethyl, n-propyl, isopropyl, ethenyl, propenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$C, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CO$_2$H, —CO$_2$CH$_3$, —CO$_2$CH$_2$CH$_3$, —CO$_2$CH$_2$CH$_2$CH$_3$, and —CO$_2$CH(CH$_3$)CH$_3$. In a still further aspect, each of R$^{20a}$, R$^{20b}$, R$^{20c}$, R$^{20d}$, and R$^{20e}$ is independently selected from hydrogen, —F, —Cl, —CN, —NH$_2$, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CO$_2$H, —CO$_2$CH$_3$, and —CO$_2$CH$_2$CH$_3$. In yet a further aspect, each of R$^{20a}$, R$^{20b}$, R$^{20c}$, R$^{20d}$, and R$^{20e}$ is independently selected from hydrogen, —F, —Cl, —CN, —NH$_2$, —OH, —NO$_2$, methyl, —CH$_2$F, —CH$_2$Cl, —CH$_2$CN, —CH$_2$OH, —OCF$_3$, —OCH$_3$, —NHCH$_3$, —N(CH$_3$)$_2$, —CO$_2$H, and —CO$_2$CH$_3$.

In a further aspect, each of R$^{20a}$, R$^{20b}$, R$^{20c}$, R$^{20d}$, and R$^{20e}$ is independently selected from hydrogen and C1-C4 alkyl. In a still further aspect, each of each of R$^{20a}$, R$^{20b}$, R$^{20c}$, R$^{20d}$, and R$^{20e}$ is independently selected from hydrogen, methyl, ethyl, n-propyl, and isopropyl. In yet a further aspect, each of each of R$^{20a}$, R$^{20b}$, R$^{20c}$, R$^{20d}$, and R$^{20e}$ is independently selected from hydrogen, methyl, and ethyl. In an even further aspect, each of each of R$^{20a}$, R$^{20b}$, R$^{20c}$, R$^{20d}$, and R$^{20e}$ is independently selected from hydrogen and ethyl. In a still further aspect, each of R$^{20a}$, R$^{20b}$, R$^{20c}$, R$^{20d}$, and R$^{20e}$ is independently selected from hydrogen and methyl.

In a further aspect, each of R$^{20a}$, R$^{20b}$, R$^{20c}$, R$^{20d}$, and R$^{20e}$ is independently selected from hydrogen and halogen. In a still further aspect, each of R$^{20a}$, R$^{20b}$, R$^{20c}$, R$^{20d}$, and R$^{20e}$ is independently selected from hydrogen, —F, —Cl, and —I. In yet a further aspect, each of R$^{20a}$, R$^{20b}$, R$^{20c}$, R$^{20d}$, and R$^{20e}$ is independently selected from hydrogen, —F, and —Cl. In an even further aspect, each of R$^{20a}$, R$^{20b}$, R$^{20c}$, R$^{20d}$, and R$^{20e}$ is independently selected from hydrogen and —F. In a still further aspect, each of R$^{20a}$, R$^{20b}$, R$^{20c}$, R$^{20d}$, and R$^{20e}$ is independently selected from hydrogen and —Cl.

In a further aspect, each of R$^{20a}$, R$^{20b}$, R$^{20c}$, and R$^{20d}$ is hydrogen and R$^{20e}$ is selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a further aspect, each of R$^{20a}$, R$^{20b}$, R$^{20c}$, and R$^{20d}$ is hydrogen and R$^{20e}$ is selected from —CN, —NH$_2$, —OH, —NO$_2$, methyl, ethyl, n-propyl, isopropyl, ethenyl, propenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CO$_2$H, —CO$_2$CH$_3$, —CO$_2$CH$_2$CH$_3$, —CO$_2$CH$_2$CH$_2$CH$_3$, and —CO$_2$CH(CH$_3$)CH$_3$. In a still further aspect, each of R$^{20a}$, R$^{20b}$, R$^{20c}$, and R$^{20d}$ is hydrogen and $R^{20e}$ is selected from —F, —Cl, —CN, —NH$_2$, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CO$_2$H, —CO$_2$CH$_3$, and —CO$_2$CH$_2$CH$_3$. In yet a further aspect, each of $R^{20a}$, $R^{20b}$, $R^{20c}$, and $R^{20d}$ is hydrogen and $R^{20e}$ is selected from —F, —Cl, —CN, —NH$_2$, —OH, —NO$_2$, methyl, —CH$_2$F, —CH$_2$Cl, —CH$_2$CN, —CH$_2$OH, —OCF$_3$, —OCH$_3$, —NHCH$_3$, —N(CH$_3$)$_2$, —CO$_2$H, and —CO$_2$CH$_3$.

In an even further aspect, each of $R^{20a}$, $R^{20b}$, $R^{20c}$, and $R^{20d}$ is hydrogen and $R^{20e}$ is halogen. In a still further aspect, each of $R^{20a}$, $R^{20b}$, $R^{20c}$, and $R^{20d}$ is hydrogen and $R^{20e}$ is selected from —F, —Cl, and —I. In yet a further aspect, each of $R^{20a}$, $R^{20b}$, $R^{20c}$, and $R^{20d}$ is hydrogen and $R^{20e}$ is selected from —F and —Cl. In an even further aspect, each of $R^{20a}$, $R^{20b}$, $R^{20c}$, and $R^{20d}$ is hydrogen and $R^{20e}$ is —Cl. In a still further aspect, each of $R^{20a}$, $R^{20b}$, $R^{20c}$, and $R^{20d}$ is hydrogen and $R^{20e}$ is —F.

i. $R^{21a}$, $R^{21b}$, $R^{21c}$, $R^{21d}$, and $R^{21e}$ Groups

In one aspect, each of $R^{21a}$, $R^{21b}$, $R^{21c}$, $R^{21d}$, and $R^{21e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl), provided at least two of $R^{21a}$, $R^{21b}$, $R^{21d}$, and $R^{21e}$ are hydrogen. In a further aspect, each of $R^{21a}$, $R^{21b}$, $R^{21c}$, $R^{21d}$, and $R^{21e}$ is hydrogen.

In a further aspect, each of $R^{21a}$, $R^{21b}$, $R^{21c}$, $R^{21d}$, and $R^{21e}$ is independently selected from hydrogen, halogen, —CN, —NH$_2$, —OH, —NO$_2$, methyl, ethyl, n-propyl, isopropyl, ethenyl, propenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$C, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CO$_2$H, —CO$_2$CH$_3$, —CO$_2$CH$_2$CH$_3$, —CO$_2$CH$_2$CH$_2$CH$_3$, and —CO$_2$CH(CH$_3$)CH$_3$. In a still further aspect, each of $R^{21a}$, $R^{21b}$, $R^{21c}$, $R^{21d}$, and $R^{21e}$ is independently selected from hydrogen, —F, —Cl, —CN, —NH$_2$, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CO$_2$H, —CO$_2$CH$_3$, and —CO$_2$CH$_2$CH$_3$. In yet a further aspect, each of $R^{21a}$, $R^{21b}$, $R^{21c}$, $R^{21d}$, and $R^{21e}$ is independently selected from hydrogen, —F, —Cl, —CN, —NH$_2$, —OH, —NO$_2$, methyl, —CH$_2$F, —CH$_2$Cl, —CH$_2$CN, —CH$_2$OH, —OCF$_3$, —OCH$_3$, —NHCH$_3$, —N(CH$_3$)$_2$, —CO$_2$H, and —CO$_2$CH$_3$.

In a further aspect, each of $R^{21a}$, $R^{21b}$, $R^{21c}$, $R^{21d}$, and $R^{21e}$ is independently selected from hydrogen and C1-C4 alkyl. In a still further aspect, each of each of $R^{21a}$, $R^{21b}$, $R^{21c}$, $R^{21d}$, and $R^{21e}$ is independently selected from hydrogen, methyl, ethyl, n-propyl, and isopropyl. In yet a further aspect, each of each of $R^{21a}$, $R^{21b}$, $R^{21c}$, $R^{21d}$, and $R^{21e}$ is independently selected from hydrogen, methyl, and ethyl. In an even further aspect, each of each of $R^{21a}$, $R^{21b}$, $R^{21c}$, $R^{21d}$, and $R^{21e}$ is independently selected from hydrogen and ethyl. In a still further aspect, each of $R^{21a}$, $R^{21b}$, $R^{21c}$, $R^{21d}$, and $R^{21e}$ is independently selected from hydrogen and methyl.

In a further aspect, each of $R^{21a}$, $R^{21b}$, $R^{21c}$, $R^{21d}$, and $R^{21e}$ is independently selected from hydrogen and halogen. In a still further aspect, each of $R^{21a}$, $R^{21b}$, $R^{21c}$, $R^{21d}$, and $R^{21e}$ is independently selected from hydrogen, —F, —Cl, and —I. In yet a further aspect, each of $R^{21a}$, $R^{21b}$, $R^{21c}$, $R^{21d}$, and $R^{21e}$ is independently selected from hydrogen, —F, and —Cl. In an even further aspect, each of $R^{21a}$, $R^{21b}$, $R^{21c}$, $R^{21d}$, and $R^{21e}$ is independently selected from hydrogen and —F. In a still further aspect, each of $R^{21a}$, $R^{21b}$, $R^{21c}$, $R^{21d}$, and $R^{21e}$ is independently selected from hydrogen and —Cl.

In a further aspect, each of $R^{21a}$, $R^{21b}$, $R^{21d}$, and $R^{21e}$ is hydrogen and $R^{21c}$ is selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a further aspect, each of $R^{21a}$, $R^{21b}$, $R^{21d}$, and $R^{21e}$ is hydrogen and $R^{21c}$ is selected from —CN, —NH$_2$, —OH, —NO$_2$, methyl, ethyl, n-propyl, isopropyl, ethenyl, propenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CO$_2$H, —CO$_2$CH$_3$, —CO$_2$CH$_2$CH$_3$, —CO$_2$CH$_2$CH$_2$CH$_3$, and —C$_2$H(CH$_3$)CH$_3$. In a still further aspect, each of $R^{21a}$, $R^{21b}$, $R^{21d}$, and $R^{21e}$ is hydrogen and $R^{21c}$ is selected from —F, —Cl, —CN, —NH$_2$, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CO$_2$H, —CO$_2$CH$_3$, and —CO$_2$CH$_2$CH$_3$. In yet a further aspect, each of $R^{21a}$, $R^{21b}$, $R^{21d}$, and $R^{21e}$ is hydrogen and $R^{21c}$ is selected from —F, —Cl, —CN, —NH$_2$, —OH, —NO$_2$, methyl, —CH$_2$F, —CH$_2$Cl, —CH$_2$CN, —CH$_2$OH, —OCF$_3$, —OCH$_3$, —NHCH$_3$, —N(CH$_3$)$_2$, —CO$_2$H, and —CO$_2$CH$_3$.

In an even further aspect, each of $R^{21a}$, $R^{21b}$, $R^{21d}$, and $R^{21e}$ is hydrogen and $R^{21c}$ is C1-C4 alkyl. In a still further aspect, each of $R^{21a}$, $R^{21b}$, $R^{21d}$, and $R^{21e}$ is hydrogen and $R^{21c}$ is selected from methyl, ethyl, n-propyl, isopropyl, n-butyl, isobutyl, sec-butyl, and tert-butyl. In yet a further aspect, each of $R^{21a}$, $R^{21b}$, $R^{21c}$, and $R^{21d}$ is hydrogen and $R^{21e}$ is selected from ethyl, n-propyl, isopropyl, n-butyl, isobutyl, sec-butyl, and tert-butyl. In an even further aspect, each of $R^{21a}$, $R^{21b}$, $R^{21d}$, and $R^{21e}$ is hydrogen and $R^{21c}$ is selected from n-propyl, isopropyl, n-butyl, isobutyl, sec-butyl, and tert-butyl. In a still further aspect, each of $R^{21a}$, $R^{21b}$, $R^{21d}$, and $R^{21e}$ is hydrogen and $R^{21c}$ is selected from n-butyl, isobutyl, sec-butyl, and tert-butyl. In yet a further aspect, each of $R^{21a}$, $R^{21b}$, $R^{21d}$, and $R^{21e}$ is hydrogen and $R^{21c}$ is tert-butyl.

j. $Cy^1$ Groups

In one aspect, $Cy^1$ is selected from cyclohexyl, 6-membered aryl, and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl).

In a further aspect, $Cy^1$ is cyclohexyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —C$_2$(C1-C4 alkyl). In a still further aspect, $Cy^1$ is cyclohexyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, $Cy^1$ is cyclohexyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, $Cy^1$ is cyclohexyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, $Cy^1$ is unsubstituted cyclohexyl.

In a further aspect, $Cy^1$ is cyclohexyl substituted with 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C-C4) dialkylamino, and —CO$_2$(C1-C4 alkyl). In a still further aspect, $Cy^1$ is cyclohexyl substituted with 1 or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, $Cy^1$ is cyclohexyl substituted with 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C-C4) dialkylamino, and —CO$_2$(C1-C4 alkyl). In an even further aspect, $Cy^1$ is cyclohexyl substituted with 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl).

In a further aspect, $Cy^1$ is cyclohexyl substituted with 1, 2, or 3 halide groups. In a still further aspect, $Cy^1$ is cyclohexyl substituted with 1 or 2 halide groups. In yet a further aspect, $Cy^1$ is cyclohexyl monosubstituted with a halide group.

In a further aspect, $Cy^1$ is cyclohexyl substituted with 1, 2, or 3 fluoride groups. In a still further aspect, $Cy^1$ is cyclohexyl substituted with 1 or 2 fluoride groups. In yet a further aspect, $Cy^1$ is cyclohexyl monosubstituted with a fluoride group.

In a further aspect, $Cy^1$ is 6-membered aryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, $Cy^1$ is 6-membered aryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, $Cy^1$ is 6-membered aryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, $Cy^1$ is 6-membered aryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, $Cy^1$ is unsubstituted 6-membered aryl.

In a further aspect, $Cy^1$ is 6-membered aryl substituted with 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, $Cy^1$ is 6-membered aryl substituted with 1 or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, $Cy^1$ is 6-membered aryl substituted with 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, $Cy^1$ is 6-membered aryl substituted with 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl).

In a further aspect, $Cy^1$ is 6-membered aryl substituted with 1, 2, or 3 halide groups. In a still further aspect, $Cy^1$ is 6-membered aryl substituted with 1 or 2 halide groups. In yet a further aspect, $Cy^1$ is 6-membered aryl monosubstituted with a halide group.

In a further aspect, $Cy^1$ is 6-membered aryl substituted with 1, 2, or 3 fluoride groups. In a still further aspect, $Cy^1$ is 6-membered aryl substituted with 1 or 2 fluoride groups. In yet a further aspect, $Cy^1$ is 6-membered aryl monosubstituted with a fluoride group.

In a further aspect, $Cy^1$ is 6-membered heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Cy$^1$ is 6-membered heteroaryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, Cy$^1$ is 6-membered heteroaryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, Cy$^1$ is 6-membered heteroaryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Cy$^1$ is unsubstituted 6-membered heteroaryl.

In a further aspect, Cy$^1$ is 6-membered heteroaryl substituted with 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Cy$^1$ is 6-membered heteroaryl substituted with 1 or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, Cy$^1$ is 6-membered heteroaryl substituted with 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, Cy$^1$ is 6-membered heteroaryl substituted with 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl).

In a further aspect, Cy$^1$ is 6-membered heteroaryl substituted with 1, 2, or 3 halide groups. In a still further aspect, Cy$^1$ is 6-membered heteroaryl substituted with 1 or 2 halide groups. In yet a further aspect, Cy$^1$ is 6-membered heteroaryl monosubstituted with a halide group.

In a further aspect, Cy$^1$ is 6-membered heteroaryl substituted with 1, 2, or 3 fluoride groups. In a still further aspect, Cy$^1$ is 6-membered heteroaryl substituted with 1 or 2 fluoride groups. In yet a further aspect, Cy$^1$ is 6-membered heteroaryl monosubstituted with a fluoride group.

In a further aspect, Cy$^1$ is pyridinyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Cy$^1$ is pyridinyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialky-lamino, and —CO$_2$(C1-C4 alkyl). In yet a further aspect, Cy$^1$ is pyridinyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —C$_2$(C1-C4 alkyl). In an even further aspect, Cy$^1$ is pyridinyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Cy$^1$ is unsubstituted pyridinyl.

In a further aspect, Cy$^1$ is pyridinyl substituted with 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C-C4) dialkylamino, and —CO$_2$(C1-C4 alkyl). In a still further aspect, Cy$^1$ is pyridinyl substituted with 1 or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialky-lamino, and —CO$_2$(C1-C4 alkyl). In yet a further aspect, Cy$^1$ is pyridinyl substituted with 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, Cy$^1$ is pyridinyl substituted with 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl).

In a further aspect, Cy$^1$ is pyridinyl substituted with 1, 2, or 3 halide groups. In a still further aspect, Cy$^1$ is pyridinyl substituted with 1 or 2 halide groups. In yet a further aspect, Cy$^1$ is pyridinyl monosubstituted with a halide group.

In a further aspect, Cy$^1$ is pyridinyl substituted with 1, 2, or 3 fluoride groups. In a still further aspect, Cy$^1$ is pyridinyl substituted with 1 or 2 fluoride groups. In yet a further aspect, Cy$^1$ is pyridinyl monosubstituted with a fluoride group.

k. Ar$^1$ Groups

In one aspect, Ar$^1$, when present, is selected from 6-membered aryl and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a further aspect, Ar$^1$, when present, is selected from 6-membered aryl and 6-membered heteroaryl, and is substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Ar$^1$, when present, is selected from 6-membered aryl and 6-membered heteroaryl, and is substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-

C4)(C1-C4) dialkylamino, and —CO$_2$(C1-C4 alkyl). In yet a further aspect, Ar$^1$, when present, is selected from 6-membered aryl and 6-membered heteroaryl, and is monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, Ar$^1$, when present, is selected from 6-membered aryl and 6-membered heteroaryl, and is unsubstituted.

In a further aspect, Ar$^1$ is 6-membered aryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Ar$^1$ is 6-membered aryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, Ar$^1$ is 6-membered aryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, Ar$^1$ is 6-membered aryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Ar$^1$ is unsubstituted 6-membered aryl.

In a further aspect, Ar$^1$ is 6-membered aryl substituted with 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Ar$^1$ is 6-membered aryl substituted with 1 or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, Ar$^1$ is 6-membered aryl di-substituted with groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, Ar$^1$ is 6-membered aryl tri-substituted with groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl).

In a further aspect, Ar$^1$ is 6-membered aryl substituted with 1, 2, or 3 independently selected C1-C4 alkyl groups. In a still further aspect, Ar$^1$ is 6-membered aryl substituted with 1 or 2 independently selected C1-C4 alkyl groups. In yet a further aspect, Ar$^1$ is 6-membered aryl monosubstituted with a C1-C4 alkyl group. In an even further aspect, Ar$^1$ is 6-membered aryl substituted with 2 independently selected C1-C4 alkyl groups. In a still further aspect, Ar$^1$ is 6-membered aryl substituted with 3 independently selected C1-C4 alkyl groups.

In a further aspect, Ar$^1$ is 6-membered aryl substituted with 1, 2, or 3 tert-butyl groups. In a still further aspect, Ar$^1$ is 6-membered aryl substituted with 1 or 2 tert-butyl groups. In yet a further aspect, Ar$^1$ is 6-membered aryl monosubstituted with a tert-butyl group. In an even further aspect, Ar$^1$ is 6-membered aryl substituted with 2 tert-butyl groups. In a still further aspect, Ar$^1$ is 6-membered aryl substituted with 3 tert-butyl groups.

In a further aspect, Ar$^1$ is 6-membered aryl substituted with 1, 2, or 3 methyl groups. In a still further aspect, Ar$^1$ is 6-membered aryl substituted with 1 or 2 methyl groups. In yet a further aspect, Ar$^1$ is 6-membered aryl monosubstituted with a methyl group. In an even further aspect, Ar$^1$ is 6-membered aryl substituted with 2 methyl groups. In yet a further aspect, Ar$^1$ is 6-membered aryl substituted with 3 methyl groups.

In a further aspect, Ar$^1$ is 6-membered heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Ar$^1$ is 6-membered heteroaryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, Ar$^1$ is 6-membered heteroaryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, Ar$^1$ is 6-membered heteroaryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Ar$^1$ is unsubstituted 6-membered heteroaryl.

In a further aspect, Ar$^1$ is 6-membered heteroaryl substituted with 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Ar$^1$ is 6-membered heteroaryl substituted with 1 or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, Ar$^1$ is 6-membered heteroaryl di-substituted with groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, Ar$^1$ is 6-membered heteroaryl tri-substituted with groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl).

In a further aspect, Ar$^1$ is 6-membered heteroaryl substituted with 1, 2, or 3 independently selected C1-C4 alkyl groups. In a still further aspect, Ar$^1$ is 6-membered heteroaryl substituted with 1 or 2 independently selected C1-C4 alkyl groups. In yet a further aspect. Ar$^1$ is 6-membered heteroaryl monosubstituted with a C1-C4 alkyl group. In an even further aspect, Ar$^1$ is 6-membered heteroaryl substituted with 2 independently selected C1-C4 alkyl groups. In a still further aspect, Ar$^1$ is 6-membered heteroaryl substituted with 3 independently selected C1-C4 alkyl groups.

In a further aspect, Ar$^1$ is 6-membered heteroaryl substituted with 1, 2, or 3 tert-butyl groups. In a still further aspect, Ar$^1$ is 6-membered heteroaryl substituted with 1 or 2 tert-butyl groups. In yet a further aspect, Ar$^1$ is 6-membered heteroaryl monosubstituted with a tert-butyl group. In an even further aspect, Ar$^1$ is 6-membered heteroaryl substituted with 2 tert-butyl groups. In a still further aspect, Ar$^1$ is 6-membered heteroaryl substituted with 3 tert-butyl groups.

In a further aspect, Ar$^1$ is 6-membered heteroaryl substituted with 1, 2, or 3 methyl groups. In a still further aspect, Ar$^1$ is 6-membered heteroaryl substituted with 1 or 2 methyl groups. In yet a further aspect, Ar$^1$ is 6-membered heteroaryl monosubstituted with a methyl group. In an even further aspect, Ar$^1$ is 6-membered heteroaryl substituted with 2 methyl groups. In yet a further aspect, Ar$^1$ is 6-membered heteroaryl substituted with 3 methyl groups.

In a further aspect, Ar$^1$ is pyridinyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Ar$^1$ is pyridinyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, Ar$^1$ is pyridinyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, Ar$^1$ is pyridinyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Ar$^1$ is unsubstituted pyridinyl.

In a further aspect, Ar$^1$ is pyridinyl substituted with 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In a still further aspect, Ar$^1$ is pyridinyl substituted with 1 or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In yet a further aspect, Ar$^1$ is pyridinyl di-substituted with groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl). In an even further aspect, Ar$^1$ is pyridinyl tri-substituted with groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl).

In a further aspect, Ar$^1$ is pyridinyl substituted with 1, 2, or 3 independently selected C1-C4 alkyl groups. In a still further aspect, Ar$^1$ is pyridinyl substituted with 1 or 2 independently selected C1-C4 alkyl groups. In yet a further aspect. Ar$^1$ is pyridinyl monosubstituted with a C1-C4 alkyl group. In an even further aspect, Ar$^1$ is pyridinyl substituted with 2 independently selected C1-C4 alkyl groups. In a still further aspect, Ar$^1$ is pyridinyl substituted with 3 independently selected C1-C4 alkyl groups.

In a further aspect, Ar$^1$ is pyridinyl substituted with 1, 2, or 3 tert-butyl groups. In a still further aspect, Ar$^1$ is pyridinyl substituted with 1 or 2 tert-butyl groups. In yet a further aspect, Ar$^1$ is pyridinyl monosubstituted with a tert-butyl group. In an even further aspect, Ar$^1$ is pyridinyl substituted with 2 tert-butyl groups. In a still further aspect, Ar$^1$ is pyridinyl substituted with 3 tert-butyl groups.

In a further aspect, Ar$^1$ is pyridinyl substituted with 1, 2, or 3 methyl groups. In a still further aspect, Ar$^1$ is pyridinyl substituted with 1 or 2 methyl groups. In yet a further aspect, Ar$^1$ is pyridinyl monosubstituted with a methyl group. In an even further aspect, Ar$^1$ is pyridinyl substituted with 2 methyl groups. In yet a further aspect, Ar$^1$ is pyridinyl substituted with 3 methyl groups.

2. Example Compounds

In one aspect, a compound can be present as one or more of the following structures:

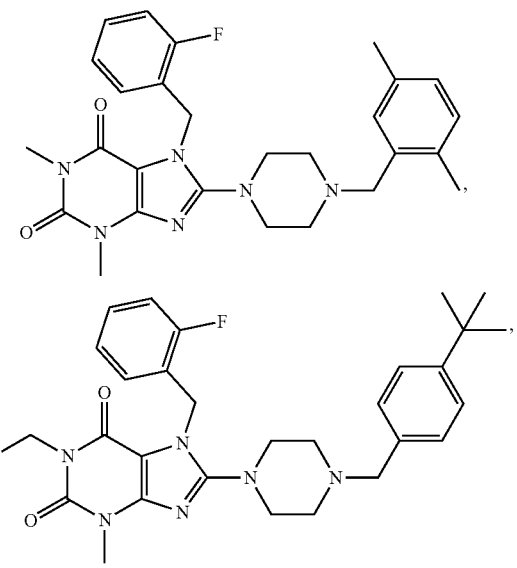

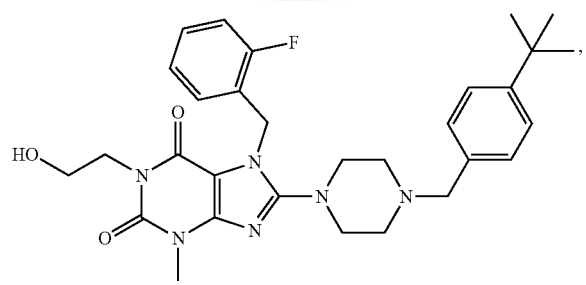
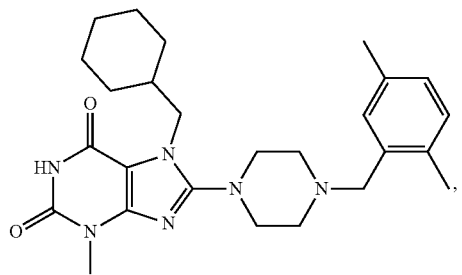
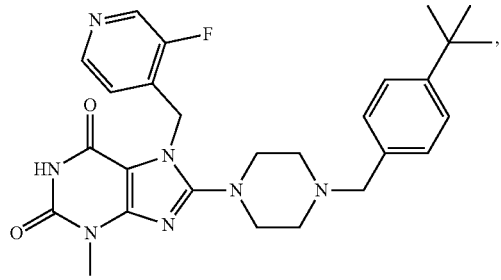
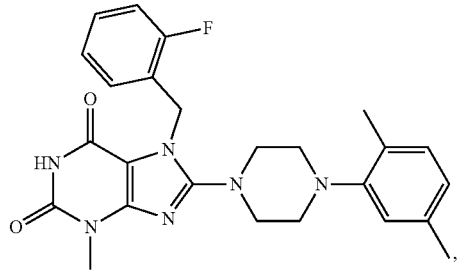
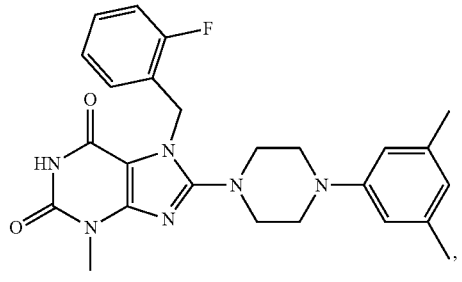
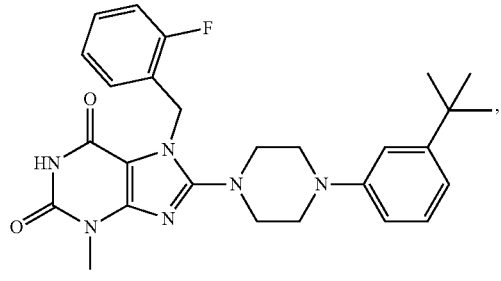
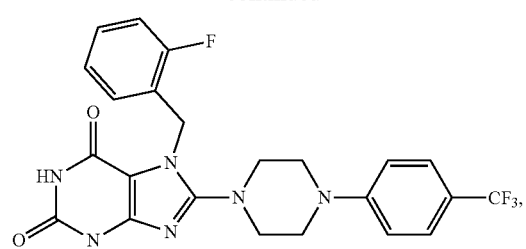
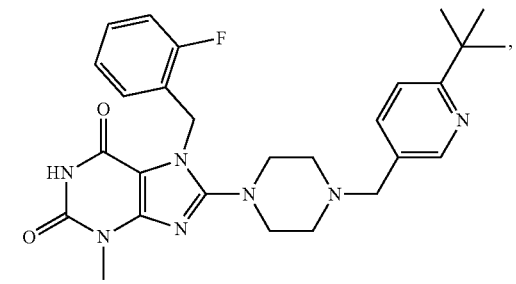
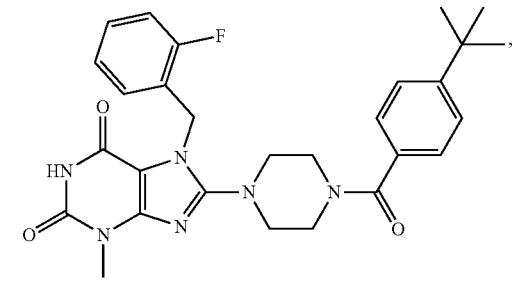
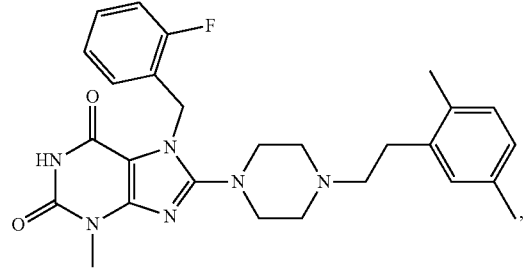
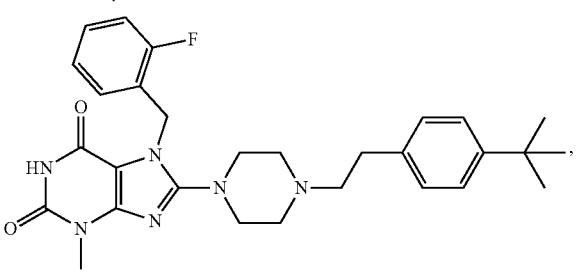
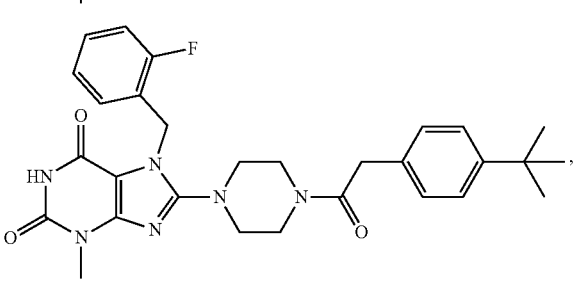

-continued
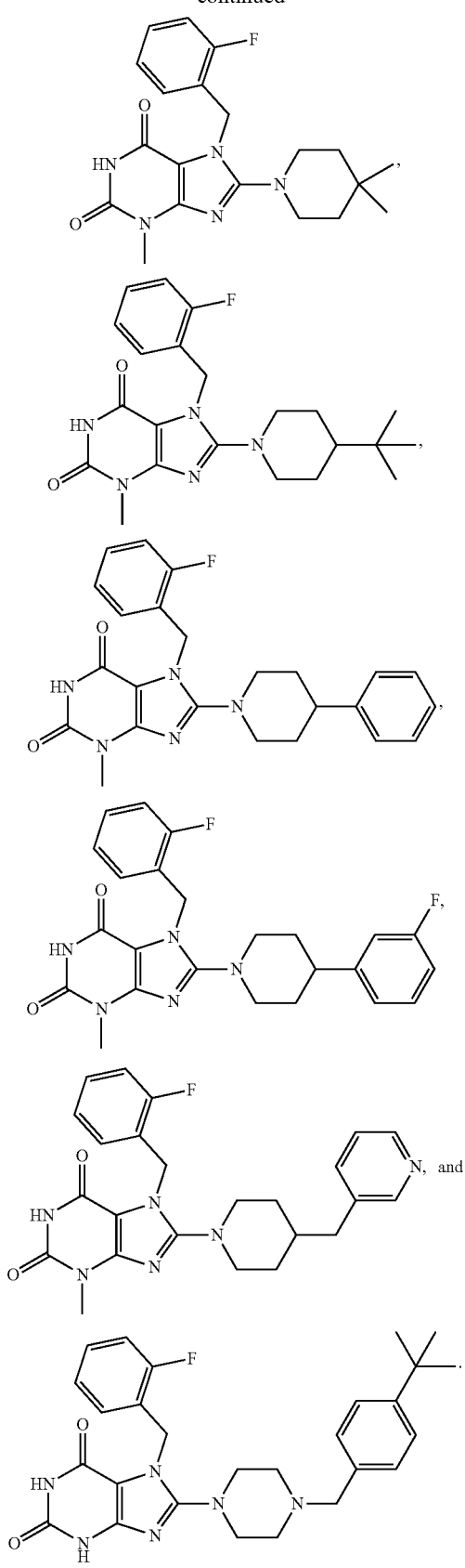
or a pharmaceutically acceptable salt thereof.
In one aspect, a compound can be present as one or more of the following structures:
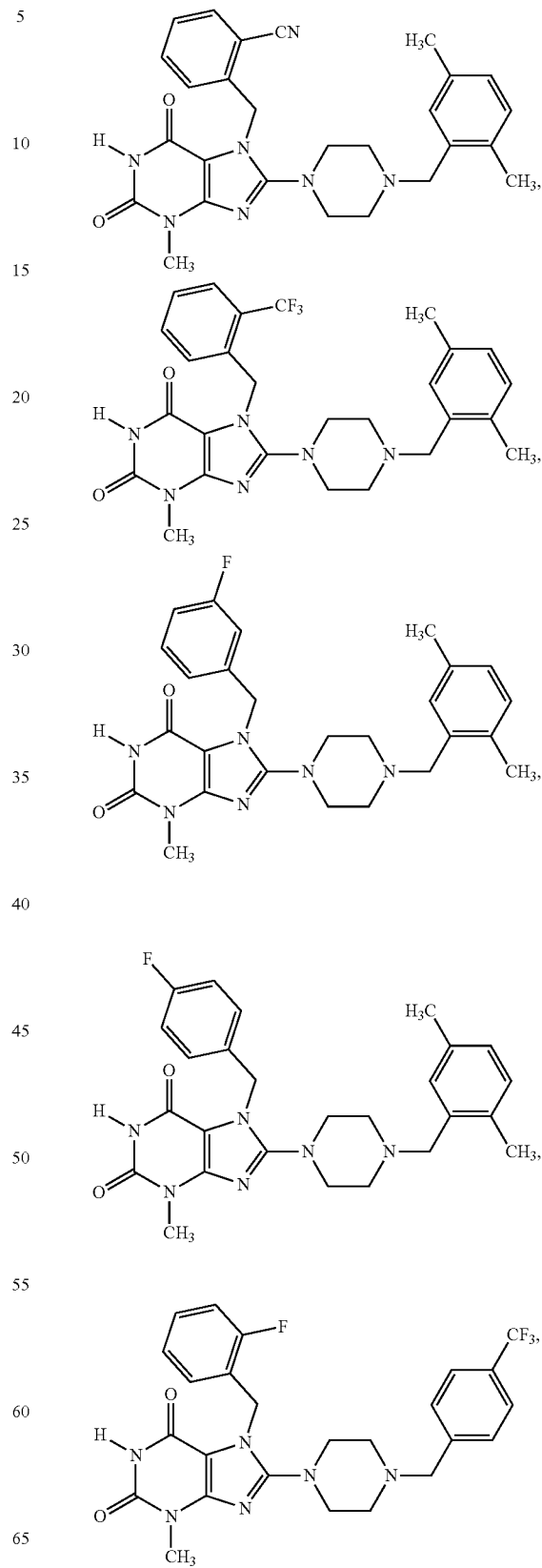

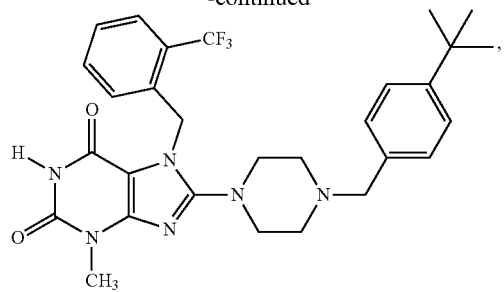
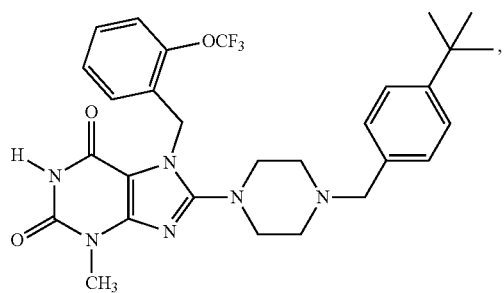
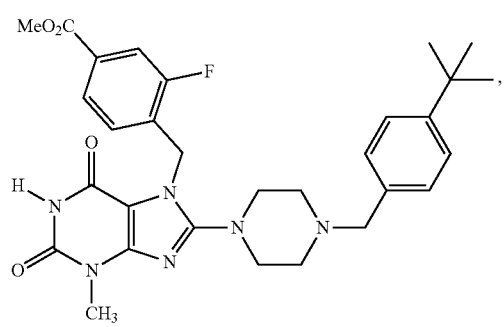
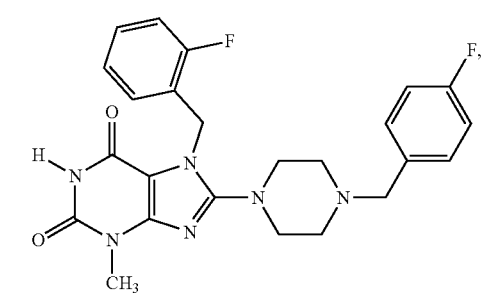
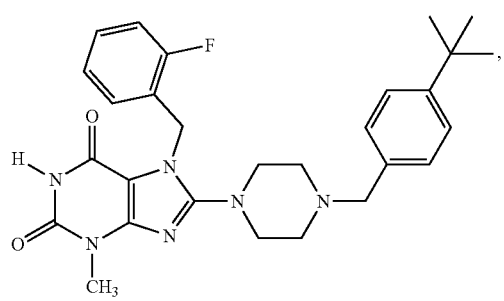
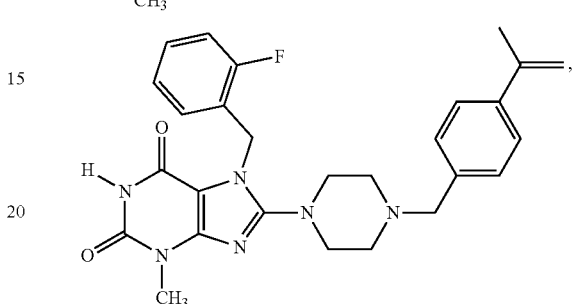
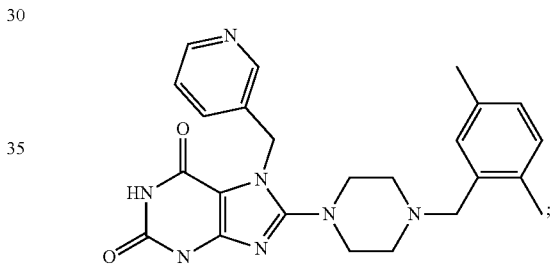
or a pharmaceutically acceptable salt thereof.
In one aspect, a compound is not:
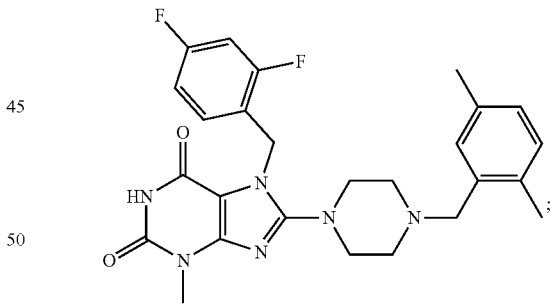
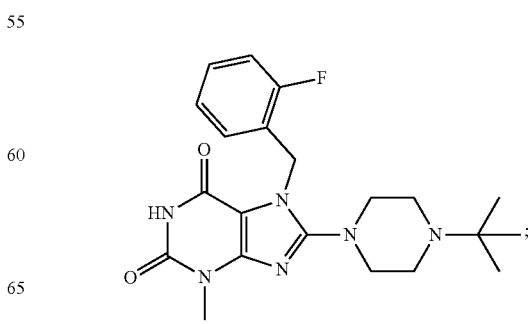

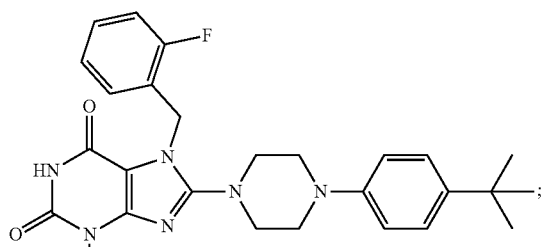
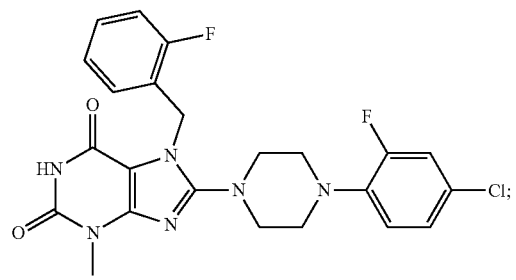
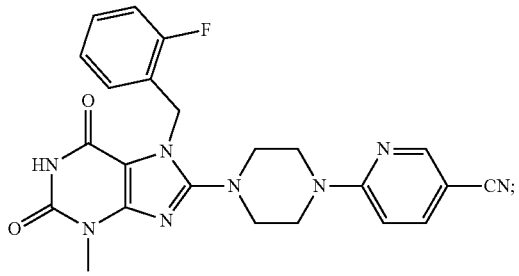
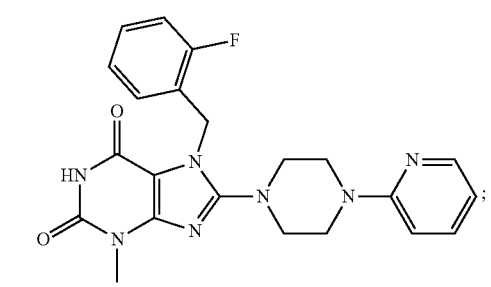
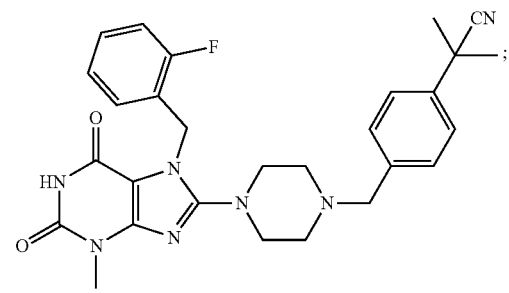
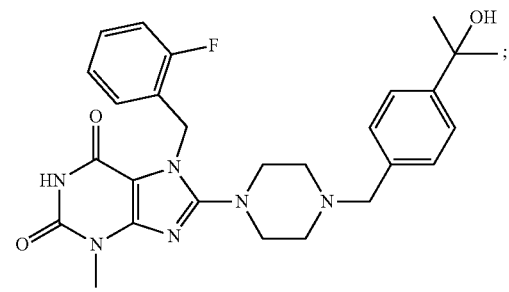

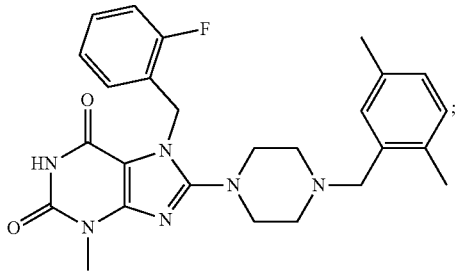
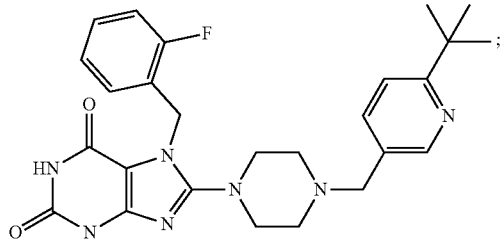
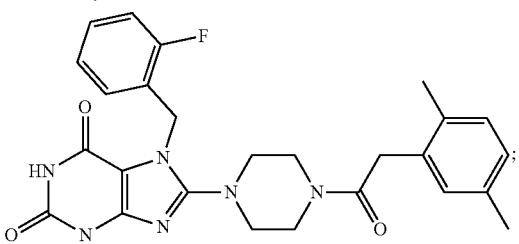
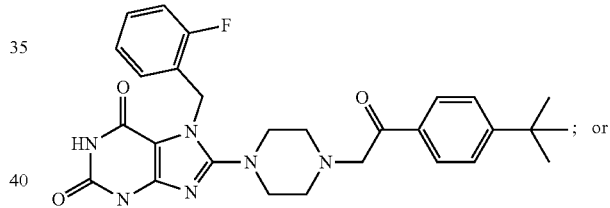
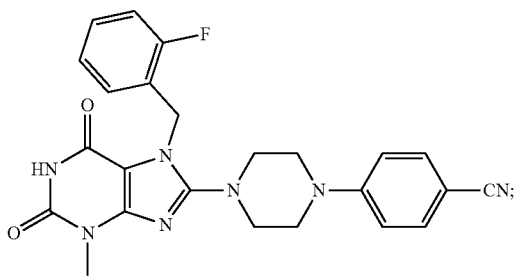

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of TGF-β, and such activity can be determined using the assay methods described herein.

In one aspect, a compound can be selected from:
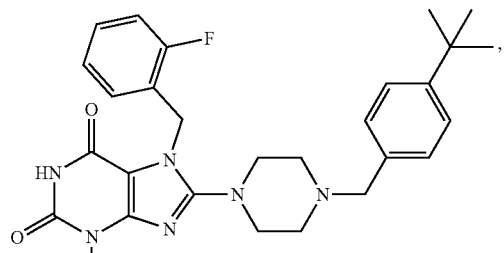
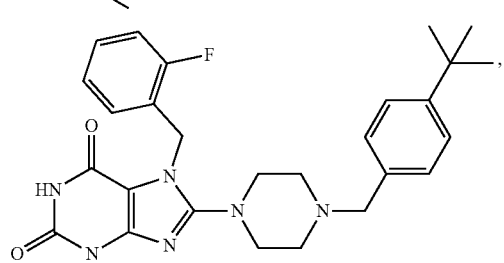
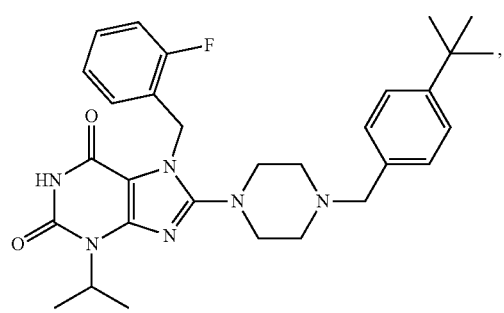
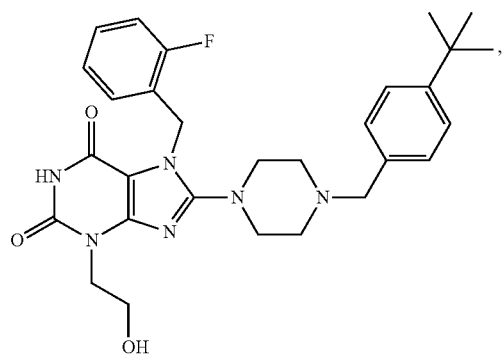
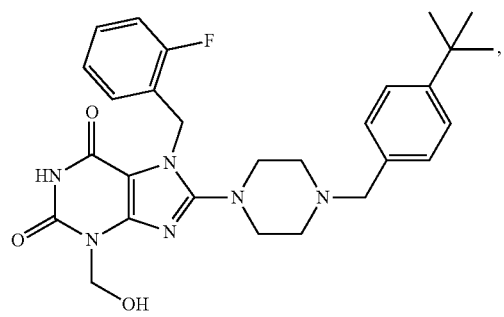
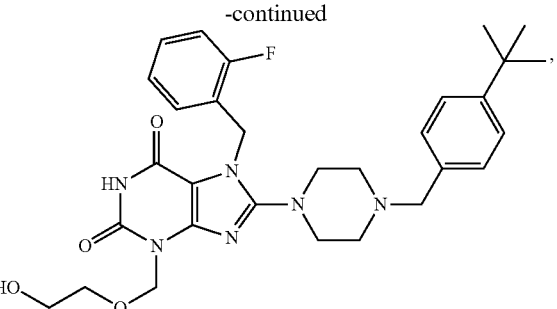
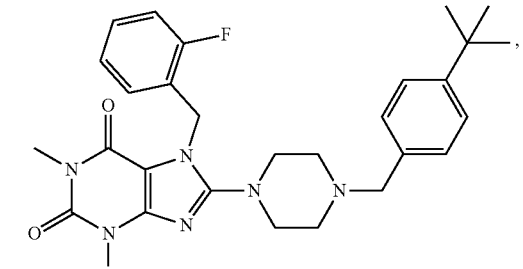
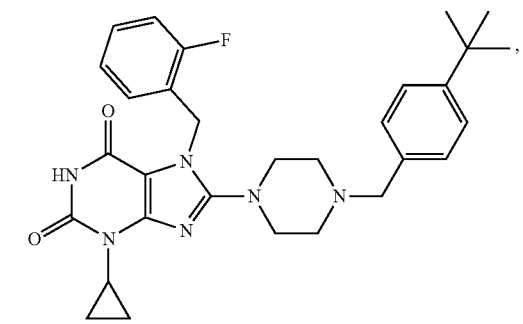
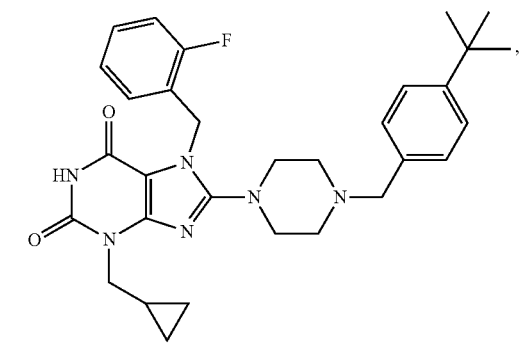
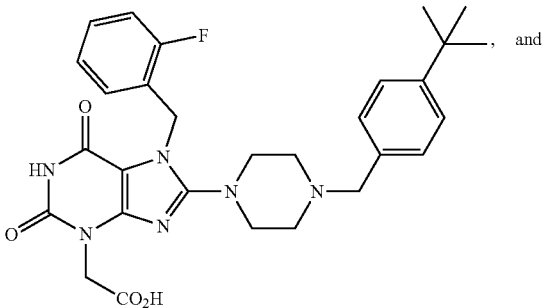

-continued

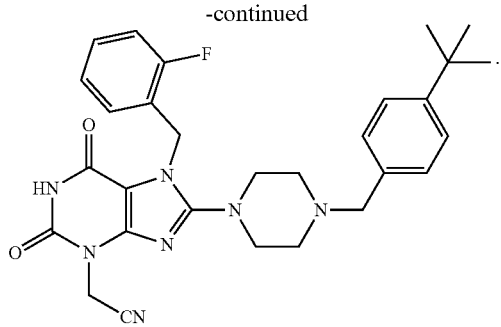

or a pharmaceutically acceptable salt thereof.

C. Pharmaceutical Compositions

In one aspect, disclosed are pharmaceutical compositions comprising a therapeutically effective amount at least one disclosed compound and a pharmaceutically acceptable carrier. In a further aspect, a pharmaceutical composition can be provided comprising a therapeutically effective amount of at least one disclosed compound. In a still further aspect, a pharmaceutical composition can be provided comprising a prophylactically effective amount of at least one disclosed compound. In yet a further aspect, the invention relates to pharmaceutical compositions comprising a pharmaceutically acceptable carrier and a compound, wherein the compound is present in an effective amount.

Thus, in one aspect, disclosed are pharmaceutical compositions comprising a therapeutically effective amount of a compound having a structure represented by a formula:

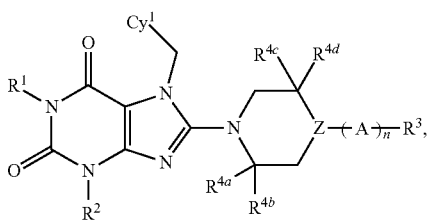

wherein n is selected from 0, 1, and 2; wherein each occurrence of A, when present, is individually selected from —C(O)— and —CH$_2$—, provided that no more than one occurrence of A, when present, is —C(O)—; wherein Z is selected from N and CR$^{10}$; wherein R$^{10}$, when present, is selected from hydrogen and C1-C4 alkyl; wherein R$^1$ is selected from hydrogen, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^2$ is selected from —OH, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^3$ is selected from C1-C4 alkyl and Ar$^1$, provided that when R$^3$ is methyl then R$^{10}$ is not hydrogen and provided that when Z is N then R$^3$ is Cy$^2$; wherein Ar$^1$, when present, is selected from 6-membered aryl and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl); and wherein each of R$^{4a}$, R$^{4b}$, R$^{4c}$, and R$^{4d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, —CO$_2$H, and —CO$_2$(C1-C4 alkyl); wherein Cy$^1$ is selected from cyclohexyl, 6-membered aryl, and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl), provided that when n is 1, A is CH$_2$, R$^1$ is hydrogen or methyl, R$^2$ is methyl, R$^3$ is 6-membered aryl, and Cy$^1$ is 6-membered aryl, then R$^1$, when present, is C1-C4 alkyl, and provided that when each occurrence of A, when present, is CH$_2$, R$^1$ is hydrogen, R$^2$ is methyl, R$^3$ is 6-membered aryl, and Cy$^1$ is 6-membered aryl, then Z is CR$^{10}$, or a pharmaceutically acceptable salt thereof, and a pharmaceutically acceptable carrier.

In one aspect, disclosed are pharmaceutical compositions comprising a therapeutically effective amount of a compound selected from:

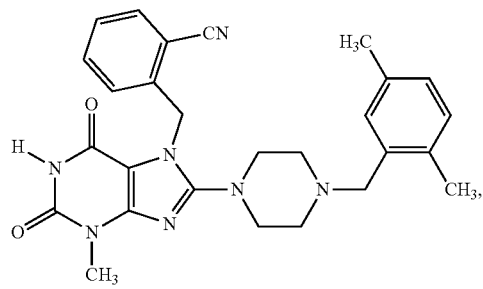

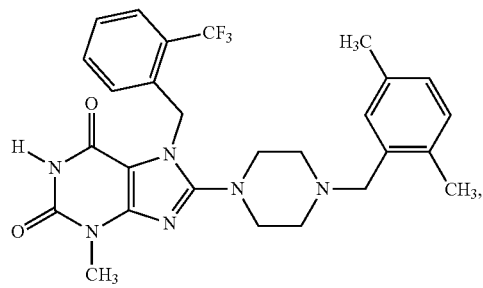

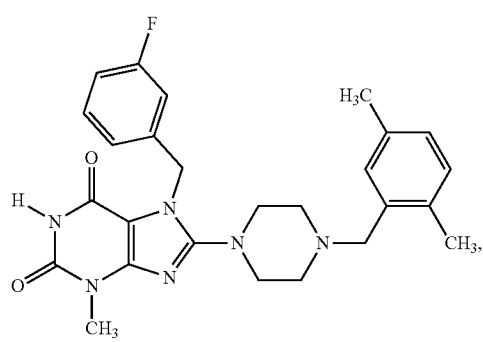

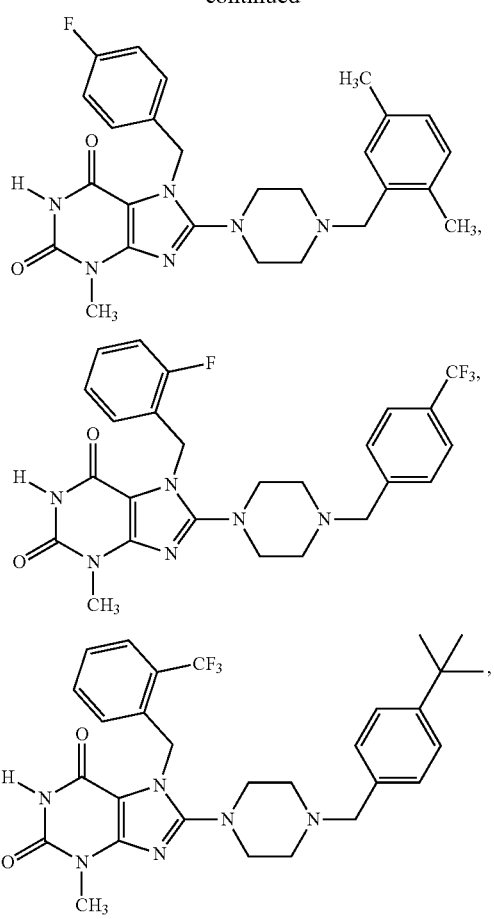

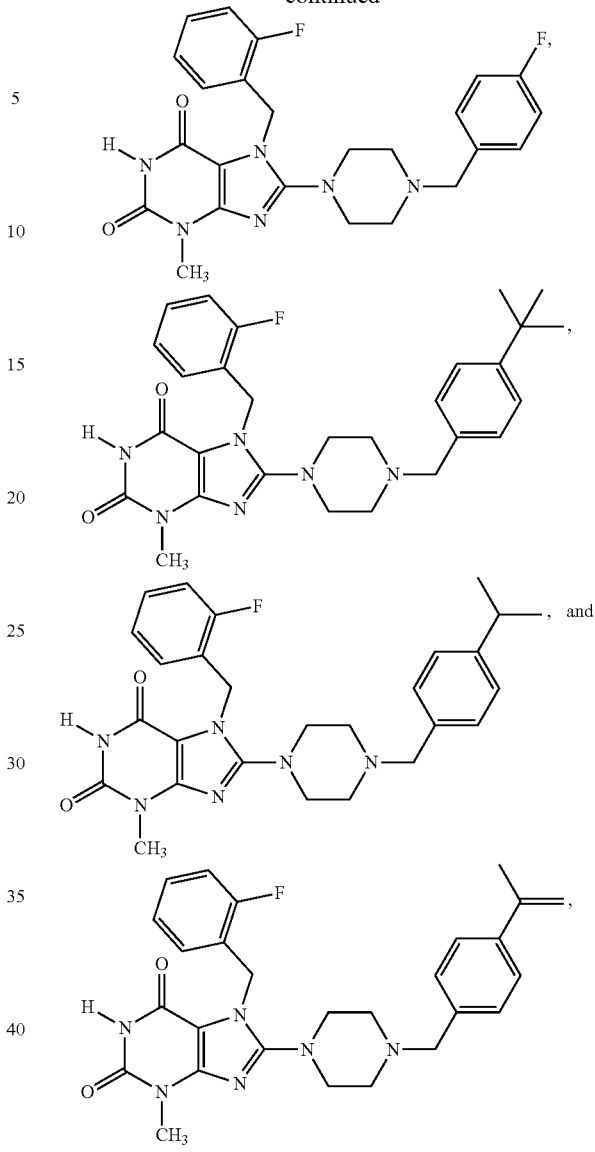

or a pharmaceutically acceptable salt thereof, and a pharmaceutically acceptable carrier.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In a further aspect, the pharmaceutical composition is administered to a mammal. In a still further aspect, the mammal is a human. In an even further aspect, the human is a patient.

In a further aspect, the pharmaceutical composition is administered following identification of the mammal in need of treatment of West Nile virus. In a still further aspect, the mammal has been diagnosed with a need for treatment of West Nile virus prior to the administering step.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The compounds of the present disclosure alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1, 3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example. dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, $4^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the treatment (e.g., prophylactic or therapeutic) of West Nile virus. The method also includes the administration of a therapeutically effect amount of the compound for the treatment of patient having a predisposition for being afflicted with West Nile virus. The dose administered to an animal, particularly a human, in the context of the present invention should be sufficient to affect a therapeutic response in the animal over a reasonable timeframe. One skilled in the art will recognize that dosage will depend upon a variety of factors including the condition of the animal, the body weight of the animal, as well as the severity and stage of the virus.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

In a further aspect, the composition further comprises at least one antiviral agent. Examples of antiviral agents include, but are not limited to, acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, zinc salts, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

It is understood that the disclosed compositions can be prepared from the disclosed compounds. It is also understood that the disclosed compositions can be employed in the disclosed methods of using.

D. Methods of Making the Compounds

In various aspects, the inventions relates to methods of making compounds useful to treat West Nile virus. Thus, in one aspect, disclosed are methods of making a disclosed compound.

Compounds according to the present disclosure can, for example, be prepared by the several methods outlined below. A practitioner skilled in the art will understand the appropriate use of protecting groups [see: Greene and Wuts, Protective Groups in Organic Synthesis] and the preparation of known compounds found in the literature using the standard methods of organic synthesis. There may come from time to time the need to rearrange the order of the recommended synthetic steps, however this will be apparent to the judgment of a chemist skilled in the art of organic synthesis. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, xanthine analogs can be prepared as shown below.

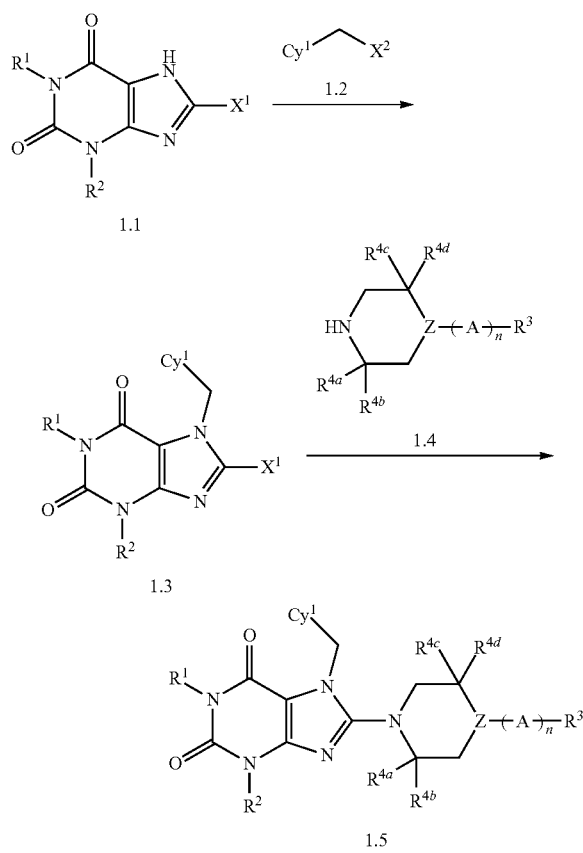

Compounds are represented in generic form, where each of $X^1$ and $X^2$ are independently halogen and with substituents as noted in compound descriptions elsewhere herein. A more specific example is set forth below.

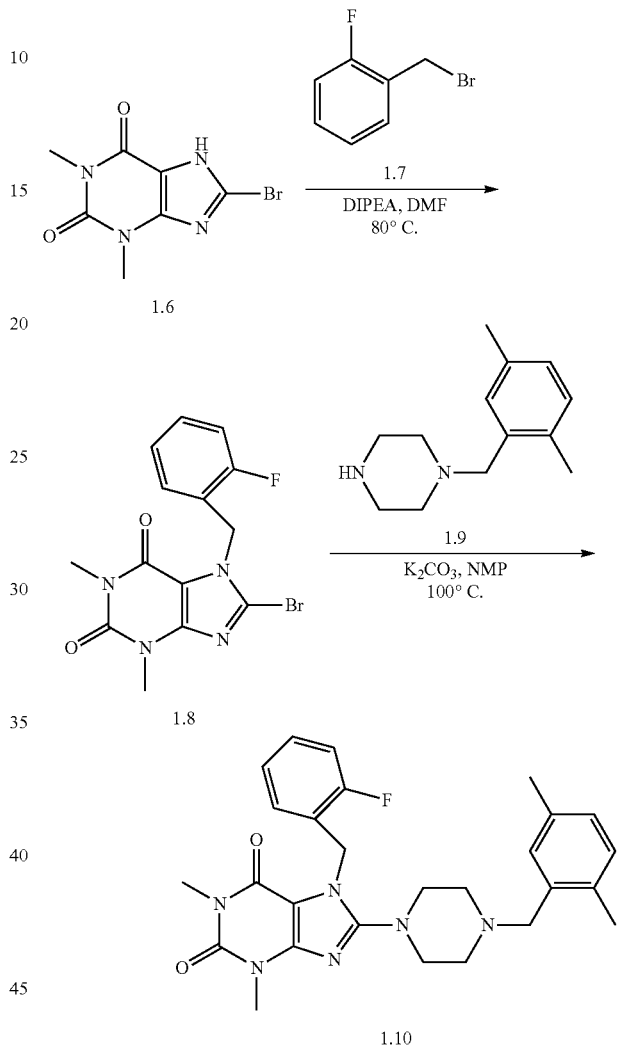

In one aspect, compounds of type 1.5, and similar compounds, can be prepared according to reaction Scheme 1B above. Thus, compounds of type 1.8 can be prepared by a coupling reaction of an appropriate xanthine analog, e.g., 1.6 as shown above, and an appropriate halide, e.g., 1.7 as shown above. Appropriate xanthine analogs and appropriate halides are commercially available or prepared by methods known to one skilled in the art. The coupling reaction is carried out in the presence of an appropriate base, e.g., diisopropylethylamine (DIPEA), in an appropriate solvent, e.g., dimethylformamide (DMF), at an appropriate temperature, e.g., 80° C. Compounds of type 1.10 can be prepared by a coupling reaction of an appropriate halide, e.g., 1.8 as shown above, and an appropriate amine, e.g., 1.9 as shown above. Appropriate amines are commercially available or prepared by methods known to one skilled in the art. The coupling reaction is carried out in the presence of an appropriate base, e.g., potassium carbonate, in an appropriate solvent, e.g., N-methylpyrrolidinone (NMP), at an appropriate temperature, e.g., 100° C. As can be appreciated by one skilled in the art, the above reaction provides an example of a generalized approach wherein compounds similar in structure to the specific reactants above (compounds similar to compounds of type 1.1, 1.2, 1.3, and 1.4), can be substituted in the reaction to provide substituted xanthine analogs similar to Formula 1.5.

2. Route II

In one aspect, xanthine analogs can be prepared as shown below.

substituents as noted in compound descriptions elsewhere herein. A more specific example is set forth below.

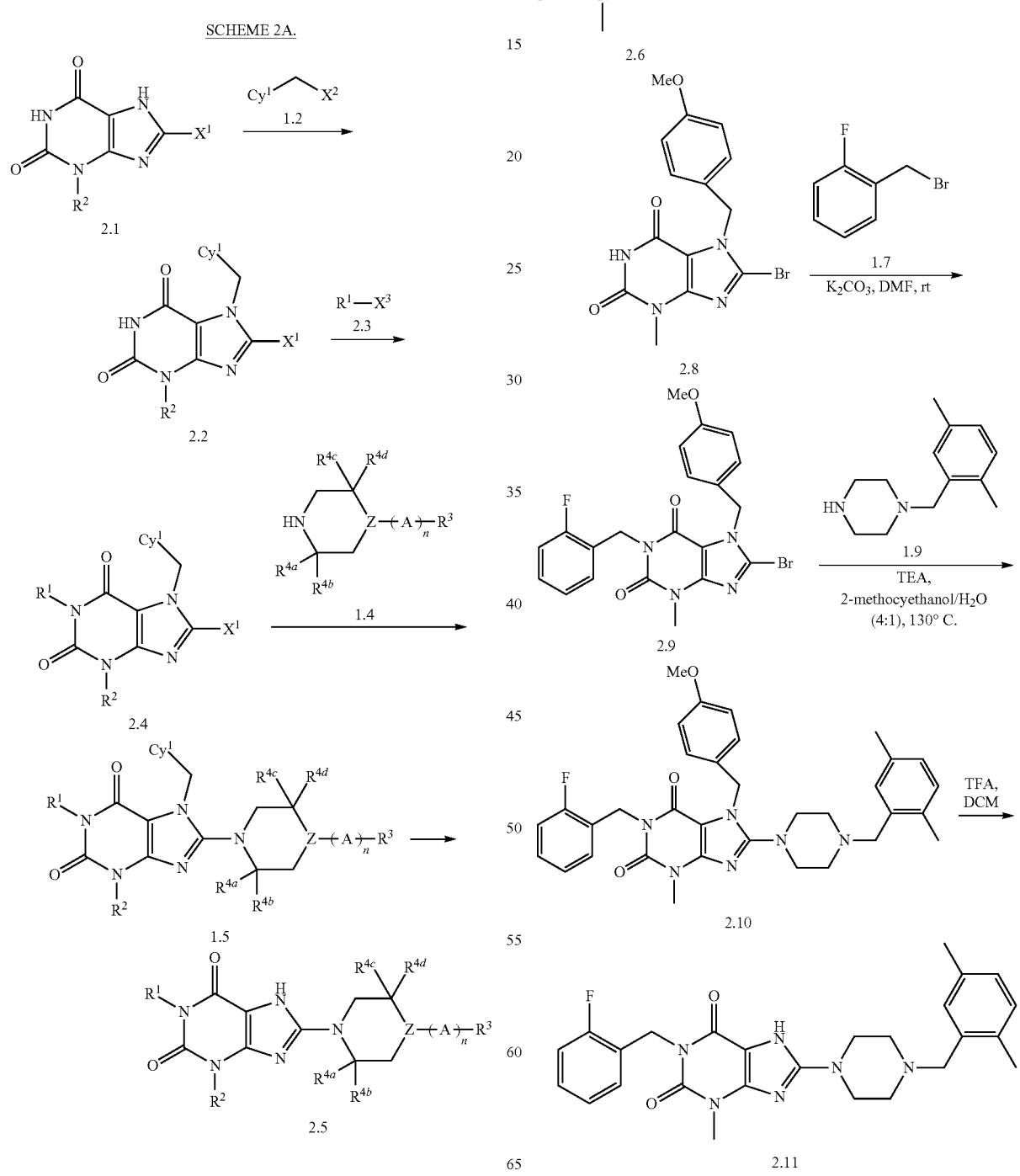

Compounds are represented in generic form, where each of $X^1$, $X^2$, and $X^3$ are independently halogen and with In one aspect, compounds of type 2.5, and similar compounds, can be prepared according to reaction Scheme 2B above. Thus, compounds of type 2.8 can be prepared by a coupling reaction of an appropriate xanthine analog, e.g., 2.6 as shown above, and an appropriate halide, e.g., 2.7 as shown above. Appropriate xanthine analogs and appropriate halides are commercially available or prepared by methods known to one skilled in the art. The coupling reaction is carried out in the presence of an appropriate base, e.g., DIPEA, in an appropriate solvent, e.g., DMF, at an appropriate temperature, e.g., 80° C. Compounds of type 2.9 can be prepared by a coupling reaction of an appropriate amine, e.g., 2.8 as shown above, and an appropriate halide, e.g., 1.7 as shown above. Appropriate halides are commercially available or prepared by methods known to one skilled in the art. The coupling reaction is carried out in the presence of an appropriate base, e.g., potassium carbonate, in an appropriate solvent, e.g., DMF. Compounds of type 2.10 can be prepared by a coupling reaction of an appropriate halide, e.g., 2.9 as shown above, and an appropriate amine, e.g., 1.9 as shown above. Appropriate amines are commercially available or prepared by methods known to one skilled in the art. The coupling reaction is carried out in the presence of an appropriate base, e.g., trimethylamine (TEA), in an appropriate solvent system, e.g., 2-methoxyethanol/H₂O (4:1), at an appropriate temperature, e.g., 130° C. Compounds of type 2.11 can be prepared by deprotection of an appropriate protected amine, e.g., 2.10 as shown above. The deprotection is carried out in the presence of an appropriate deprotecting agent, e.g., trifluoroacetic acid (TFA), in an appropriate solvent, e.g., dichloromethane (DCM). As can be appreciated by one skilled in the art, the above reaction provides an example of a generalized approach wherein compounds similar in structure to the specific reactants above (compounds similar to compounds of type 1.2, 1.4, 1.5, 2.1, 2.2, 2.3, and 2.4), can be substituted in the reaction to provide substituted xanthine analogs similar to Formula 2.5.

3. Route III

In one aspect, xanthine analogs can be prepared as shown below.

SCHEME 3A.

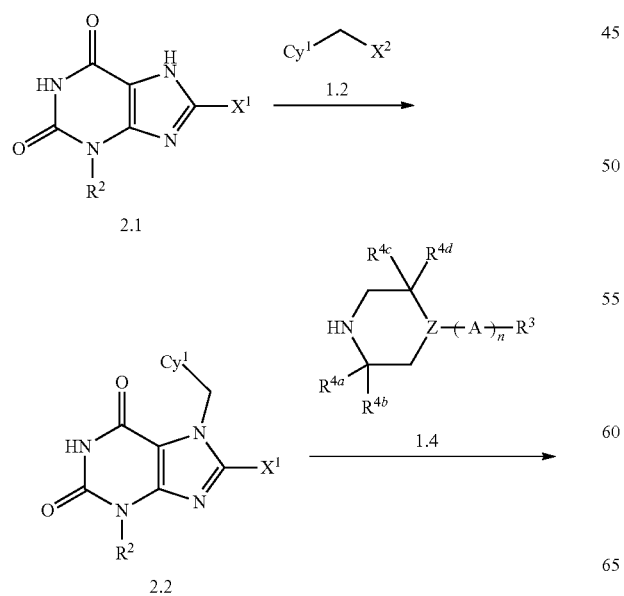

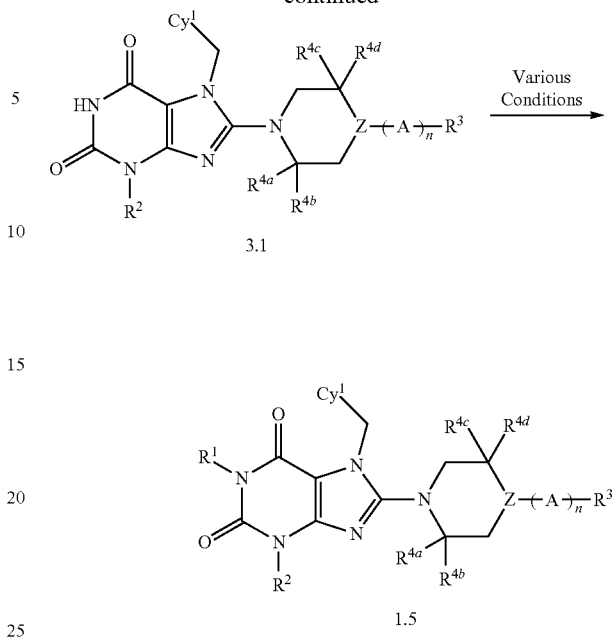

Compounds are represented in generic form, where each of $X^1$ and $X^2$ are independently halogen and with substituents as noted in compound descriptions elsewhere herein. A more specific example is set forth below.

SCHEME 3B.

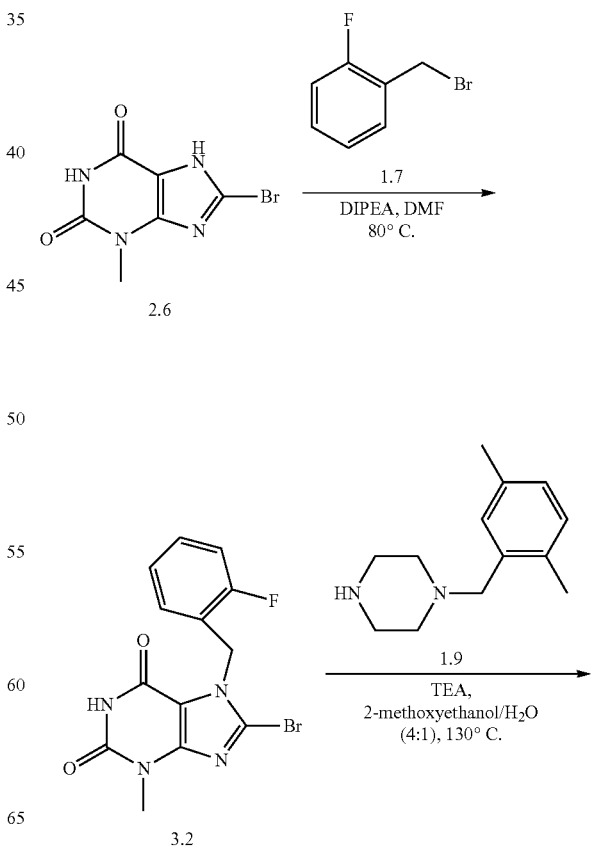

SCHEME 4A.

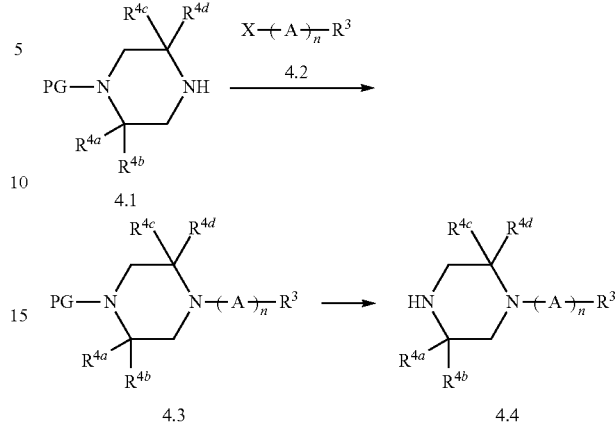

Compounds are represented in generic form, where PG is an amine protecting group, x is halogen, and with substituents as noted in compound descriptions elsewhere herein. A more specific example is set forth below.

SCHEME 4B.

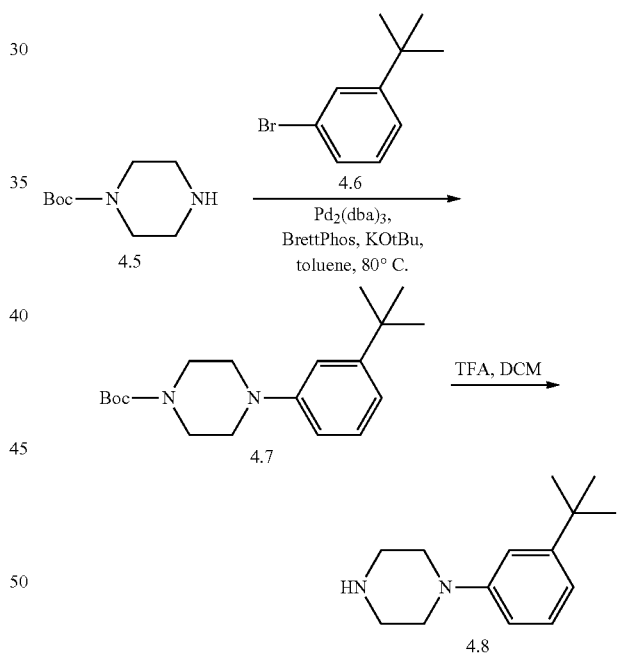

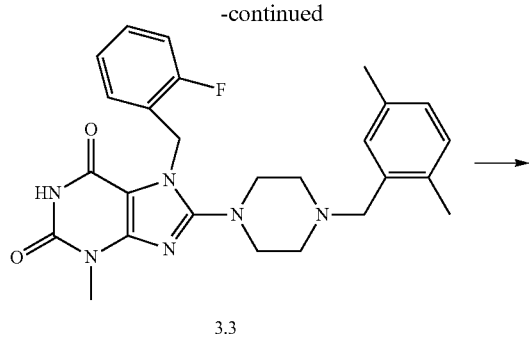

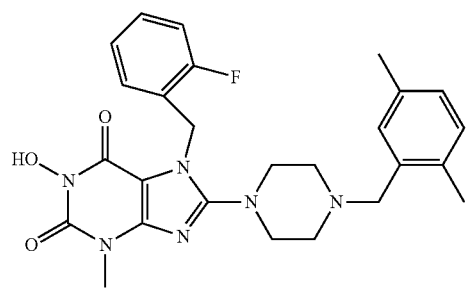

In one aspect, compounds of type 1.5, and similar compounds, can be prepared according to reaction Scheme 3B above. Thus, compounds of type 3.2 can be prepared by a coupling reaction of an appropriate xanthine analog, e.g., 2.6 as shown above, and an appropriate halide, e.g., 1.7 as shown above. Appropriate xanthine analogs and appropriate halides are commercially available or prepared by methods known to one skilled in the art. The coupling reaction is carried out in the presence of an appropriate base, e.g., DIPEA, in an appropriate solvent, e.g., DMF, at an appropriate temperature, e.g., 80° C. Compounds of type 3.3 can be prepared by a coupling reaction of an appropriate halide, e.g., 3.2 as shown above, and an appropriate amine, e.g., 1.9 as shown above. Appropriate amines are commercially available or prepared by methods known to one skilled in the art. The coupling reaction is carried out in the presence of an appropriate base, e.g., TEA, in an appropriate solvent system, e.g., 2-methoxyethanol/H$_2$O (4:1), at an appropriate temperature, e.g., 130° C. Compounds of type 3.4 can be prepared by a coupling reaction of an appropriate amine, e.g., 3.3 as shown above, and a carboxylic acid, or alternatively by a Cope elimination using an oxidant, e.g., m-chloroperoxybenzoic acid. The reaction is carried out in the presence of an appropriate base, e.g., sodium hydride, in an appropriate solvent, e.g., tetrahydrofuran (THF). As can be appreciated by one skilled in the art, the above reaction provides an example of a generalized approach wherein compounds similar in structure to the specific reactants above (compounds similar to compounds of type 1.1, 1.2, 1.3, and 1.4), can be substituted in the reaction to provide substituted xanthine analogs similar to Formula 1.5.

4. Route IV

In one aspect, xanthine analogs can be prepared as shown below.

In one aspect, compounds of type 4.4, and similar compounds, can be prepared according to reaction Scheme 4B above. Thus, compounds of type 4.7 can be prepared by a coupling reaction of an appropriate amine, e.g., 4.5 as shown above, and an appropriate halide, e.g., 4.6 as shown above. Appropriate amines and appropriate halides are commercially available or prepared by methods known to one skilled in the art. The coupling reaction is carried out in the presence of an appropriate catalyst, e.g., tris(dibenzylideneacetone)dipalladium(0), an appropriate ligand, e.g., BrettPhos, and an appropriate base, e.g., potassium tert-butoxide, in an appropriate solvent, e.g., toluene, at an appropriate temperature, e.g., 80° C. Compounds of type 4.8 can be prepared by deprotection of an appropriate protected amine, e.g., 4.7 as shown above. The deprotection is carried out in the presence of an appropriate deprotecting agent, e.g., TFA, in an appropriate solvent, e.g., DCM. As can be appreciated by one skilled in the art, the above reaction provides an example of a generalized approach wherein compounds similar in structure to the specific reactants above (compounds similar to compounds of type 4.1, 4.2, and 4.3), can be substituted in the reaction to provide substituted analogs similar to Formula 4.4.

5. Route V

In one aspect, xanthine analogs can be prepared as shown below.

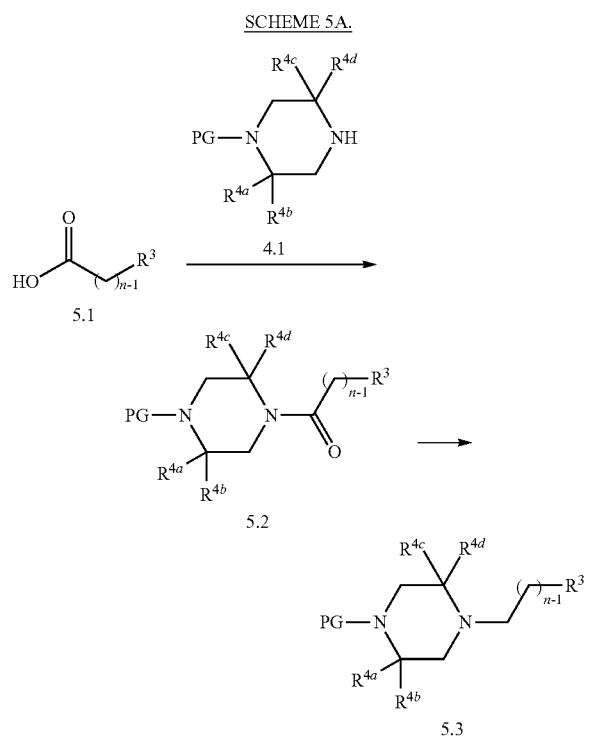

Compounds are represented in generic form, where PG is an amine protecting group and with substituents as noted in compound descriptions elsewhere herein. A more specific example is set forth below.

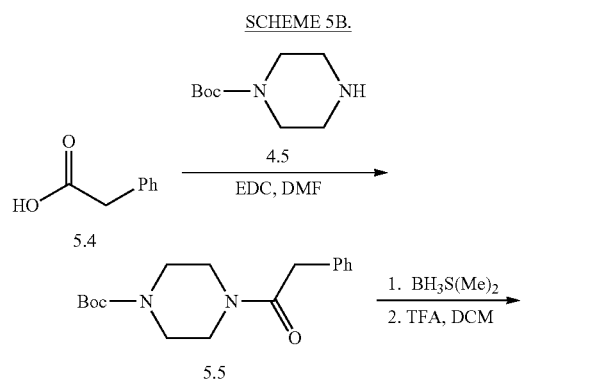

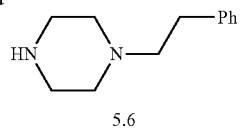

In one aspect, compounds of type 5.3, and similar compounds, can be prepared according to reaction Scheme 5B above. Thus, compounds of type 5.5 can be prepared by a coupling reaction of an appropriate carboxylic acid, e.g., 5.4 as shown above, and an appropriate amine, e.g., 4.5 as shown above. Appropriate carboxylic acids and appropriate amines are commercially available or prepared by methods known to one skilled in the art. The coupling reaction is carried out in the presence of an appropriate coupling agent, e.g., 1-ethyl-3-(3-dimethylaminopropyl)carbodiimide (EDC), in an appropriate solvent, e.g., DMF. Compounds of type 5.6 can be prepared by reduction of an appropriate amide, e.g., 5.5 as shown above, followed by deprotection of an appropriate protected amine. The reduction is carried out in the presence of an appropriate reducing agent, e.g., borane dimethylsulfide. The deprotection is carried out in the presence of an appropriate deprotecting agent, e.g., TFA, in an appropriate solvent, e.g., DCM. As can be appreciated by one skilled in the art, the above reaction provides an example of a generalized approach wherein compounds similar in structure to the specific reactants above (compounds similar to compounds of type 4.1, 5.1, and 5.2), can be substituted in the reaction to provide substituted analogs similar to Formula 5.3.

6. Route VI

In one aspect, xanthine analogs can be prepared as shown below.

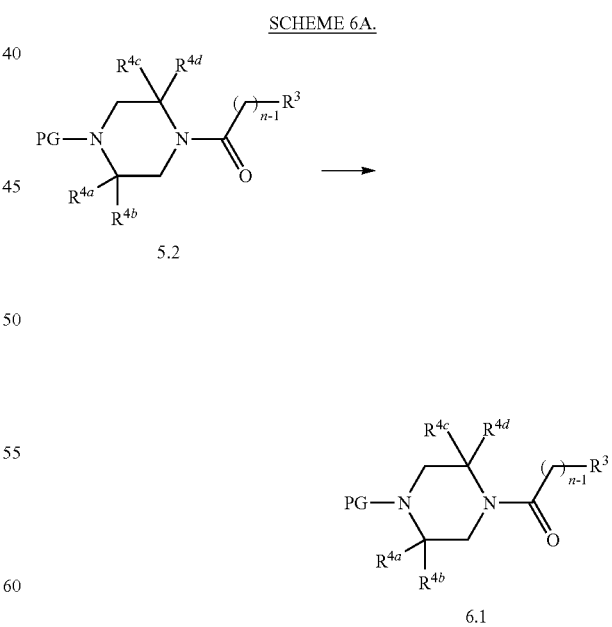

Compounds are represented in generic form, where PG is an amine protecting group and with substituents as noted in compound descriptions elsewhere herein. A more specific example is set forth below.

SCHEME 6B.

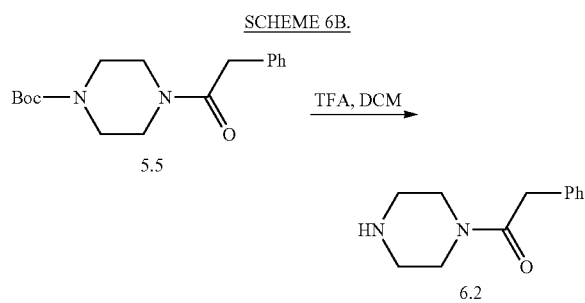

In one aspect, compounds of type 6.1, and similar compounds, can be prepared according to reaction Scheme 6B above. Thus, compounds of type 6.2 can be prepared by deprotection of an appropriate protected amine, e.g., 5.5 as shown above. The deprotection is carried out in the presence of an appropriate deprotecting agent, e.g., TFA, in an appropriate solvent, e.g., DCM. As can be appreciated by one skilled in the art, the above reaction provides an example of a generalized approach wherein compounds similar in structure to the specific reactants above (compounds similar to compounds of type 5.2), can be substituted in the reaction to provide substituted analogs similar to Formula 6.1.

E. Methods of Using the Compounds

The compounds and pharmaceutical compositions of the invention are useful in treating or controlling West Nile virus. To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of West Nile virus.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disease or condition.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling West Nile virus. Thus, provided is a method comprising administering a therapeutically effective amount of a composition comprising a disclosed compound to a subject.

a. Treating West Nile Virus

In one aspect, disclosed are methods of treating West Nile virus in a subject, the method comprising the step of administering to the subject an effective amount of at least one disclosed compound, or a pharmaceutically acceptable salt thereof.

In one aspect, disclosed are methods for treating West Nile virus (WNV) in a subject, the method comprising administering to the subject an effective amount of at least one compound having a structure represented by a formula:

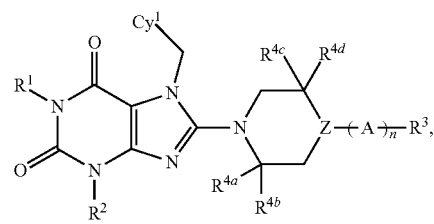

wherein n is selected from 0, 1, and 2; wherein each occurrence of A, when present, is individually selected from —C(O)— and —CH$_2$—, provided that no more than one occurrence of A, when present, is —C(O)—; wherein Z is selected from N and CR$^{10}$; wherein R$^{10}$, when present, is selected from hydrogen and C1-C4 alkyl; wherein R$^1$ is selected from hydrogen, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^2$ is selected from —OH, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C-C4 alkyl)-OH; wherein R$^3$ is selected from C1-C4 alkyl and Ar$^1$; wherein Ar$^1$, when present, is selected from 6-membered aryl and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl); and wherein each of R$^{4a}$, R$^{4b}$, R$^{4c}$, and R$^{4d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, —CO$_2$H, and —CO$_2$(C1-C4 alkyl); wherein Cy$^1$ is selected from cyclohexyl, 6-membered aryl, and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl), provided that when n is 1, A is CH$_2$, R$^1$ is hydrogen or methyl, R$^2$ is methyl, R$^3$ is 6-membered aryl, and Cy$^1$ is 6-membered aryl, then R$^1$, when present, is C1-C4 alkyl, or a pharmaceutically acceptable salt thereof, thereby treating West Nile virus.

In a further aspect, the subject has been diagnosed with a need for treatment of West Nile virus prior to the administering step.

In a further aspect, the subject is a mammal. In a still further aspect, the mammal is a human.

In a further aspect, the method further comprises the step of identifying a subject in need of treatment of West Nile virus.

In a further aspect, the method further comprises the step of administering a therapeutically effective amount of at least one antiviral agent. Examples of antiviral agents include, but are not limited to, acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, zinc salts, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

2. Use of Compounds

In one aspect, the invention relates to the use of a disclosed compound or a product of a disclosed method. In a further aspect, a use relates to the manufacture of a medicament for the treatment of West Nile virus in a mammal.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a viral infection in a mammal. In one aspect, the use is characterized in that the mammal is a human. In one aspect, the use is characterized in that the viral infection is West Nile virus.

In a further aspect, the use relates to the manufacture of a medicament for the treatment of West Nile virus in a mammal.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of West Nile virus in a mammal.

3. Manufacture of a Medicament

In one aspect, the invention relates to a method for the manufacture of a medicament for treating West Nile virus in a mammal, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in treatment of West Nile virus. The dose administered to an animal, particularly a human, in the context of the present invention should be sufficient to affect a therapeutic response in the animal over a reasonable timeframe. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

4. Kits

In one aspect, disclosed are kits comprising a compound having a structure represented by a formula:

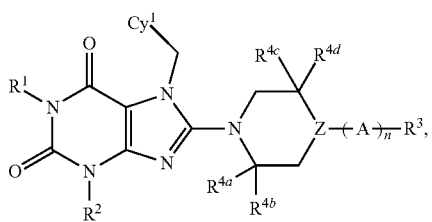

wherein n is selected from 0, 1, and 2; wherein each occurrence of A, when present, is individually selected from —C(O)— and —CH$_2$—, provided that no more than one occurrence of A, when present, is —C(O)—; wherein Z is selected from N and CR$^{10}$; wherein R$^{10}$, when present, is selected from hydrogen and C1-C4 alkyl; wherein R$^1$ is selected from hydrogen, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^2$ is selected from —OH, C1-C4 alkyl, C1-C4 cyanoalkyl, C1-C4 hydroxyalkyl, C1-C4 alkoxy, C3-C6 cycloalkyl, —CH$_2$(C3-C6 cycloalkyl), —(C1-C4 alkyl)-CO$_2$H, and —(C1-C4 alkyl)-O—(C1-C4 alkyl)-OH; wherein R$^3$ is selected from C1-C4 alkyl and Ar$^1$; wherein Ar$^1$, when present, is selected from 6-membered aryl and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl); and wherein each of R$^{4a}$, R$^{4b}$, R$^{4c}$, and R$^{4d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, —CO$_2$H, and —CO$_2$(C1-C4 alkyl); wherein Cy$^1$ is selected from cyclohexyl, 6-membered aryl, and 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and —CO$_2$(C1-C4 alkyl), provided that when n is 1, A is CH$_2$, R$^1$ is hydrogen or methyl, R$^2$ is methyl, R$^3$ is 6-membered aryl, and Cy$^1$ is 6-membered aryl, then R$^1$, when present, is C1-C4 alkyl, and provided that when n is 0, R$^1$ is hydrogen, R$^2$ is methyl, R$^3$ is 6-membered aryl, and Cy$^1$ is 6-membered aryl, then Z is CR$^{10}$, or a pharmaceutically acceptable salt thereof, and one or more of: (a) at least one antiviral agent; (b) instructions for administering the compound in connection with treating West Nile virus; (c) instructions for administering the compound in connection with reducing the risk of viral infection; and (d) instructions for treating West Nile virus.

Examples of antiviral agents include, but are not limited to, acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, zinc salts, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the at least one compound and the at least one agent are co-formulated. In a further aspect, the at least one compound and the at least one agent are co-packaged.

In a further aspect, the compound and the agent are administered sequentially. In a still further aspect, the compound and the agent are administered simultaneously.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. Examples

The following preparations and examples are given to enable those skilled in the art to more clearly understand and to practice the present invention. They should not be considered as limiting the scope of the invention, but merely as being illustrative and representative.

1. General Experimental Method

The reactions were performed under a dry argon atmosphere and reaction temperatures were measured externally. Anhydrous solvents over molecular sieves were purchased from Aldrich and used as such in reactions. Microwave (MW) reactions were performed in CEM Discover Labmate System with Intelligent Technology for Focused™ Microwave Synthesizer (Explorer 48). The reactions were monitored by thin-layer chromatography (TLC) on pre-coated silica gel (60F$_{254}$) aluminium plates (0.25 mm) from E. Merck and visualized using UV light (254 nm). Purification of compounds was performed on an Isco Teledyne Combiflash Rf200. Universal RediSep solid sample loading pre-packed cartridges (5.0 g silica) were used to absorb crude product and purified on 12 g silica RediSep Rf Gold Silica (20-40 μm spherical silica) columns using appropriate solvent gradients. Pure samples were dried overnight under high vacuum before analyses. The high resolution electrospray ionization mass spectral data (HR-ESIMS) were obtained on an Agilent LC-MSTOF. $^{1}$H NMR spectra were recorded at 400 MHz on Agilent/Varian MR-400 spectrometer in CDCl$_3$, CD$_3$OD, or DMSO-d$_6$ as solvents. The chemical shifts (δ) are in ppm downfield from standard tetramethylsilane (TMS). HPLC of final compounds were run on an Agilent 1100 LC equipped with a diode array UV detector and were monitored at 254 nm using the following using Sunfire C18 column (5 μm, 4.6×150 mm) using H$_2$O—CH$_3$CN (both containing 0.1% formic acid) 5-95% in 20 min with flow rate 1.0 mL/min.

2. Chemistry Experimentals a. 8-(4-(2,5-dimethylbenzyl)piperazin-1-yl)-7-(2-fluorobenzyl)-3-methyl-3,7-dihydro-1H-purine-2,6-dione (1)

Purchased from Life Chemicals (Catalog #F2636-0323). $^{1}$H NMR (400 MHz, DMSO-d$_6$) δ 10.86 (s, 1H), 7.29 (q, J=6.6, 5.8 Hz, 1H), 7.20-7.14 (m, 1H), 7.10 (t, J=7.5 Hz, 1H), 6.97 (s, 2H), 6.92 (t, J=8.5 Hz, 2H), 5.33 (s, 2H), 3.34 (s, 2H), 3.10-3.06 (m, 5H), 2.37-2.33 (m, 5H), 2.20 (d, J=5.3 Hz, 7H). HR-ESIMS: m/z 477.2408 [M+H]$^+$ calcd. for C$_{26}$H$_{30}$FN$_6$O$_2$, found 477.2398. HPLC Purity: 95% (Retention Time=16.4 min).

b. Synthesis of 8-(4-(2,5-dimethylbenzyl)piperazin-1-yl)-7-(2-fluorobenzyl)-1,3-dimethyl-3,7-dihydro-1H-purine-2,6-dione (2)

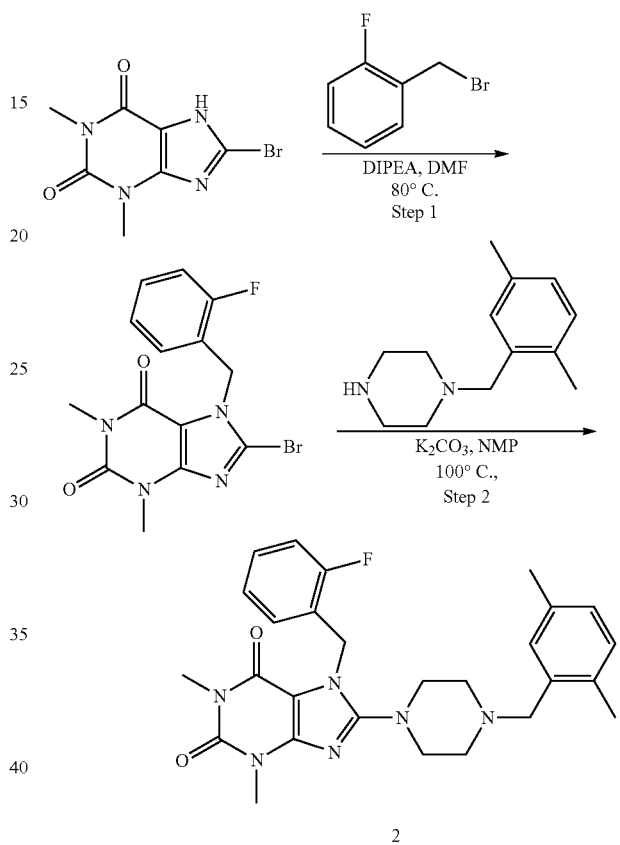

i. Step-1: Preparation of 8-bromo-7-(2-fluorobenzyl)-1,3-dimethyl-1H-purine-2,6(3H,7H)-dione A solution of 8-bromo-1,3-dimethyl-1H-purine-2,6(3H,7H)-dione (155 mg, 0.60 mmol), 1-(bromomethyl)-2-fluorobenzene (0.072 mL, 0.60 mmol), and DIPEA (0.12 mL, 0.66 mmol) in DMF (1 mL) was heated at 80° C. with stirring for 4 h. After cooling to ambient temperature, ice-cold water was added. The precipitate was collected by filtration, washed with cold water, and dried under high vacuum to give the desired compound (190 mg, 86%). $^{1}$H NMR (400 MHz, DMSO-d$_6$) δ 7.38 (dddd, J=8.3, 7.3, 5.5, 1.7 Hz, 1H), 7.26 (ddd, J=10.6, 8.3, 1.2 Hz, 1H), 7.15 (td, J=7.5, 1.2 Hz, 1H), 6.99-6.92 (m, 1H), 5.59 (s, 2H), 3.42 (s, 3H), 3.20 (s, 3H).

ii. Step-2: Preparation of 8-(4-(2,5-dimethylbenzyl)piperazin-1-yl)-7-(2-fluorobenzyl)-1,3-dimethyl-3,7-dihydro-1H-purine-2,6-dione (2)

A mixture of 8-bromo-7-(2-fluorobenzyl)-1,3-dimethyl-1H-purine-2,6(3H,7H)-dione (73.4 mg, 0.20 mmol) from Step-1, 1-(2,5-dimethylbenzyl)piperazine, TFA (40.9 mg, 0.20 mmol), and K$_2$CO$_3$ (55.3 mg, 0.40 mmol) in DMF (2 mL) was heated at 100° C. with stirring overnight. The reaction was cooled to room temperature and diluted with DCM (5 mL). The organic layer was separated, washed with brine (5 mL), dried over anhydrous Na$_2$SO$_4$, filtered, and concentrated in vacuo. The resulting product was purified via flash chromatography (0-15% EtOAc/hexanes) to give the desired compound 2 as a light yellow solid. Yield: 43 mg (44%). $^1$H NMR (400 MHz, DMSO-d$_6$) δ 7.37-7.30 (m, 1H), 7.22 (ddd, J=10.6, 8.3, 1.2 Hz, 1H), 7.13 (td, J=7.5, 1.2 Hz, 1H), 7.02 (d, J=7.7 Hz, 2H), 6.99-6.93 (m, 2H), 5.41 (s, 2H), 3.40 (s, 3H), 3.38 (s, 2H), 3.15 (d, J=6.8 Hz, 7H), 2.40 (t, J=4.8 Hz, 4H), 2.24 (d, J=5.7 Hz, 6H). HR-ESIMS: m/z 491.2565 [M+H]$^+$ calcd. for C$_{27}$H$_{32}$FN$_6$O$_2$, found 491.2561. HPLC Purity: 97% (Retention Time=11.1 min).

c. Synthesis of 8-(4-(2,5-dimethylbenzyl)piperazin-1-yl)-1-(2-fluorobenzyl)-3-methyl-3,7-dihydro-1H-purine-2,6-dione (3)

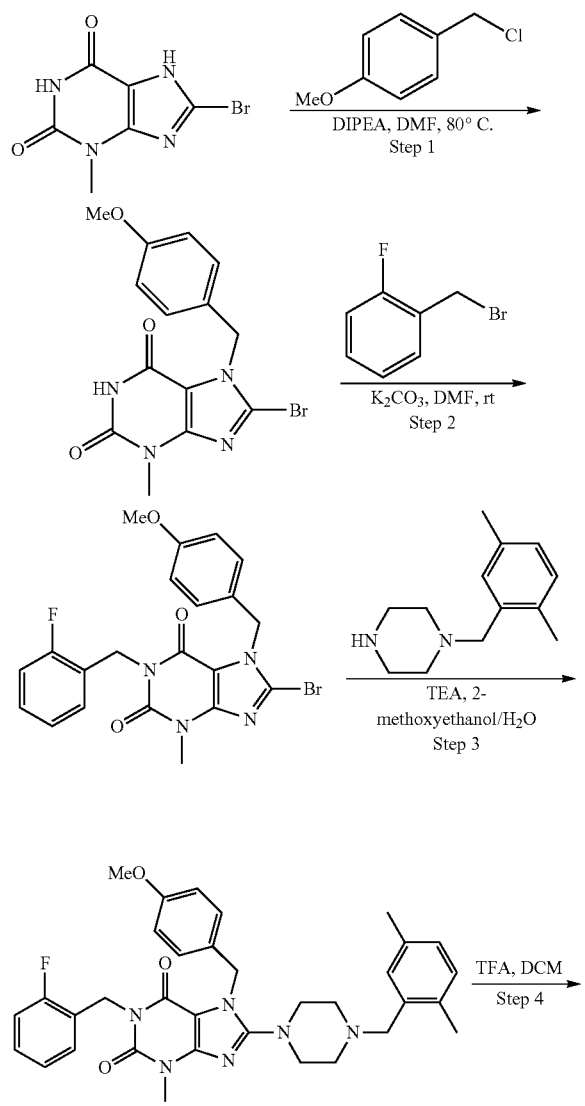

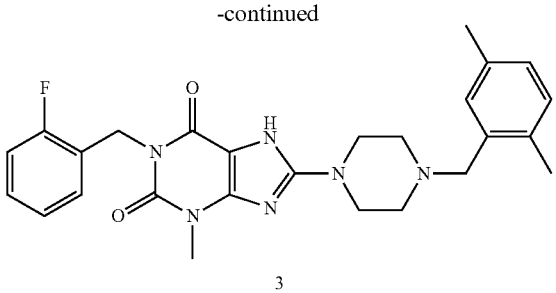

i. Step-1: Preparation of 8-bromo-7-(4-methoxybenzyl)-3-methyl-1H-purine-2,6(3H,7H)-dione To a solution of 8-bromo-3-methyl-1H-purine-2,6(3H,7H)-dione (245 mg, 1.0 mmol) in DMF (2 mL) was added 1-(chloromethyl)-4-methoxybenzene (157 mg, 1.0 mmol) and DIPEA (0.19 mL, 1.1 mmol). The reaction was heated at 80° C. and stirred for 2.5 h. The yellow reaction mixture was cooled to room temperature and cold water was added. The off-white solid was filtered off, washed with cold water, and dried under high vacuum to give the desired compound (310 mg, 85%). $^1$H NMR (400 MHz, DMSO-d$_6$) δ 11.33 (s, 1H), 7.29-7.19 (m, 2H), 6.96-6.83 (m, 2H), 5.39 (s, 2H), 3.72 (s, 3H), 3.32 (s, 3H).

ii. Step-2: Preparation of 8-bromo-1-(2-fluorobenzyl)-7-(4-methoxybenzyl)-3-methyl-3,7-dihydro-1H-purine-2,6-dione To a solution of 8-bromo-7-(4-methoxybenzyl)-3-methyl-1H-purine-2,6(3H,7H)-dione (300 mg, 0.82 mmol) from Step-1, in DMF (2.5 mL) was added K$_2$CO$_3$ (227 mg, 1.6 mmol) and 1-(bromomethyl)-2-fluorobenzene (0.1 mL, 0.82 mmol). The mixture was stirred at room temperature for 16 h. The reaction was then diluted with DCM (5 mL), washed with brine (5 mL), dried over anhydrous Na$_2$SO$_4$, filtered, and concentrated in vacuo to give the desired compound (345 mg, 89%). $^1$H NMR (400 MHz, CDCl$_3$) δ 7.42-7.35 (m, 2H), 7.25-7.17 (m, 2H), 7.09-7.00 (m, 2H), 6.89-6.81 (m, 2H), 5.49 (s, 2H), 5.29 (s, 2H), 3.79 (s, 3H), 3.54 (s, 3H).

iii. Step-3: Preparation of 8-(4-(2,5-dimethylbenzyl)piperazin-1-yl)-1-(2-fluorobenzyl)-7-(4-methoxybenzyl)-3-methyl-3,7-dihydro-1H-purine-2,6-dione A solution of 8-bromo-1-(2-fluorobenzyl)-7-(4-methoxybenzyl)-3-methyl-1H-purine-2,6(3H,7H)-dione (189 mg, 0.4 mmol) from Step-2, 1-(2,5-dimethylbenzyl)piperazine, TFA (172 mg, 0.84 mmol), and TEA (0.19 ml, 1.4 mmol) in 2-methoxyethanol/H$_2$O (4:1, 2.5 mL) was heated at 130° C. for 18 h. The reaction was cooled to room temperature, diluted with saturated aqueous NaHCO$_3$ (5 mL), and extracted with DCM (3×5 mL). The organic layers were washed with brine (10 mL), dried over Na$_2$SO$_4$, filtered, and concentrated in vacuo. The crude was purified via flash chromatography (0-30% EtOAc/hexanes) to give the desired compound (130 mg, 55%) as a white solid. $^1$H NMR (400 MHz, CDCl$_3$) δ 7.23-7.11 (m, 4H), 7.08-7.03 (m, 2H), 7.01 (dddd, J=8.2, 7.5, 4.0, 1.6 Hz, 3H), 6.85-6.80 (m, 2H), 5.29 (s, 2H), 5.27 (s, 2H), 3.78 (s, 3H), 3.52 (s, 3H), 3.48 (s, 2H), 3.25-3.17 (m, 4H), 2.58-2.51 (m, 4H), 2.33-2.29 (m, 6H).

iv. Step-4: Preparation of 8-(4-(2,5-dimethylbenzyl)piperazin-1-yl)-1-(2-fluorobenzyl)-3-methyl-3,7-dihydro-1H-purine-2,6-dione (3)

A solution of 8-(4-(2,5-dimethylbenzyl)piperazin-1-yl)-1-(2-fluorobenzyl)-7-(4-methoxybenzyl)-3-methyl-1H-purine-2,6(3H,7H)-dione (130 mg, 0.22 mmol) from Step-3 in 90% TFA/DCM (2.2 mL) was stirred at room temperature for 24 h. The excess solvent was removed and the crude was purified via flash chromatography (0-5% MeOH/DCM) to give the desired product 3 as a white solid. Yield: 42 mg (33%). $^1$H NMR (400 MHz, CDCl$_3$) δ 11.54 (s, 1H), 7.15-7.06 (m, 4H), 7.03-6.95 (m, 2H), 6.91-6.83 (m, 1H), 5.20 (s, 2H), 3.69 (s, 6H), 3.52 (s, 3H), 2.53 (d, J=60.8 Hz, 4H), 2.33 (s, 3H), 2.30 (s, 3H). HR-ESIMS: m/z 477.2409 [M+H]$^+$ calcd. for C$_{26}$H$_{30}$FN$_6$O$_2$, found 477.2400. HPLC Purity=100% (Retention Time=12.6 min).

d. Synthesis of Compounds 4, 5, 6, and 36

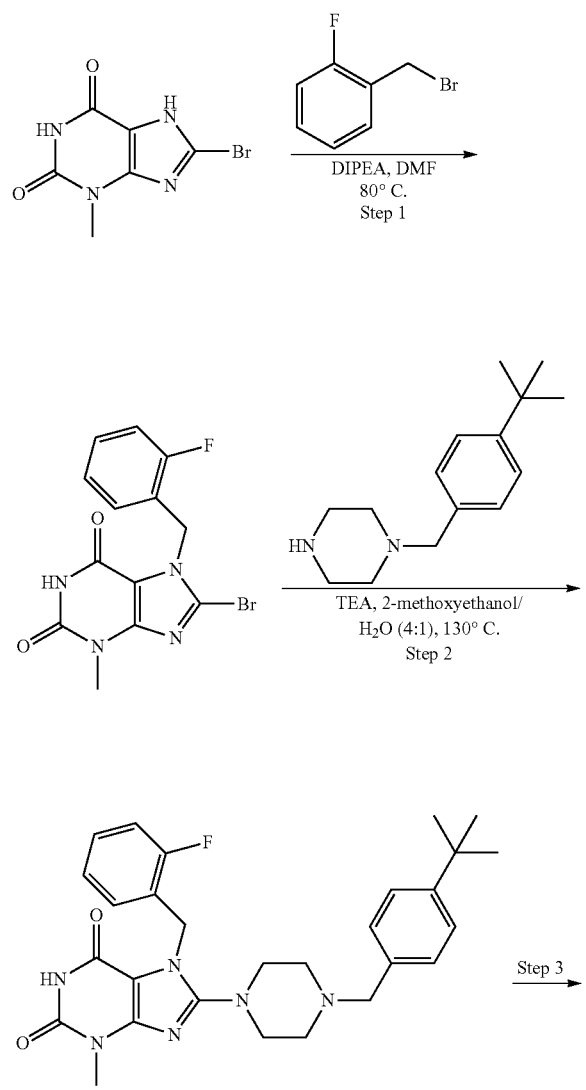

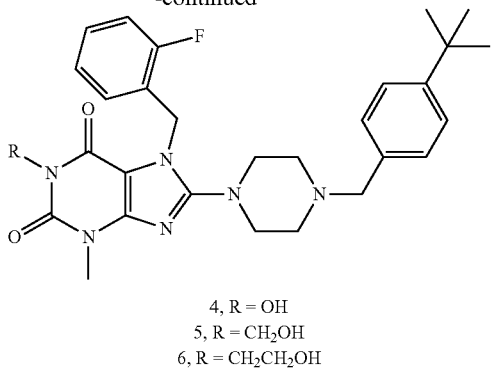

4, R = OH
5, R = CH$_2$OH
6, R = CH$_2$CH$_2$OH i. Step-1: Preparation of 8-bromo-7-(2-fluorobenzyl)-3-methyl-3,7-dihydro-1H-purine-2,6-dione A solution of 8-bromo-3-methyl-1H-purine-2,6(3H,7H)-dione (1 g, 4.1 mmol), 1-(bromomethyl)-2-fluorobenzene (0.50 mL, 4.1 mmol), -and DIPEA (0.78 mL, 4.5 mmol) in DMF (7 mL) was heated at 80° C. with stirring for 4 h. After cooling to ambient temperature, ice-cold water was added. The precipitate was collected by filtration, washed with cold water, and dried under high vacuum to give the desired compound (1.3 g, 90%) as a white solid. $^1$H NMR (400 MHz, DMSO-d$_6$) δ 11.32 (s, 1H), 7.38 (dddd, J=8.2, 7.2, 5.4, 1.8 Hz, 1H), 7.26 (ddd, J=10.6, 8.3, 1.2 Hz, 1H), 7.16 (td, J=7.5, 1.2 Hz, 1H), 6.98 (td, J=7.7, 1.7 Hz, 1H), 5.54 (s, 2H), 3.34 (s, 3H).

ii. Step-2: Preparation of 8-(4-(4-(tert-butyl)benzyl)piperazin-1-yl)-7-(2-fluorobenzyl)-3-methyl-3,7-dihydro-1H-purine-2,6-dione (36)

A solution of 8-bromo-7-(2-fluorobenzyl)-3-methyl-1H-purine-2,6(3H,7H)-dione (706 mg, 2.0 mmol) from Step-1, 1-((4-tert-butylphenyl)methyl)piperazine (1.4 g, 4.0 mmol), and TEA (0.98 mL, 7.0 mmol) in 2-methoxyethanol:H$_2$O (4:1, 12.5 mL) was heated at 130° C. for 18 h. The reaction was cooled to room temperature, diluted with saturated aqueous NaHCO$_3$ (10 mL), and extracted with DCM (3×10 mL). The organic layers were washed with brine (15 mL), dried over Na$_2$SO$_4$, filtered, and concentrated in vacuo. The crude was purified via flash chromatography (0-5% MeOH/DCM) to give the desired compound 36 as a white solid. Yield: 723 mg (72%). $^1$H NMR (400 MHz, DMSO-d$_6$) δ 10.91 (s, 1H), 7.36-7.27 (m, 3H), 7.24-7.15 (m, 3H), 7.13 (td, J=7.5, 1.2 Hz, 1H), 6.98 (td, J=7.8, 1.7 Hz, 1H), 5.36 (s, 2H), 3.42 (s, 2H), 3.32 (s, 3H), 3.14 (t, J=4.8 Hz, 4H), 2.37 (t, J=4.8 Hz, 4H), 1.26 (s, 9H). HR-ESIMS: m/z 505.2722 (M+H)$^+$ calcd. for C$_{28}$H$_{34}$FN$_6$O$_2$, found 505.2722. HPLC Purity=96% (Retention Time=11.4 min).

iii. Step-3: Preparation of 8-(4-(4-(tert-butyl)benzyl)piperazin-1-yl)-7-(2-fluorobenzyl)-1-hydroxy-3-methyl-3,7-dihydro-1H-purine-2,6-dione (4)

To a solution of 8-(4-(4-(tert-Butyl)benzyl)piperazin-1-yl)-7-(2-fluorobenzyl)-3-methyl-3,7-dihydro-1H-purine-2,6-dione (76 mg, 0.15 mmol) from Step-2 in THF (5 mL) was added sodium hydride (29 mg, 0.75 mmol) at 0° C. The reaction mixture was warmed to room temperature over 1 h and then cooled to 0° C. followed by addition of m-chloroperoxybenzoic acid (78 mg, 0.45 mmol). The reaction mixture was warmed to room temperature and stirred overnight. After the reaction was quenched by adding H$_2$O (10 mL), the aqueous phase was acidified with 1N HCl to pH=7 and then extracted with EtOAc (3×10 mL). The combined organic layers were dried over Na$_2$SO$_4$, filtered, and concentrated in vacuo. The crude was purified via flash chromatography (0-9% MeOH/DCM) to give the desired product 4 as a white solid. Yield: 58 mg (74%). $^1$H NMR (400 MHz, DMSO-d$_6$) δ 11.06 (s, 1H), 7.51-7.45 (m, 2H), 7.41-7.35 (m, 2H), 7.33-7.25 (m, 1H), 7.15 (ddd, J=10.6, 8.3, 1.2 Hz, 1H), 7.09 (td, J=7.5, 1.2 Hz, 1H), 6.94 (td, J=7.8, 1.7 Hz, 1H), 5.38 (s, 2H), 4.29 (s, 2H), 3.72 (t, J=12.1 Hz, 2H), 3.38 (d, J=11.6 Hz, 2H), 3.32 (s, 3H), 3.21 (d, J=12.6 Hz, 2H), 2.72 (d, J=11.2 Hz, 2H), 1.29 (s, 9H). HR-ESIMS: m/z 521.2671 [M+H]$^+$ calcd. for C$_{28}$H$_{34}$FN$_6$O$_3$, found 521.2661. HPLC Purity=99% (Retention Time=11.7 min).

iv. Step-3: Preparation of 8-(4-(4-(tert-butyl)benzyl) piperazin-1-yl)-7-(2-fluorobenzyl)-1-(hydroxymethyl)-3-methyl-3,7-dihydro-1H-purine-2,6-dione (5)

A solution of 8-(4-(4-(tert-Butyl)benzyl)piperazin-1-yl)-7-(2-fluorobenzyl)-3-methyl-3,7-dihydro-1H-purine-2,6-dione (40 mg, 0.08 mmol) from Step-2 and 37% formaldehyde solution (1 mL) was heated in a sealed tube at 110° C. for 24 h. The solution was cooled to room temperature and extracted with DCM (3×3 mL). The organic layers were dried over anhydrous Na$_2$SO$_4$, filtered, and concentrated in vacuo. The crude was purified via flash chromatography (0-5% MeOH/DCM) to give the desired product 5 as a white solid. Yield: 33 mg (78%). $^1$H NMR (400 MHz, DMSO-d$_6$) δ 7.32 (q, J=6.8 Hz, 3H), 7.24-7.16 (m, 3H), 7.12 (t, J=7.7 Hz, 1H), 6.95 (t, J=7.6 Hz, 1H), 6.13 (s, 1H), 5.41 (s, 2H), 5.21 (d, J=7.2 Hz, 2H), 3.43 (s, 2H), 3.40 (s, 3H), 3.18 (s, 4H), 2.38 (s, 4H), 1.27 (s, 9H). HR-ESIMS: m/z 535.2827 [M+H]$^+$ calcd. for C$_{29}$H$_{36}$FN$_6$O$_3$, found 535.2810. HPLC Purity=99% (Retention Time=11.7 min).

v. Step-3: Preparation of 8-(4-(4-(tert-butyl)benzyl) piperazin-1-yl)-7-(2-fluorobenzyl)-1-(2-hydroxyethyl)-3-methyl-3,7-dihydro-1H-purine-2,6-dione (6)

To a solution of 8-(4-(4-(tert-Butyl)benzyl)piperazin-1-yl)-7-(2-fluorobenzyl)-3-methyl-3,7-dihydro-1H-purine-2,6-dione (151 mg, 0.30 mmol) from Step-2 in DMF (2 mL) was added potassium carbonate (83 mg, 0.60 mmol) and 2-bromoethanol (0.042 mL, 0.60 mmol). The mixture was heated at 70° C. and stirred overnight. The residue was diluted with DCM (5 mL), washed with brine (5 mL), dried over anhydrous Na$_2$SO$_4$, filtered, and concentrated in vacuo. The crude was purified via flash chromatography (0-5% MeOH/DCM) to give the desired product 6 as a white solid. Yield: 107 mg (65%). $^1$H NMR (400 MHz, DMSO-d$_6$) δ 7.36-7.28 (m, 3H), 7.23-7.16 (m, 3H), 7.12 (td, J=7.5, 1.2 Hz, 1H), 6.97 (td, J=7.7, 1.7 Hz, 1H), 5.40 (s, 2H), 4.70-4.65 (m, 1H), 3.89 (t, J=6.8 Hz, 2H), 3.48-3.44 (m, 2H), 3.43 (s, 2H), 3.39 (s, 3H), 3.15 (t, J=4.9 Hz, 4H), 2.38 (t, J=4.8 Hz, 4H), 1.26 (s, 9H). HR-ESIMS: m/z 549.2984 [M+H]$^+$ calcd. for C$_{30}$H$_{38}$FN$_6$O$_3$, found 549.2982. HPLC Purity=99% (Retention Time=11.7 min).

e. Synthesis of Compounds 7-17, 20-27, 29-35, 51-62

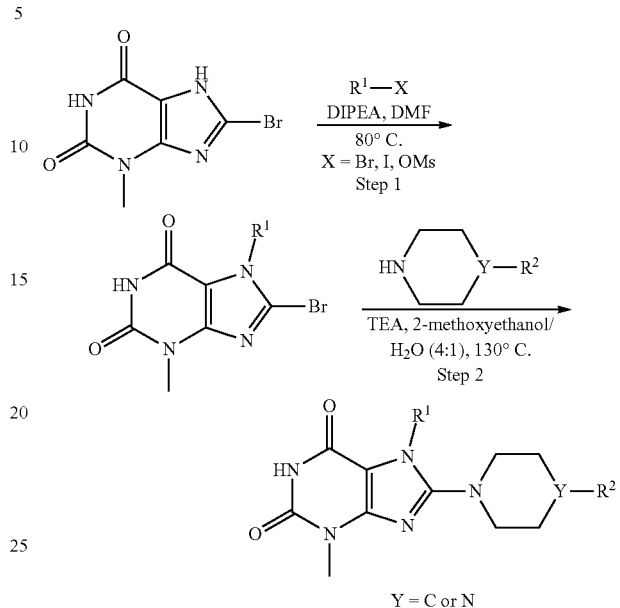

i. Step-1: General Procedure of N-7 Substitution of Purines

A solution of 8-bromopurine (1 equiv.), alkyl bromide/ benzyl bromide (1 equiv.), and DIPEA (1.1 equiv.) in DMF (0.6 M) was heated at 80° C. with stirring for 4 h. After cooling to ambient temperature, ice-cold water was added. The precipitate was separated by filtration, washed with cold water, and dried under high vacuum.

8-Bromo-7-ethyl-3-methyl-3,7-dihydro-1H-purine-2,6-dione. Following procedure above with 8-bromo-3-methyl-1H-purine-2,6(3H,7H)-dione (245 mg, 1.0 mmol), iodoethane (0.081 mL, 1.0 mmol), and DIPEA (0.19 mL, 1.1 mmol) in DMF (2 mL), the resulting product was dried under high vacuum to give the desired compound (160 mg, 59%). $^1$H NMR (400 MHz, DMSO-d$_6$) δ 11.25 (s, 1H), 4.24 (q, J=7.1 Hz, 2H), 3.31 (s, 3H), 1.30 (t, J=7.1 Hz, 3H).

8-Bromo-7-(cyclohexylmethyl)-3-methyl-3,7-dihydro-1H-purine-2,6-dione. Following procedure above with 8-bromo-3-methyl-1H-purine-2,6(3H,7H)-dione (245 mg, 1.0 mmol), (bromomethyl)cyclohexane (0.15 mL, 1.1 mmol), and DIPEA (0.19 mL, 1.1 mmol) in DMF (2 mL), the resulting product was dried under high vacuum to give the desired compound (227 mg, 67%). $^1$H NMR (400 MHz, DMSO-d$_6$) δ 11.25 (s, 1H), 4.04 (d, J=7.4 Hz, 2H), 3.31 (s, 3H), 1.83 (ddh, J=11.0, 7.5, 3.8 Hz, 1H), 1.66 (t, J=5.3 Hz, 2H), 1.60 (s, 1H), 1.51 (d, J=12.4 Hz, 2H), 1.12 (d, J=8.2 Hz, 3H), 1.01 (q, J=11.1 Hz, 2H).

8-Bromo-3-methyl-7-(pyridin-3-ylmethyl)-3,7-dihydro-1H-purine-2,6-dione. Following procedure above with 8-bromo-3-methyl-1H-purine-2,6(3H,7H)-dione (368 mg, 1.5 mmol), 3-(bromomethyl)pyridine, HBr (379 mg, 1.5 mmol), and DIPEA (0.55 mL, 3.1 mmol) in DMF (2 mL), the resulting product was dried under high vacuum to give the desired compound (412 mg, 86%). $^1$H NMR (400 MHz, DMSO-d$_6$) δ 11.35 (s, 1H), 8.57 (dd, J=2.4, 0.8 Hz, 1H), 8.53 (dd, J=4.8, 1.6 Hz, 1H), 7.66 (ddd, J=8.0, 2.4, 1.7 Hz, 1H), 7.39 (ddd, J=7.9, 4.8, 0.9 Hz, 1H), 5.52 (s, 2H), 3.32 (s, 3H).

2-((8-Bromo-3-methyl-2,6-dioxo-1,2,3,6-tetrahydro-7H-purin-7-yl)methyl)benzonitrile. Following procedure above with 8-bromo-3-methyl-1H-purine-2,6(3H,7H)-dione (368 mg, 1.5 mmol), 2-(bromomethyl)benzonitrile (294 mg, 1.5 mmol), and DIPEA (0.29 mL, 1.6 mmol) in DMF (3 mL), the resulting product was dried under high vacuum to give the desired compound (439 mg, 81%). $^1$H NMR (400 MHz, CDCl$_3$) δ 7.86 (s, 1H), 7.76-7.71 (m, 1H), 7.60-7.50 (m, 1H), 7.48-7.41 (m, 1H), 7.04-6.98 (m, 1H), 5.78 (s, 2H), 3.55 (s, 3H).

8-Bromo-3-methyl-7-(2-(trifluoromethyl)benzyl)-3,7-dihydro-1H-purine-2,6-dione. Following procedure above with 8-bromo-3-methyl-1H-purine-2,6(3H,7H)-dione (245 mg, 1.0 mmol), 1-(bromomethyl)-2-(trifluoromethyl)benzene (239 mg, 1.0 mmol), and DIPEA (0.19 mL, 1.1 mmol) in DMF (2 mL), the resulting product was dried under high vacuum to give the desired product (330 mg, 82%). $^1$H NMR (400 MHz, DMSO-d$_6$) δ 11.35 (s, 1H), 7.87-7.80 (m, 1H), 7.64-7.57 (m, 1H), 7.54 (dd, J=8.3, 6.9 Hz, 1H), 6.71 (d, J=7.7 Hz, 1H), 5.67 (s, 2H), 3.38 (s, 3H).

8-Bromo-7-(3-fluorobenzyl)-3-methyl-3,7-dihydro-1H-purine-2,6-dione. Following procedure above with 8-bromo-3-methyl-1H-purine-2,6(3H,7H)-dione (245 mg, 1.0 mmol), 1-(bromomethyl)-3-fluorobenzene (0.12 mL, 1.0 mmol), and DIPEA (0.19 mL, 1.1 mmol) in DMF (2 mL), the resulting product was dried under high vacuum to give the desired intermediate (300 mg, 85%). $^1$H NMR (400 MHz, DMSO-d$_6$) δ 11.35 (s, 1H), 7.41 (td, J=8.0, 6.1 Hz, 1H), 7.19-7.10 (m, 2H), 7.07 (dt, J=6.9, 1.0 Hz, 1H), 5.49 (s, 2H), 3.33 (s, 3H).

8-Bromo-7-(4-fluorobenzyl)-3-methyl-3,7-dihydro-1H-purine-2,6-dione. Following procedure above with 8-bromo-3-methyl-1H-purine-2,6(3H,7H)-dione (245 mg, 1.0 mmol), 1-(bromomethyl)-4-fluorobenzene (0.12 mL, 1.0 mmol), and DIPEA (0.19 mL, 1.1 mmol) in DMF (2 mL), the resulting product was dried under high vacuum to give the desired product (317 mg, 90%). $^1$H NMR (400 MHz, DMSO-d$_6$) δ 11.33 (s, 1H), 7.37-7.28 (m, 2H), 7.25-7.15 (m, 2H), 5.46 (s, 2H), 3.32 (s, 3H).

8-Bromo-7-(2,4-difluorobenzyl)-3-methyl-3,7-dihydro-1H-purine-2,6-dione. Following procedure above with 8-bromo-3-methyl-1H-purine-2,6(3H,7H)-dione (245 mg, 1.0 mmol), 1-(bromomethyl)-2, 4-fluorobenzene (0.13 mL, 1.0 mmol), and DIPEA (0.19 mL, 1.1 mmol) in DMF (2 mL), the resulting product was dried under high vacuum to give the desired product (300 mg, 81%). $^1$H NMR (400 MHz, DMSO-d$_6$) δ 11.34 (s, 1H), 7.32 (ddd, J=10.6, 9.3, 2.5 Hz, 1H), 7.13 (td, J=8.7, 6.5 Hz, 1H), 7.09-7.02 (m, 1H), 5.50 (s, 2H), 3.33 (s, 3H).

8-Bromo-3-methyl-7-(2-(trifluoromethoxy)benzyl)-3,7-dihydro-1H-purine-2,6-dione. Following procedure above with 8-bromo-3-methyl-1H-purine-2,6(3H,7H)-dione (300 mg, 1.2 mmol), 1-(bromomethyl)-2-(trifluoromethoxy)benzene (0.20 mL, 1.2 mmol), and DIPEA (0.24 mL, 1.4 mmol) in DMF (3 mL), the resulting product was dried under high vacuum to give the desired product (486 mg, 95%). $^1$H NMR (400 MHz, DMSO-d$_6$) δ 11.35 (s, 1H), 7.51-7.43 (m, 2H), 7.35 (ddd, J=7.7, 6.4, 2.2 Hz, 1H), 6.91-6.82 (m, 1H), 5.57 (s, 2H), 3.36 (s, 3H).

8-Bromo-7-((3-fluoropyridin-4-yl)methyl)-3-methyl-3,7-dihydro-1H-purine-2,6-dione. A solution of 8-bromo-3-methyl-1H-purine-2,6(3H,7H)-dione (454 mg, 1.8 mmol), (3-fluoro-4-pyridyl)methyl methanesulfonate (380 mg, 1.8 mmol), and DIPEA (0.32 mL, 1.8 mmol) in DMF (3 mL) was heated at 80° C. overnight. The reaction was cooled to room temperature and diluted with cold H$_2$O and extracted with EtOAc (3×10 mL). The organic layers were dried over anhydrous Na$_2$SO$_4$, filtered, and concentrated in vacuo. The crude was purified via flash chromatography (0-9% MeOH/DCM) to give the desired product (180 mg, 27%) as a white solid. $^1$H NMR (400 MHz, DMSO-d$_6$) δ 11.36 (s, 1H), 8.62 (d, J=1.7 Hz, 1H), 8.38 (dd, J=4.9, 1.0 Hz, 1H), 7.05-6.98 (m, 1H), 5.60 (s, 2H), 3.35 (s, 3H).

ii. Step-2: General Substitution Procedure to Synthesize 7-17, 20-27, 29-35, 51-62

A mixture of product from Step-1 (1.0 equiv.), 1-(2,5-dimethylbenzyl)piperazine or 1-(4-(tert-butyl)benzyl)piperazine (1.1 equiv.), and TEA (1.5-3 equiv.) in 2-methoxyethanol/H$_2$O (4:1, 0.25 M) was heated at 130° C. for 16 h. The reaction was cooled to room temperature, diluted with saturated aqueous NaHCO$_3$ (5 mL), and extracted with DCM (3×5 mL). Combined organic layers were washed with brine (5 mL), dried over anhydrous Na$_2$SO$_4$, filtered, and concentrated in vacuo. The crude product was purified on a pre-packed Silica gel column using Teledyne ISCO flash chromatographic system.

8-(4-(2,5-Dimethylbenzyl)piperazin-1-yl)-3-methyl-3,7-dihydro-1H-purine-2,6-dione (7). The resulting product was purified via flash chromatography (0-9% EtOAc/hexanes) to give the desired compound 7 as a white solid. Yield: 28 mg (25%). $^1$H NMR (400 MHz, DMSO-d$_6$) δ 11.73 (s, 1H), 10.66 (s, 1H), 7.08-7.01 (m, 2H), 7.01-6.94 (m, 1H), 3.45 (t, J=5.0 Hz, 4H), 3.42 (s, 2H), 3.28 (s, 3H), 2.43 (t, J=5.1 Hz, 4H), 2.27 (s, 3H), 2.25 (s, 3H). HR-ESIMS: m/z 369.2033 [M+H]$^+$ calcd. for C$_{19}$H$_{25}$N$_6$O$_2$, found 369.2027. HPLC Purity=100% (Retention Time=7.6 min).

8-(4-(2,5-Dimethylbenzyl)piperazin-1-yl)-7-ethyl-3-methyl-3,7-dihydro-1H-purine-2,6-dione (8). The resulting product was purified via flash chromatography (0-50% EtOAc/hexanes) to give the desired compound 8 as an ivory solid. Yield: 54 mg (54%). $^1$H NMR (400 MHz, DMSO-d$_6$) δ 10.89 (s, 1H), 7.05 (d, J=7.7 Hz, 2H), 6.97 (d, J=7.8 Hz, 1H), 4.03 (qd, J=7.0, 4.6 Hz, 2H), 3.45 (s, 2H), 3.29 (s, 3H), 3.18 (t, J=4.8 Hz, 4H), 2.52 (d, J=3.9 Hz, 4H), 2.29 (s, 3H), 2.25 (s, 3H), 1.32 (t, J=7.1 Hz, 3H). HR-ESIMS: m/z 397.2346 [M+H]$^+$ calcd. for C$_{21}$H$_{29}$N$_6$O$_2$, found 397.2348. HPLC Purity=100% (Retention Time=8.3 min).

7-(Cyclohexylmethyl)-8-(4-(2,5-dimethylbenzyl)piperazin-1-yl)-3-methyl-3,7-dihydro-1H-purine-2,6-dione (9). The resulting product was purified via flash chromatography (0-50% EtOAc/hexanes) to give the desired compound 9 as a white solid. Yield: 15 mg (13%). $^1$H NMR (400 MHz, CDCl$_3$) δ 7.71 (s, 1H), 7.06 (d, J=9.6 Hz, 2H), 7.02-6.98 (m, 1H), 3.92 (d, J=7.4 Hz, 2H), 3.50 (s, 2H), 3.48 (s, 3H), 3.25-3.18 (m, 4H), 2.61-2.53 (m, 4H), 2.34 (s, 3H), 2.31 (s, 3H), 1.89 (ddp, J=11.1, 7.3, 3.8 Hz, 1H), 1.74-1.60 (m, 3H), 1.45 (d, J=12.9 Hz, 2H), 1.18 (q, J=10.6, 9.7 Hz, 3H), 1.02-0.87 (m, 2H). HR-ESIMS: m/z 465.2972 [M+H]$^+$ calcd. for C$_{26}$H$_{37}$N$_6$O$_2$, found 465.2975. HPLC Purity=97% (Retention time=10.9 min).

8-(4-(2,5-Dimethylbenzyl)piperazin-1-yl)-3-methyl-7-(pyridin-3-ylmethyl)-3,7-dihydro-1H-purine-2,6-dione (10). The resulting product was purified via flash chromatography (0-5% MeOH/DCM) to give the desired compound 10 as a yellow solid. Yield: 30 mg (26%). $^1$H NMR (400 MHz, DMSO-d$_6$) δ 10.97 (s, 1H), 8.50-8.44 (m, 2H), 7.55 (dt, J=8.1, 2.0 Hz, 1H), 7.36 (ddd, J=7.9, 4.8, 0.9 Hz, 1H), 7.03 (d, J=6.7 Hz, 2H), 6.96 (d, J=7.7 Hz, 1H), 5.36 (s, 2H), 3.41 (s, 2H), 3.30 (s, 3H), 3.15 (s, 4H), 2.43 (s, 4H), 2.26 (s, 3H), 2.24 (s, 3H). HR-ESIMS: m/z 460.2455 [M+H]$^+$ calcd. for $C_{25}H_{30}N_7O_2$, found 460.2447. HPLC Purity=96% (Retention Time=6.9 min).

2-((8-(4-(2,5-Dimethylbenzyl)piperazin-1-yl)-3-methyl-2,6-dioxo-1,2,3,6-tetrahydro-7H-purin-7-yl)methyl)benzonitrile (11). The resulting product was purified via flash chromatography (0-50% EtOAc/hexanes) to give the desired compound 11 as a light yellow solid. Yield: 20 mg (16%). $^1$H NMR (400 MHz, DMSO-d$_6$) δ 10.91 (s, 1H), 7.87 (ddd, J=7.7, 1.4, 0.5 Hz, 1H), 7.64 (td, J=7.7, 1.4 Hz, 1H), 7.49 (td, J=7.7, 1.2 Hz, 1H), 7.08-6.92 (m, 4H), 5.50 (s, 2H), 3.37 (s, 2H), 3.33 (s, 3H), 3.11 (t, J=4.8 Hz, 4H), 2.39 (t, J=4.8 Hz, 4H), 2.24 (d, J=5.6 Hz, 6H). HR-ESIMS: m/z 484.2455 [M+H]$^+$ calcd. for $C_{27}H_{30}N_7O_2$, found 484.2453. HPLC Purity=97% (Retention Time=9.6 min).

8-(4-(2,5-Dimethylbenzyl)piperazin-1-yl)-3-methyl-7-(2-(trifluoromethyl)benzyl)-3,7-dihydro-1H-purine-2,6-dione (12). The resulting product was purified via flash chromatography (0-35% EtOAc/hexanes) to give the desired compound 12 as a white solid. Yield: 78 mg (59%). $^1$H NMR (400 MHz, DMSO-d$_6$) δ 10.94 (s, 1H), 7.79 (dt, J=7.8, 1.0 Hz, 1H), 7.61 (dd, J=8.2, 7.0 Hz, 1H), 7.51 (t, J=7.6 Hz, 1H), 7.03-6.96 (m, 2H), 6.96-6.88 (m, 2H), 5.47 (s, 2H), 3.35 (s, 3H), 3.34 (s, 2H), 3.05 (t, J=4.9 Hz, 4H), 2.33 (t, J=4.9 Hz, 4H), 2.22 (s, 6H). HR-ESIMS: m/z 527.2377 [M+H]$^+$ calcd. for $C_{27}H_{30}F_3N_6O_2$, found 527.2365. HPLC Purity=98% (Retention Time=10.5 min).

8-(4-(2,5-Dimethylbenzyl)piperazin-1-yl)-7-(3-fluorobenzyl)-3-methyl-3,7-dihydro-1H-purine-2,6-dione (13). The resulting product was purified via flash chromatography (0-35% EtOAc/hexanes) to give the desired compound 13 as a white solid. Yield: 62 mg (52%). $^1$H NMR (400 MHz, DMSO-d$_6$) δ 10.94 (s, 1H), 7.38 (td, J=8.0, 6.1 Hz, 1H), 7.16-7.06 (m, 1H), 7.05-6.92 (m, 5H), 5.33 (s, 2H), 3.40 (s, 2H), 3.31 (s, 3H), 3.13 (t, J=4.9 Hz, 4H), 2.41 (t, J=4.8 Hz, 4H), 2.25 (d, J=6.9 Hz, 6H). HR-ESIMS: m/z 477.2409 [M+H]$^+$ calcd. for $C_{26}H_{30}FN_6O_2$, found 477.2406. HPLC Purity=100% (Retention Time=10.0 min).

8-(4-(2,5-Dimethylbenzyl)piperazin-1-yl)-7-(4-fluorobenzyl)-3-methyl-3,7-dihydro-1H-purine-2,6-dione (14). The resulting product was purified via flash chromatography (0-35% EtOAc/hexanes) to give the desired compound 14 as a yellow solid. Yield: 25 mg (21%). $^1$H NMR (400 MHz, DMSO-d$_6$) δ 10.94 (s, 1H), 7.27-7.20 (m, 2H), 7.19-7.12 (m, 2H), 7.05-7.00 (m, 2H), 6.98-6.92 (m, 1H), 5.30 (s, 2H), 3.41 (s, 2H), 3.30 (s, 3H), 3.13 (t, J=4.9 Hz, 4H), 2.43 (dd, J=7.1, 2.4 Hz, 4H), 2.26 (s, 3H), 2.24 (s, 3H). HR-ESIMS: m/z 477.2409 [M+H]$^+$ calcd. for $C_{26}H_{30}FN_6O_2$, found 477.2401. HPLC Purity=100% (Retention Time=9.8 min).

7-(2,4-Difluorobenzyl)-8-(4-(2,5-dimethylbenzyl)piperazin-1-yl)-3-methyl-3,7-dihydro-1H-purine-2,6-dione (15). The resulting product was purified via flash chromatography (0-35% EtOAc/hexanes) to give the desired compound 15 as a white solid. Yield: 52 mg (41%). $^1$H NMR (400 MHz, DMSO-d$_6$) δ 10.93 (s, 1H), 7.31-7.22 (m, 1H), 7.13-7.00 (m, 4H), 6.95 (d, J=7.9 Hz, 1H), 5.33 (s, 2H), 3.39 (s, 2H), 3.31 (s, 3H), 3.13 (t, J=4.9 Hz, 4H), 2.41 (s, 4H), 2.25 (d, J=6.9 Hz, 6H). HR-ESIMS: m/z 495.2315 [M+H]$^+$ calcd. for $C_{26}H_{29}F_2N_6O_2$, found 495.2307. HPLC Purity=100% (Retention time=10.5 min).

8-(4-(4-(tert-Butyl)benzyl)piperazin-1-yl)-3-methyl-7-(2-(trifluoromethyl)benzyl)-3,7-dihydro-1H-purine-2,6-dione (16). The resulting product was purified via flash chromatography (0-50% EtOAc/hexanes) to give the desired compound 16 as a white solid. Yield: 71 mg (51%). $^1$H NMR (400 MHz, DMSO-d$_6$) δ 10.95 (s, 1H), 7.81-7.74 (m, 1H), 7.60 (dd, J=8.3, 6.9 Hz, 1H), 7.50 (t, J=7.6 Hz, 1H), 7.34-7.27 (m, 2H), 7.19-7.13 (m, 2H), 6.91 (d, J=7.9 Hz, 1H), 5.46 (s, 2H), 3.39 (s, 2H), 3.32 (s, 3H), 3.06 (t, J=4.8 Hz, 4H), 2.31 (t, J=4.7 Hz, 4H), 1.25 (s, 9H). HR-ESIMS: m/z 555.2689 (M+H)$^+$ calcd. for $C_{29}H_{34}F_3N_6O_2$, found 555.2689. HPLC Purity=100% (Retention Time=12.3 min).

8-(4-(4-(tert-Butyl)benzyl)piperazin-1-yl)-3-methyl-7-(2-(trifluoromethoxy)benzyl)-3,7-dihydro-1H-purine-2,6-dione (17). The resulting product was purified via flash chromatography (0-100% EtOAc/hexanes) to give the desired compound 17 as a white solid. Yield: 106 mg (74%). $^1$H NMR (400 MHz, DMSO-d$_6$) δ 10.91 (s, 1H), 7.40 (dddd, J=15.3, 8.3, 6.9, 1.7 Hz, 2H), 7.35-7.28 (m, 3H), 7.21-7.14 (m, 2H), 6.99 (dd, J=7.8, 1.5 Hz, 1H), 5.38 (s, 2H), 3.41 (s, 2H), 3.33 (s, 3H), 3.10 (t, J=4.9 Hz, 4H), 2.32 (d, J=5.4 Hz, 4H), 1.26 (s, 9H). HR-ESIMS: m/z 571.2639 (M+H)$^+$ calcd. for $C_{29}H_{34}F_3N_6O_3$, found 571.2635. HPLC Purity=95% (Retention Time=12.6 min).

8-(4-(4-(tert-Butyl)benzyl)piperazin-1-yl)-7-((3-fluoropyridin-4-yl)methyl)-3-methyl-3,7-dihydro-1H-purine-2,6-dione (20). The resulting product was purified via flash chromatography (0-5% MeOH/DCM) to give the desired compound 20 as a white solid. Yield: 136 mg (90%). $^1$H NMR (400 MHz, DMSO-d$_6$) δ 10.94 (s, 1H), 8.55 (d, J=1.7 Hz, 1H), 8.34 (dd, J=4.9, 1.0 Hz, 1H), 7.35-7.29 (m, 2H), 7.23-7.16 (m, 2H), 7.00 (dd, J=6.5, 4.9 Hz, 1H), 5.40 (s, 2H), 3.43 (s, 2H), 3.33 (s, 3H), 3.15 (t, J=4.8 Hz, 4H), 2.38 (t, J=4.6 Hz, 4H), 1.26 (s, 9H). HR-ESIMS: m/z 506.2674 (M+H)$^+$ calcd. for $C27H_{33}FN_7O_2$, found 506.2682. HPLC Purity=99% (Retention Time=9.7 min).

7-(2-Fluorobenzyl)-3-methyl-8-(piperazin-1-yl)-3,7-dihydro-1H-purine-2,6-dione (21). Following Step-2, with 8-bromo-7-(2-fluorobenzyl)-3-methyl-1H-purine-2,6(3H,7H)-dione (71 mg, 0.20 mmol), piperazine (21 mg, 0.24 mmol), and TEA (42 μL, 0.30 mmol) in 2-methoxyethanol:H$_2$O (4:1, 1 mL), the resulting product was purified via flash chromatography (0-5% MeOH/DCM) to give the desired compound 21 as a yellow-white solid. Yield: 35 mg (49%). $^1$H NMR (400 MHz, DMSO-d$_6$) δ 10.90 (s, 1H), 7.34 (tdd, J=7.4, 5.4, 1.7 Hz, 1H), 7.21 (ddd, J=10.6, 8.3, 1.2 Hz, 1H), 7.14 (td, J=7.5, 1.2 Hz, 1H), 6.99 (td, J=7.7, 1.7 Hz, 1H), 5.37 (s, 2H), 3.32 (s, 3H), 3.06-2.99 (m, 4H), 2.71-2.63 (m, 4H). HR-ESIMS: m/z 359.1626 (M+H)$^+$ calcd. for $C_{17}H_{20}FN_6O_2$, found 359.1624. HPLC Purity=99% (Retention Time=6.0 min).

7-(2-Fluorobenzyl)-3-methyl-8-morpholino-3,7-dihydro-1H-purine-2,6-dione (22). Following Step-2, with 8-bromo-7-(2-fluorobenzyl)-3-methyl-1H-purine-2,6(3H,7H)-dione (88 mg, 0.25 mmol), morpholine (26 μL, 0.24 mmol), and TEA (52 μL, 0.37 mmol) in 2-methoxyethanol:H$_2$O (4:1, 1 mL), the resulting product was purified via flash chromatography (0-5% MeOH/DCM) to give the desired compound 22 as a yellow-white solid. Yield: 56 mg (62%). $^1$H NMR (400 MHz, DMSO-d$_6$) δ 10.92 (s, 1H), 7.32 (dddd, J=8.3, 7.3, 5.4, 1.8 Hz, 1H), 7.20 (ddd, J=10.6, 8.3, 1.2 Hz, 1H), 7.13 (td, J=7.5, 1.2 Hz, 1H), 6.99 (td, J=7.7, 1.7 Hz, 1H), 5.38 (s, 2H), 3.61-3.57 (m, 4H), 3.31 (s, 3H), 3.11-3.07 (m, 4H). HR-ESIMS: m/z 360.1466 (M+H)$^+$ calcd. for $C_{17}H_{19}FN_5O_3$, found 360.1470. HPLC Purity=95% (Retention Time=9.4 min).

8-(4-Cyclopropylpiperazin-1-yl)-7-(2-fluorobenzyl)-3-methyl-3,7-dihydro-1H-purine-2,6-dione (23). Following Step-2, with 8-bromo-7-(2-fluorobenzyl)-3-methyl-1H-purine-2,6(3H,7H)-dione (88 mg, 0.25 mmol), 1-cyclopropylpiperazine (32 mg, 0.25 mmol), and K$_2$CO$_3$ (52 mg, 0.37 mmol) in DMF (2 mL), the resulting product was purified via flash chromatography (0-5% MeOH/DCM) to give the desired compound 23 as a white solid. Yield: 15 mg (15%).

¹H NMR (400 MHz, CDCl₃) δ 7.70 (s, 1H), 7.31-7.27 (m, 1H), 7.11-7.03 (m, 3H), 5.39 (s, 2H), 3.51 (d, J=0.6 Hz, 3H), 3.21-3.13 (m, 4H), 2.69-2.61 (m, 4H), 1.64 (tt, J=6.7, 3.7 Hz, 1H), 0.45 (dd, J=6.4, 4.1 Hz, 2H), 0.40 (t, J=3.8 Hz, 2H). HR-ESIMS: m/z 399.1939 (M+H)⁺ calcd. for $C_2H_{24}FN_6O_2$, found 399.1941. HPLC Purity=97% (Retention Time=6.9 min).

8-(4-(tert-Butyl)piperazin-1-yl)-7-(2-fluorobenzyl)-3-methyl-3,7-dihydro-1H-purine-2,6-dione (24). Following Step-2, with 8-bromo-7-(2-fluorobenzyl)-3-methyl-1H-purine-2,6(3H,7H)-dione (106 mg, 0.30 mmol), 1-(tert-butyl)piperazine (43 mg, 0.30 mmol), and K₂CO₃ (83 mg, 0.60 mmol) in DMF (2 mL), the resulting product was purified via flash chromatography (0-5% MeOH/DCM) to give the desired compound 24 as a white solid. Yield: 40 mg (32%). ¹H NMR (400 MHz, DMSO-d₆) δ 10.90 (s, 1H), 7.34 (tdd, J=7.6, 5.4, 1.8 Hz, 1H), 7.22 (ddd, J=10.6, 8.3, 1.2 Hz, 1H), 7.14 (td, J=7.5, 1.2 Hz, 1H), 6.98 (td, J=7.7, 1.7 Hz, 1H), 5.37 (s, 2H), 3.32 (s, 3H), 3.14-3.09 (m, 4H), 2.48 (d, J=4.7 Hz, 4H), 0.98 (s, 9H). HR-ESIMS: m/z 415.2252 (M+H)⁺ calcd. for $C_{21}H_{28}FN_6O_2$, found 415.2249. HPLC Purity=97% (Retention Time=7.3 min).

8-(4-Cyclobutylpiperazin-1-yl)-7-(2-fluorobenzyl)-3-methyl-3,7-dihydro-1H-purine-2,6-dione (25). A solution of 8-bromo-7-(2-fluorobenzyl)-3-methyl-1H-purine-2,6(3H,7H)-dione (88 mg, 0.25 mmol), 1-cyclobutylpiperazine (35 mg, 0.25 mmol), and K₂CO₃ (69 mg, 0.50 mmol) in NMP (2 mL) was irradiated at 110° C. under microwave conditions for 4 h. To the reaction mixture was added water (2 mL) and EtOAc (5 mL). The organic phase was separated and washed with water (3×3 mL). The organic layer was dried over Na₂SO₄, filtered, and concentrated in vacuo. The crude was purified via flash chromatography (0-5% MeOH/DCM) to give the desired compound 25 as a white solid. Yield: 48 mg (46%). ¹H NMR (400 MHz, DMSO-d₆) δ 10.92 (s, 1H), 7.37-7.28 (m, 1H), 7.21 (ddd, J=10.6, 8.3, 1.2 Hz, 1H), 7.14 (td, J=7.5, 1.2 Hz, 1H), 6.98 (td, J=7.8, 1.7 Hz, 1H), 5.36 (s, 2H), 3.32 (s, 3H), 3.12 (t, J=4.9 Hz, 4H), 2.68 (p, J=7.7 Hz, 1H), 2.28-2.19 (m, 4H), 1.92 (dq, J=9.5, 4.9 Hz, 2H), 1.74 (dt, J=10.3, 8.4 Hz, 2H), 1.61 (ddd, J=12.6, 9.1, 4.3 Hz, 2H). HR-ESIMS: m/z 413.2096 (M+H)⁺ calcd. for $C_{21}H_{26}FN_6O_2$, found 413.2095. HPLC Purity=99% (Retention Time=7.3 min).

8-(4-(2,5-Dimethylphenyl)piperazin-1-yl)-7-(2-fluorobenzyl)-3-methyl-3,7-dihydro-1H-purine-2,6-dione (26). Following Step-2, with 8-bromo-7-(2-fluorobenzyl)-3-methyl-1H-purine-2,6(3H,7H)-dione (88 mg, 0.25 mmol), 1-(2,5-dimethylphenyl)piperazine (48 mg, 0.25 mmol), and K₂CO₃ (52 mg, 0.37 mmol) in DMF (2 mL), the resulting product was purified via flash chromatography (0-5% MeOH/DCM) to give the desired compound 26 as a white-yellow solid. Yield: 35 mg (30%). ¹H NMR (400 MHz, CDCl₃) δ 7.99 (s, 1H), 7.31-7.27 (m, 1H), 7.14-7.04 (m, 4H), 6.83 (d, J=6.7 Hz, 2H), 5.45 (s, 2H), 3.53 (d, J=0.8 Hz, 3H), 3.36-3.29 (m, 4H), 2.96-2.92 (m, 4H), 2.31 (s, 3H), 2.24 (s, 3H). HR-ESIMS: m/z 463.2252 (M+H)⁺ calcd. for $C_{25}H_{28}FN_6O_2$, found 463.2248. HPLC Purity=96% (Retention Time=14.6 min).

8-(4-(3,5-Dimethylphenyl)piperazin-1-yl)-7-(2-fluorobenzyl)-3-methyl-3,7-dihydro-1H-purine-2,6-dione (27). Following Step-2, with 8-bromo-7-(2-fluorobenzyl)-3-methyl-1H-purine-2,6(3H,7H)-dione (88 mg, 0.25 mmol), 1-(3,5-dimethylphenyl)piperazine (71 mg, 0.37 mmol), and TEA (105 µL, 0.75 mmol) in 2-methoxyethanol:H₂O (4:1, 1.25 mL), the resulting product was purified via flash chromatography (0-5% MeOH/DCM) to give the desired compound 27 as a white solid. Yield: 62 mg (54%). ¹H NMR (400 MHz, DMSO-d₆) δ 10.95 (s, 1H), 7.34 (tdd, J=7.6, 5.3, 1.8 Hz, 1H), 7.22 (ddd, J=10.6, 8.3, 1.2 Hz, 1H), 7.15 (td, J=7.5, 1.2 Hz, 1H), 7.03 (td, J=7.7, 1.7 Hz, 1H), 6.57-6.52 (m, 2H), 6.46-6.43 (m, 1H), 5.42 (s, 2H), 3.34 (s, 3H), 3.25 (dd, J=6.7, 3.4 Hz, 4H), 3.15-3.10 (m, 4H), 2.19 (s, 6H). HR-ESIMS: m/z 463.2252 (M+H)⁺ calcd. for $C_{25}H_{28}FN_6O_2$, found 463.2246. HPLC Purity=97% (Retention Time=12.0 min).

8-(4-(4-(tert-Butyl)phenyl)piperazin-1-yl)-7-(2-fluorobenzyl)-3-methyl-3,7-dihydro-1H-purine-2,6-dione (29). Following Step-2, with 8-bromo-7-(2-fluorobenzyl)-3-methyl-1H-purine-2,6(3H,7H)-dione (106 mg, 0.30 mmol), 1-(4-tert-butylphenyl)piperazine (72 mg, 0.33 mmol), and TEA (63 µL, 0.45 mmol) in 2-methoxyethanol:H₂O (4:1, 1 mL), the resulting product was purified via flash chromatography (0-5% MeOH/DCM) to give the desired compound 29 as a white solid. Yield: 35 mg (24%). ¹H NMR (400 MHz, DMSO-d₆) δ 10.96 (s, 1H), 7.34 (d, J=7.2 Hz, 1H), 7.23 (d, J=8.9 Hz, 3H), 7.15 (t, J=7.6 Hz, 1H), 7.03 (t, J=7.3 Hz, 1H), 6.87 (d, J=8.9 Hz, 2H), 5.43 (s, 2H), 3.34 (s, 3H), 3.28 (dd, J=9.3, 4.9 Hz, 4H), 3.12 (d, J=5.4 Hz, 4H), 1.23 (s, 9H). HR-ESIMS: m/z 491.2565 (M+H)⁺ calcd. for $C_{27}H_{32}FN_6O_2$, found 491.2561. HPLC Purity=100% (Retention Time=13.9 min).

7-(2-Fluorobenzyl)-3-methyl-8-(4-(4-(trifluoromethyl)phenyl)piperazin-1-yl)-3,7-dihydro-1H-purine-2,6-dione (30). Following Step-2, with 8-bromo-7-(2-fluorobenzyl)-3-methyl-1H-purine-2,6(3H,7H)-dione (88 mg, 0.25 mmol), 1-(4-(trifluoromethyl)piperazine (58 mg, 0.25 mmol), and K₂CO₃ (69 mg, 0.50 mmol) in DMSO (2 mL) at 110° C., the resulting product was purified via flash chromatography (0-5% MeOH/DCM) to give the desired compound 30 as a yellow solid. Yield: 5 mg (4%). ¹H NMR (400 MHz, CDCl₃) δ 7.52-7.47 (m, 2H), 7.31-7.27 (m, 1H), 7.18-7.04 (m, 3H), 6.93 (d, J=8.6 Hz, 2H), 5.45 (s, 2H), 3.52 (s, 3H), 3.33 (s, 8H). HR-ESIMS: m/z 503.1813 (M+H)⁺ calcd. for $C_{24}H_{23}F_4N_6O_2$, found 503.1817. HPLC Purity=95% (Retention Time=15.7 min).

8-(4-(4-Chloro-2-fluorophenyl)piperazin-1-yl)-7-(2-fluorobenzyl)-3-methyl-3,7-dihydro-1H-purine-2,6-dione (31). Following Step-2, with 8-bromo-7-(2-fluorobenzyl)-3-methyl-1H-purine-2,6(3H,7H)-dione (88 mg, 0.25 mmol), 1-(4-chloro-2-fluorophenyl)piperazine (64 mg, 0.30 mmol), and TEA (70 µL, 0.50 mmol) in 2-methoxyethanol:H₂O (4:1, 1 mL), the resulting product was purified via flash chromatography (0-5% MeOH/DCM) to give the desired compound 31 as a white solid. Yield: 65 mg (53%). ¹H NMR (400 MHz, DMSO-d₆) δ 7.36-7.28 (m, 2H), 7.24-7.11 (m, 3H), 7.06-6.98 (m, 2H), 5.41 (s, 2H), 3.32 (s, 3H), 3.28 (t, J=4.9 Hz, 4H), 3.02 (t, J=4.9 Hz, 4H). HR-ESIMS: m/z 487.1455 (M+H)⁺ calcd. for $C_{23}H_{22}ClF_2N_6O_2$ found 487.1446. HPLC Purity=96% (Retention Time=15.5 min).

6-(4-(7-(2-Fluorobenzyl)-3-methyl-2,6-dioxo-2,3,6,7-tetrahydro-1H-purin-8-yl)piperazin-1-yl)nicotinonitrile (32). Following Step-2, with 8-bromo-7-(2-fluorobenzyl)-3-methyl-1H-purine-2,6(3H,7H)-dione (88 mg, 0.25 mmol), 6-(piperazin-1-yl)nicotinonitrile (57 mg, 0.30 mmol), and TEA (70 µL, 0.50 mmol) in 2-methoxyethanol:H₂O (4:1, 1 mL), the resulting product was purified via flash chromatography (0-5% MeOH/DCM) to give the desired compound 32 as a white solid. Yield: 74 mg (64%). ¹H NMR (400 MHz, CDCl₃) δ 8.41 (dd, J=2.3, 0.7 Hz, 1H), 8.09 (s, 1H), 7.64 (dd, J=9.0, 2.3 Hz, 1H), 7.33-7.26 (m, 1H), 7.16 (td, J=7.5, 1.9 Hz, 1H), 7.13-7.04 (m, 2H), 6.61 (dd, J=9.0, 0.8 Hz, 1H), 5.46 (s, 2H), 3.78-3.71 (m, 4H), 3.50 (d, J=0.4 Hz, 3H), 3.30-3.22 (m, 4H). HR-ESIMS: m/z 461.1844 (M+H)⁺ calcd. for $C_{23}H_{22}FN_8O_2$, found 461.1849. HPLC Purity=98% (Retention Time=12.2 min).

7-(2-Fluorobenzyl)-3-methyl-8-(4-(pyridin-2-yl)piperazin-1-yl)-3,7-dihydro-1H-purine-2,6-dione (33). Following Step-2, with 8-bromo-7-(2-fluorobenzyl)-3-methyl-1H-purine-2,6(3H,7H)-dione (88 mg, 0.25 mmol), 1-(pyridin-2-yl)piperazine (46 µL, 0.30 mmol), and TEA (70 µL, 0.50 mmol) in 2-methoxyethanol:H$_2$O (4:1, 1 mL), the resulting product was purified via flash chromatography (0-5% MeOH/DCM) to give the desired compound 33 as a white solid. Yield: 65 mg (60%). $^1$H NMR (400 MHz, CDCl$_3$) δ 8.19 (ddd, J=4.9, 2.0, 1.0 Hz, 1H), 8.01 (s, 1H), 7.50 (ddd, J=8.4, 7.2, 2.0 Hz, 1H), 7.31-7.26 (m, 1H), 7.16-7.03 (m, 3H), 6.69-6.63 (m, 2H), 5.45 (s, 2H), 3.62-3.56 (m, 4H), 3.52 (s, 3H), 3.32-3.26 (m, 4H). HR-ESIMS: m/z 436.1892 (M+H)$^+$ calcd. for $C_{22}H_{23}FN_7O_2$, found 436.1903. HPLC Purity=99% (Retention Time=7.6 min).

7-(2-Fluorobenzyl)-3-methyl-8-(4-(4-(trifluoromethyl)benzyl)piperazin-1-yl)-3,7-dihydro-1H-purine-2,6-dione (34). Following Step-2, with 8-bromo-7-(2-fluorobenzyl)-3-methyl-1H-purine-2,6(3H,7H)-dione (88 mg, 0.25 mmol), 1-(4-(trifluoromethyl)benzyl)piperazine (61 mg, 0.25 mmol), and K$_2$CO$_3$ (69 mg, 0.50 mmol) in DMSO (3 mL) at 110° C., the resulting product was purified via flash chromatography (0-5% MeOH/DCM) to give the desired compound 34 as a yellow solid. Yield: 15 mg (12%). $^1$H NMR (400 MHz, CDCl$_3$) δ 7.58-7.53 (m, 2H), 7.45-7.40 (m, 2H), 7.26-7.19 (m, 1H), 7.11-6.98 (m, 3H), 5.38 (s, 2H), 3.56 (s, 2H), 3.49 (s, 3H), 3.22-3.14 (m, 4H), 2.51-2.43 (m, 4H). HR-ESIMS: m/z 517.1969 (M+H)$^+$ calcd. for $C_{25}H_{25}F_4N_6O_2$, found 517.1974. HPLC Purity=98% (Retention Time=10.3 min).

7-(2-Fluorobenzyl)-8-(4-(4-fluorobenzyl)piperazin-1-yl)-3-methyl-3,7-dihydro-1H-purine-2,6-dione (35). Following Step-2, with 8-bromo-7-(2-fluorobenzyl)-3-methyl-1H-purine-2,6(3H,7H)-dione (88 mg, 0.25 mmol), 1-(4-fluorobenzyl)piperazine (49 mg, 0.25 mmol), and K$_2$CO$_3$ (69 mg, 0.50 mmol) in DMSO (3 mL) at 110° C., the resulting product was purified via flash chromatography (0-5% MeOH/DCM) to give the desired compound 35 as a white-yellow solid. Yield: 12 mg (10%). $^1$H NMR (400 MHz, CDCl$_3$) δ 8.16 (s, 1H), 7.26 (s, 4H), 7.10-7.03 (m, 3H), 7.03-6.95 (m, 2H), 5.38 (s, 2H), 3.50 (s, 3H), 3.48 (s, 2H), 3.23-3.17 (m, 4H), 2.46 (dd, J=6.2, 3.6 Hz, 4H). HR-ESIMS: m/z 467.2002 (M+H)$^+$ calcd. for $C_{24}H_{25}F_2N_6O_2$, found 467.2006. HPLC Purity=95% (Retention Time=8.9 min).

8-(3,3-Difluoropyrrolidin-1-yl)-7-(2-fluorobenzyl)-3-methyl-3,7-dihydro-1H-purine-2,6-dione (51). Following Step-2, with 8-bromo-7-(2-fluorobenzyl)-3-methyl-1H-purine-2,6(3H,7H)-dione (88 mg, 0.25 mmol), 3,3-difluoropyrrolidine HCl (40 mg, 0.27 mmol), and TEA (87 µL, 0.62 mmol) in 2-methoxyethanol:H$_2$O (4:1, 1 mL), the resulting product was purified via flash chromatography (0-50% EtOAc/hexanes) to give the desired compound 51 as a white solid. Yield: 10 mg (10%). $^1$H NMR (400 MHz, CDCl$_3$) δ 7.83 (s, 1H), 7.33-7.27 (m, 1H), 7.13-7.05 (m, 2H), 7.00 (td, J=7.9, 1.8 Hz, 1H), 5.52 (s, 2H), 3.82 (t, J=12.8 Hz, 2H), 3.71 (t, J=7.3 Hz, 2H), 3.49 (s, 3H), 2.44-2.31 (m, 2H). HR-ESIMS: m/z 380.1329 (M+H)$^+$ calcd. for $C_{17}H_{17}F_3N_5O_2$, found 380.1324. HPLC Purity=95% (Retention Time=11.5 min).

8-(4,4-Dimethylpiperidin-1-yl)-7-(2-fluorobenzyl)-3-methyl-3,7-dihydro-1H-purine-2,6-dione (52). Following Step-2, with 8-bromo-7-(2-fluorobenzyl)-3-methyl-1H-purine-2,6(3H,7H)-dione (106 mg, 0.30 mmol), 4,4-dimethylpiperidine HCl (49 mg, 0.33 mmol), and TEA (0.10 mL, 0.75 mmol) in 2-methoxyethanol:H$_2$O (4:1, 1 mL), the resulting product was purified via flash chromatography (0-50% EtOAc/hexanes) to give the desired compound 52 as a light-yellow solid. Yield: 26 mg (22%). $^1$H NMR (400 MHz, DMSO-d$_6$) δ 10.90 (s, 1H), 7.38-7.28 (m, 1H), 7.22 (ddd, J=10.6, 8.3, 1.2 Hz, 1H), 7.14 (td, J=7.5, 1.2 Hz, 1H), 6.98 (td, J=7.8, 1.7 Hz, 1H), 5.33 (s, 2H), 3.33 (s, 2H), 3.15-3.08 (m, 4H), 1.35-1.28 (m, 4H), 0.91 (s, 6H). HR-ESIMS: m/z 386.1987 (M+H)$^+$ calcd. for $C_2H_{25}FN_5O_2$, found 386.1994. HPLC Purity=99% (Retention Time=14.8 min).

8-(4,4-Difluoropiperidin-1-yl)-7-(2-fluorobenzyl)-3-methyl-3,7-dihydro-1H-purine-2,6-dione (53). Following Step-2, with 8-bromo-7-(2-fluorobenzyl)-3-methyl-1H-purine-2,6(3H,7H)-dione (88 mg, 0.25 mmol), 4,4-difluoropiperidine HCl (43 mg, 0.27 mmol), and TEA (87 µL, 0.62 mmol) in 2-methoxyethanol:H$_2$O (4:1, 1 mL), the resulting product was purified via flash chromatography (0-50% EtOAc/hexanes) to give the desired compound 53 as a white solid. Yield: 58 mg (59%). $^1$H NMR (400 MHz, DMSO-d$_6$) δ 10.96 (s, 1H), 7.37-7.29 (m, 1H), 7.22 (ddd, J=10.6, 8.2, 1.2 Hz, 1H), 7.15 (td, J=7.5, 1.2 Hz, 1H), 7.03 (td, J=7.7, 1.7 Hz, 1H), 5.40 (s, 2H), 3.33 (s, 3H), 3.26 (dd, J=6.7, 4.9 Hz, 4H), 2.04 (ddd, J=19.8, 13.7, 5.7 Hz, 4H). HR-ESIMS: m/z 394.1485 (M+H)$^+$ calcd. for $C_{18}H_{19}F_3N_5O_2$, found 394.1493. HPLC Purity=100% (Retention Time=12.3 min).

8-(4-(tert-Butyl)piperidin-1-yl)-7-(2-fluorobenzyl)-3-methyl-3,7-dihydro-1H-purine-2,6-dione (54). Following Step-2, with 8-bromo-7-(2-fluorobenzyl)-3-methyl-1H-purine-2,6(3H,7H)-dione (88 mg, 0.25 mmol), 4-(tert-butyl)piperidine HCl (44 mg, 0.25 mmol), and K$_2$CO$_3$ (86 mg, 0.62 mmol) in DMF (2 mL) for three days, the resulting product was purified via flash chromatography (0-50% EtOAc/hexanes) to give the desired compound 54 as a white solid. Yield: 67 mg (65%). $^1$H NMR (400 MHz, CDCl$_3$) δ 7.91 (s, 1H), 7.26-7.22 (m, 1H), 7.10-7.04 (m, 3H), 5.37 (s, 2H), 3.51 (s, 5H), 2.84 (td, J=12.5, 2.3 Hz, 2H), 1.67 (d, J=13.0 Hz, 2H), 1.32-1.21 (m, 2H), 1.11 (tt, J=12.1, 3.2 Hz, 1H), 0.85 (s, 9H). HR-ESIMS: m/z 414.2299 (M+H)$^+$ calcd. for $C_{22}H_{29}FN_5O_2$, found 414.2302. HPLC Purity=95% (Retention Time=16.7 min).

7-(2-Fluorobenzyl)-3-methyl-8-(4-(trifluoromethyl)piperidin-1-yl)-3,7-dihydro-1H-purine-2,6-dione (55). Following Step-2, with 8-bromo-7-(2-fluorobenzyl)-3-methyl-1H-purine-2,6(3H,7H)-dione (88 mg, 0.25 mmol), 4-(trifluoromethyl)piperidine (41 µL, 0.30 mmol), and TEA (52 µL, 0.37 mmol) in 2-methoxyethanol:H$_2$O (4:1, 1 mL), the resulting product was purified via flash chromatography (0-50% EtOAc/hexanes) to give the desired compound 55 as a white solid. Yield: 79 mg (74%). $^1$H NMR (400 MHz, DMSO-d$_6$) δ 10.92 (s, 1H), 7.35-7.27 (m, 1H), 7.20 (ddd, J=10.6, 8.3, 1.2 Hz, 1H), 7.12 (td, J=7.5, 1.2 Hz, 1H), 6.99 (td, J=7.7, 1.7 Hz, 1H), 5.36 (s, 2H), 3.44 (d, J=12.3 Hz, 2H), 3.31 (s, 3H), 2.91 (td, J=12.7, 2.4 Hz, 2H), 1.77 (d, J=12.4 Hz, 2H), 1.45 (qd, J=12.5, 4.1 Hz, 2H). HR-ESIMS: m/z 426.1547 (M+H)$^+$ calcd. for $C_{19}H_{20}F_4N_5O_2$, found 426.1549. HPLC Purity=99% (Retention Time=13.5 min).

7-(2-Fluorobenzyl)-3-methyl-8-(4-phenylpiperidin-1-yl)-3,7-dihydro-1H-purine-2,6-dione (56). Following Step-2, with 8-bromo-7-(2-fluorobenzyl)-3-methyl-1H-purine-2,6(3H,7H)-dione (88 mg, 0.25 mmol), 4-phenylpiperidine (48 mg, 0.30 mmol), and TEA (52 µL, 0.37 mmol) in 2-methoxyethanol:H$_2$O (4:1, 1 mL), the resulting product was purified via flash chromatography (0-50% EtOAc/hexanes) to give the desired compound 56 as a white solid. Yield: 40 mg (37%). $^1$H NMR (400 MHz, DMSO-d$_6$) δ 10.91 (s, 1H), 7.39-7.26 (m, 3H), 7.26-7.13 (m, 5H), 7.03 (td, J=7.7, 1.7 Hz, 1H), 5.40 (s, 2H), 3.53 (d, J=12.5 Hz, 2H), 3.34 (s, 3H), 3.01 (td, J=12.5, 2.5 Hz, 2H), 2.67 (ddt, J=12.0, 7.4, 3.7 Hz, 1H), 1.76 (d, J=12.1 Hz, 2H), 1.64 (qd, J=12.4, 3.9 Hz, 2H). HR-ESIMS: m/z 434.1986 (M+H)$^+$ calcd. for $C_{24}H_{25}FN_5O_2$, found 434.1984. HPLC Purity=99% (Retention Time=15.1 min).

7-(2-Fluorobenzyl)-8-(4-(3-fluorophenyl)piperidin-1-yl)-3-methyl-3,7-dihydro-1H-purine-2,6-dione (57). Following Step-2, with 8-bromo-7-(2-fluorobenzyl)-3-methyl-1H-purine-2,6(3H,7H)-dione (71 mg, 0.20 mmol), 4-(3-fluorophenyl)piperidine HCl (52 mg, 0.24 mmol), and TEA (84 μL, 0.60 mmol) in 2-methoxyethanol:H$_2$O (4:1, 1 mL), the resulting product was purified via flash chromatography (0-50% EtOAc/hexanes) to give the desired compound 57 as a white solid. Yield: 43 mg (48%). $^1$H NMR (400 MHz, DMSO-d$_6$) δ 10.91 (s, 1H), 7.38-7.30 (m, 2H), 7.23 (ddd, J=10.6, 8.3, 1.2 Hz, 1H), 7.16 (td, J=7.5, 1.2 Hz, 1H), 7.08-6.98 (m, 4H), 5.40 (s, 2H), 3.52 (d, J=12.6 Hz, 2H), 3.34 (s, 3H), 3.00 (td, J=12.5, 2.4 Hz, 2H), 2.73 (tt, J=12.0, 3.7 Hz, 1H), 1.81-1.74 (m, 2H), 1.64 (qd, J=12.5, 3.9 Hz, 2H). HR-ESIMS: m/z 452.1892 (M+H)$^+$ calcd. for $C_{24}H_{24}F_2N_5O_2$, found 452.1887. HPLC Purity=99% (Retention Time=15.2 min).

4-(1-(7-(2-Fluorobenzyl)-3-methyl-2,6-dioxo-2,3,6,7-tetrahydro-1H-purin-8-yl)piperidin-4-yl)benzonitrile (58). Following Step-2, with 8-bromo-7-(2-fluorobenzyl)-3-methyl-1H-purine-2,6(3H,7H)-dione (88 mg, 0.25 mmol), 4-(piperidin-4-yl)benzonitrile (56 mg, 0.30 mmol), and TEA (87 μL, 0.62 mmol) in 2-methoxyethanol:H$_2$O (4:1, 1 mL), the resulting product was purified via flash chromatography (0-70% EtOAc/hexanes) to give the desired compound 58 as a white solid. Yield: 36 mg (31%). $^1$H NMR (400 MHz, DMSO-d$_6$) δ 10.91 (s, 1H), 7.79-7.75 (m, 2H), 7.45-7.41 (m, 2H), 7.35 (dddd, J=8.2, 7.2, 5.4, 1.7 Hz, 1H), 7.23 (ddd, J=10.6, 8.3, 1.2 Hz, 1H), 7.16 (td, J=7.5, 1.2 Hz, 1H), 7.03 (td, J=7.7, 1.7 Hz, 1H), 5.40 (s, 2H), 3.57-3.49 (m, 2H), 3.34 (s, 3H), 3.01 (td, J=12.5, 2.5 Hz, 2H), 2.81 (tt, J=12.0, 3.7 Hz, 1H), 1.78 (dd, J=13.1, 3.5 Hz, 2H), 1.66 (qd, J=12.5, 4.0 Hz, 2H). HR-ESIMS: m/z 459.1939 (M+H)$^+$ calcd. for $C_{25}H_{24}FN_6O_2$, found 459.1932. HPLC Purity=98% (Retention Time=13.8 min).

4-((1-(7-(2-Fluorobenzyl)-3-methyl-2,6-dioxo-2,3,6,7-tetrahydro-1H-purin-8-yl)piperidin-4-yl)methyl)benzonitrile (59). Following Step-2, with 8-bromo-7-(2-fluorobenzyl)-3-methyl-1H-purine-2,6(3H,7H)-dione (88 mg, 0.25 mmol), 4-(piperidin-4-ylmethyl)benzonitrile hydrochloride (71 mg, 0.30 mmol), and TEA (0.14 mL, 1.0 mmol) in 2-methoxyethanol:H$_2$O (4:1, 1 mL), the resulting product was purified via flash chromatography (0-50% EtOAc/hexanes) to give the desired compound 59 as an ivory solid. Yield: 40 mg (34%). $^1$H NMR (400 MHz, DMSO-d$_6$) δ 10.89 (s, 1H), 7.76-7.71 (m, 2H), 7.41-7.36 (m, 2H), 7.34-7.29 (m, 1H), 7.21 (ddd, J=10.5, 8.3, 1.2 Hz, 1H), 7.13 (td, J=7.5, 1.2 Hz, 1H), 7.00-6.92 (m, 1H), 5.32 (s, 2H), 3.39 (d, J=12.5 Hz, 2H), 3.31 (s, 3H), 2.86-2.76 (m, 2H), 2.60 (d, J=7.1 Hz, 2H), 1.77-1.64 (m, 1H), 1.52 (d, J=12.8 Hz, 2H), 1.21 (qd, J=12.4, 3.9 Hz, 2H). HR-ESIMS: m/z 473.2096 (M+H)$^+$ calcd. for $C_{26}H_{26}FN_6O_2$, found 473.2096. HPLC Purity=94% (Retention Time=14.6 min).

7-(2-Fluorobenzyl)-8-(4-(4-fluorobenzyl)piperidin-1-yl)-3-methyl-3,7-dihydro-1H-purine-2,6-dione (60). Following Step-2, with 8-bromo-7-(2-fluorobenzyl)-3-methyl-1H-purine-2,6(3H,7H)-dione (88 mg, 0.25 mmol), 4-(4-fluorobenzyl)piperidine (56 μL, 0.30 mmol), and TEA (70 μL, 0.50 mmol) in 2-methoxyethanol:H$_2$O (4:1, 1 mL), the resulting product was purified via flash chromatography (0-50% EtOAc/hexanes) to give the desired compound 60 as an ivory solid. Yield: 85 mg (73%). $^1$H NMR (400 MHz, DMSO-d$_6$) δ 10.89 (s, 1H), 7.36-7.29 (m, 1H), 7.24-7.12 (m, 4H), 7.12-7.05 (m, 2H), 6.97 (td, J=7.7, 1.7 Hz, 1H), 5.33 (s, 2H), 3.38 (dd, J=13.0, 9.8 Hz, 2H), 3.31 (s, 3H), 2.80 (td, J=12.5, 2.4 Hz, 2H), 2.48 (d, J=6.9 Hz, 2H), 1.63 (ddt, J=11.1, 7.4, 3.7 Hz, 1H), 1.53 (dd, J=13.5, 3.4 Hz, 2H), 1.25-1.10 (m, 2H). HR-ESIMS: m/z 466.2049 (M+H)$^+$ calcd. for $C_{25}H_{26}F_2N_5O_2$, found 466.2045. HPLC Purity=98% (Retention Time=15.9 min).

8-(4-(3,5-Difluorobenzyl)piperidin-1-yl)-7-(2-fluorobenzyl)-3-methyl-3,7-dihydro-1H-purine-2,6-dione (61). Following Step-2, with 8-bromo-7-(2-fluorobenzyl)-3-methyl-1H-purine-2,6(3H,7H)-dione (88 mg, 0.25 mmol), 4-(3,5-difluorobenzyl)piperidine (63 mg, 0.30 mmol), and TEA (70 μL, 0.50 mmol) in 2-methoxyethanol:H$_2$O (4:1, 1 mL), the resulting product was purified via flash chromatography (0-50% EtOAc/hexanes) to give the desired compound 61 as an ivory solid. Yield: 78 mg (64%). $^1$H NMR (400 MHz, DMSO-d$_6$) δ 10.90 (s, 1H), 7.37-7.29 (m, 1H), 7.21 (ddd, J=10.6, 8.3, 1.2 Hz, 1H), 7.13 (td, J=7.5, 1.2 Hz, 1H), 7.03 (tt, J=9.5, 2.4 Hz, 1H), 6.99-6.91 (m, 3H), 5.33 (s, 2H), 3.40 (d, J=12.8 Hz, 2H), 3.31 (s, 3H), 2.89-2.76 (m, 2H), 2.54 (d, J=7.1 Hz, 2H), 1.71 (ddd, J=11.3, 7.5, 3.7 Hz, 1H), 1.53 (d, J=12.9 Hz, 2H), 1.26-1.16 (m, 2H). HR-ESIMS: m/z 484.1955 (M+H)$^+$ calcd. for $C_{25}H_{25}F_3N_5O_2$, found 484.1952. HPLC Purity=95% (Retention Time=16.3 min).

7-(2-Fluorobenzyl)-3-methyl-8-(4-(pyridin-3-ylmethyl)piperidin-1-yl)-3,7-dihydro-1H-purine-2,6-dione (62). Following Step-2, with 8-bromo-7-(2-fluorobenzyl)-3-methyl-1H-purine-2,6(3H,7H)-dione (88 mg, 0.25 mmol), 3-(piperidin-4-ylmethyl)pyridine (53 mg, 0.30 mmol), and TEA (87 μL, 0.62 mmol) in 2-methoxyethanol:H$_2$O (4:1, 1 mL), the resulting product was purified via flash chromatography (0-5% MeOH/DCM) to give the desired compound 62 as a light-tan solid. Yield: 70 mg (62%). $^1$H NMR (400 MHz, DMSO-d$_6$) δ 10.89 (s, 1H), 8.41-8.36 (m, 2H), 7.59 (dt, J=7.8, 2.0 Hz, 1H), 7.36-7.26 (m, 2H), 7.20 (ddd, J=10.6, 8.3, 1.2 Hz, 1H), 7.13 (td, J=7.5, 1.2 Hz, 1H), 6.97 (td, J=7.7, 1.7 Hz, 1H), 5.33 (s, 2H), 3.40 (d, J=12.7 Hz, 2H), 3.31 (s, 3H), 2.87-2.76 (m, 2H), 2.52 (d, J=7.3 Hz, 2H), 1.68 (ddd, J=11.2, 7.5, 3.8 Hz, 1H), 1.54 (d, J=12.8 Hz, 2H), 1.26-1.15 (m, 2H). HR-ESIMS: m/z 449.2096 (M+H)$^+$ calcd. for $C_{24}H_{26}FN_6O_2$, found 449.2094. HPLC Purity=98% (Retention Time=8.1 min).

f. Synthesis of 4-((8-(4-(4-(tert-butyl)benzyl)piperazin-1-yl)-3-methyl-2,6-dioxo-1,2,3,6-tetrahydro-7H-purin-7-yl)methyl)-3-fluorobenzoic Acid (19)

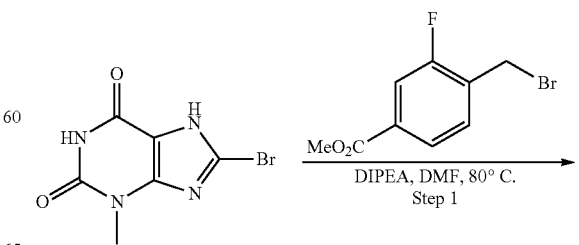

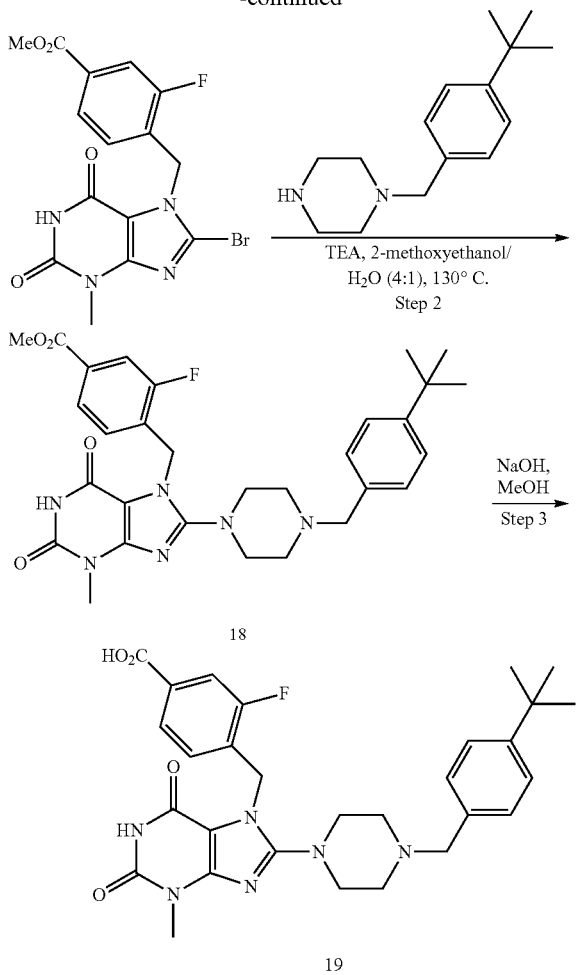

DCM (3×5 mL). The organic layers were washed with brine (10 mL), dried over $Na_2SO_4$, filtered, and concentrated in vacuo. The crude was purified via flash chromatography (0-5% MeOH/DCM) to give the desired compound 18 as a yellow-white solid. Yield: 260 mg (76%). $^1$H NMR (400 MHz, DMSO-$d_6$) δ 10.93 (s, 1H), 7.74-7.65 (m, 2H), 7.35-7.30 (m, 2H), 7.21-7.17 (m, 2H), 7.12 (t, J=7.7 Hz, 1H), 5.41 (s, 2H), 3.85 (s, 3H), 3.42 (s, 2H), 3.32 (s, 3H), 3.13 (t, J=4.9 Hz, 4H), 2.38 (d, J=5.3 Hz, 4H), 1.26 (s, 9H). HR-ESIMS: m/z 563.2777 (M+H)$^+$ calcd. for $C_3H_{36}FN_6O_4$, found 563.2790. HPLC Purity=100% (Retention Time=11.8 min).

iii. Step-3: Preparation of 4-((8-(4-(4-(tert-butyl)benzyl)piperazin-1-yl)-3-methyl-2,6-dioxo-1,2,3,6-tetrahydro-7H-purin-7-yl)methyl)-3-fluorobenzoic Acid (19)

To a solution of methyl 4-((8-(4-(4-(tert-Butyl)benzyl)piperazin-1-yl)-3-methyl-2,6-dioxo-1,2,3,6-tetrahydro-7H-purin-7-yl)methyl)-3-fluorobenzoate 18 (112 mg, 0.20 mmol) in methanol (2 mL) was added 1N sodium hydroxide (1 mL). The reaction was stirred at room temperature overnight. The reaction was then concentrated in vacuo, acidified to pH=3 with AcOH, and extracted with DCM (3×3 mL). The organic layers were washed with $H_2O$ twice and once with brine, then dried over $Na_2SO_4$, filtered, and concentrated in vacuo to give the desired product 19 as a white solid. Yield: 99 mg (90%). $^1$H NMR (400 MHz, DMSO-$d_6$) δ 10.93 (s, 1H), 7.72-7.61 (m, 2H), 7.36-7.29 (m, 2H), 7.22-7.16 (m, 2H), 7.08 (t, J=7.8 Hz, 1H), 5.40 (s, 2H), 3.43 (s, 2H), 3.32 (s, 3H), 3.14 (t, J=4.9 Hz, 4H), 2.38 (t, J=4.8 Hz, 4H), 1.25 (s, 9H) HR-ESIMS: m/z 549.2620 (M+H)$^+$ calcd. for $C_{29}H_{34}FN_6O_4$, found 549.2627. HPLC Purity=99% (Retention Time=10.5 min).

g. Synthesis of 8-(4-(3-(tert-butyl)phenyl)piperazin-1-yl)-7-(2-fluorobenzyl)-3-methyl-3,7-dihydro-1H-purine-2,6-dione (28)

i. Step-1: Preparation of methyl 4-((8-amino-3-methyl-2,6-dioxo-1,2,3,6-tetrahydro-7H-purin-7-yl)methyl)-3-fluorobenzoate A solution of 8-bromo-3-methyl-1H-purine-2,6(3H,7H)-dione (245 mg, 1.0 mmol), methyl 4-(bromomethyl)-3-fluorobenzoate (247 mg, 1.0 mmol), and DIPEA (0.19 mL, 1.1 mmol) in DMF (2 mL) was heated at 80° C. with stirring for 4 h. After cooling to ambient temperature, ice-cold water was added. The precipitate was collected by filtration, washed with cold water, and dried under high vacuum to give the desired compound (344 mg, 84%). $^1$H NMR (400 MHz, DMSO-$d_6$) δ 11.35 (s, 1H), 7.80-7.68 (m, 2H), 7.13 (t, J=7.8 Hz, 1H), 5.60 (s, 2H), 3.86 (s, 3H), 3.35 (s, 3H).

ii. Step-2: Preparation of methyl 4-((8-(4-(4-(tert-butyl)benzyl)piperazin-1-yl)-3-methyl-2,6-dioxo-1,2,3,6-tetrahydro-7H-purin-7-yl)methyl)-3-fluorobenzoate (18)

A solution of methyl 4-((8-bromo-3-methyl-2,6-dioxo-purin-7-yl)methyl)-3-fluoro-benzoate (250 mg, 0.61 mmol), 1-(4-(tert-butyl)benzyl)piperazine, TFA (155 mg, 0.67 mmol), and TEA (0.17 mL, 1.2 mmol) in 2-methoxyethanol:$H_2O$ (4:1, 3.75 mL) was heated at 130° C. for 18 h. The reaction was cooled to room temperature, diluted with saturated aqueous $NaHCO_3$ (5 mL), and extracted with

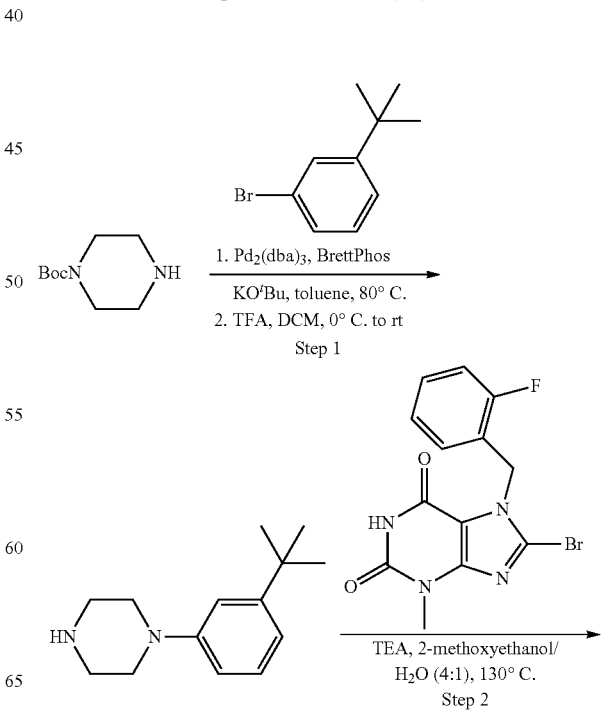

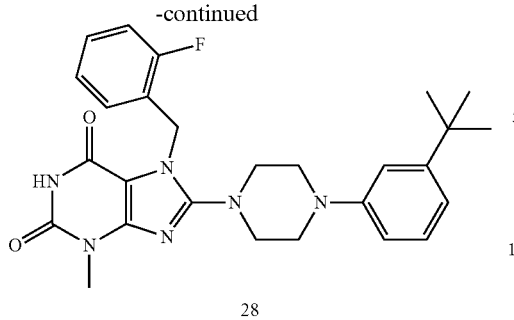

28 i. Step-1: Preparation of 1-(3-(tert-butyl)phenyl)piperazine

To a 25 mL Schlenk flask with a stir bar was added 1-Boc-piperazine (186 mg, 1.0 mmol), Tris(dibenzylideneacetone)dipalladium(0), (9.1 mg, 0.01 mmol), BrettPhos (16 mg, 0.03 mmol), and Potassium tert-butoxide (280 mg, 2.5 mmol). The flask was evacuated and filled with argon three times, followed by addition of 1-bromo-3-tert-butylbenzene (0.17 mL, 1.0 mmol) and toluene (4 mL). The flask was sealed, heated at 80° C., and stirred overnight. Upon completion, the reaction was cooled to room temperature, diluted with EtOAc, filtered through a short pad of silica gel, and concentrated under reduced pressure. The crude oil was purified via flash chromatography (0-10% EtOAc/hexanes) to afford the N-Boc intermediate as a yellow oil. $^1$H NMR (400 MHz, CDCl$_3$) δ 7.24-7.19 (m, 1H), 6.98 (t, J=2.1 Hz, 1H), 6.95 (ddd, J=7.7, 1.8, 0.9 Hz, 1H), 6.75 (ddd, J=8.1, 2.5, 0.9 Hz, 1H), 3.62-3.55 (m, 4H), 3.13 (t, J=5.2 Hz, 4H), 1.48 (s, 9H), 1.31 (s, 9H). To a solution of the N-Boc intermediate (80 mg, 0.25 mmol) in dry DCM (1.5 mL) at 0° C. was added TFA (0.58 mL, 7.5 mmol) dropwise under argon. The solution was warmed to room temperature and stirred overnight. The solution was concentrated in vacuo and purified via flash chromatography (0-10% MeOH/DCM) to give 1-(3-tert-butylphenyl)piperazine as a white TFA salt (65 mg, 21% over 2 steps). $^1$H NMR (400 MHz, CDCl$_3$) δ 7.25-7.22 (m, 1H), 7.06-7.02 (m, 1H), 6.97 (t, J=2.1 Hz, 1H), 6.76 (ddt, J=8.0, 2.4, 0.8 Hz, 1H), 3.44-3.39 (m, 4H), 3.36 (dd, J=6.6, 3.7 Hz, 4H), 1.31 (s, 9H).

ii. Step-2: Preparation of 8-(4-(3-(tert-butyl)phenyl)piperazin-1-yl)-7-(2-fluorobenzyl)-3-methyl-3,7-dihydro-1H-purine-2,6-dione (28)

A solution of 8-bromo-7-(2-fluorobenzyl)-3-methyl-1H-purine-2,6(3H,7H)-dione (71 mg, 0.20 mmol), 1-(3-tert-butylphenyl)piperazine, TFA (60 mg, 0.20 mmol), and TEA (98 µL, 0.7 mmol) in 2-methoxyethanol:H$_2$O (4:1, 1.25 mL) was heated at 130° C. for 18 h. The reaction was cooled to room temperature, diluted with saturated aqueous NaHCO$_3$ (5 mL), and extracted with DCM (3×5 mL). The organic layers were washed with brine (10 mL), dried over Na$_2$SO$_4$, filtered, and concentrated in vacuo. The crude was purified via flash chromatography (0-5% MeOH/DCM) to give the desired compound 28 as a white solid. Yield: 62 mg (63%). $^1$H NMR (400 MHz, DMSO-d$_6$) δ 10.95 (s, 1H), 7.38-7.30 (m, 1H), 7.22 (ddd, J=10.5, 8.3, 1.2 Hz, 1H), 7.14 (dt, J=8.8, 7.8 Hz, 2H), 7.03 (td, J=7.8, 1.7 Hz, 1H), 6.93 (t, J=2.1 Hz, 1H), 6.85 (ddd, J=7.8, 1.8, 0.8 Hz, 1H), 6.77-6.71 (m, 1H), 5.42 (s, 2H), 3.28 (dd, J=6.7, 3.4 Hz, 4H), 3.16 (dd, J=6.4, 3.6 Hz, 4H), 1.25 (s, 9H). HR-ESIMS: m/z 491.2565 (M+H)$^+$ calcd. for C$_{27}$H$_{32}$FN$_6$O$_2$, found 491.2557. HPLC Purity=95% (Retention Time=13.8 min).

h. Synthesis of 1-(4-(tert-butyl)benzyl)-4-(7-(2-fluorobenzyl)-3-methyl-2,6-dioxo-2,3,6,7-tetrahydro-1H-purin-8-yl)piperazine-2-carboxylic Acid (37)

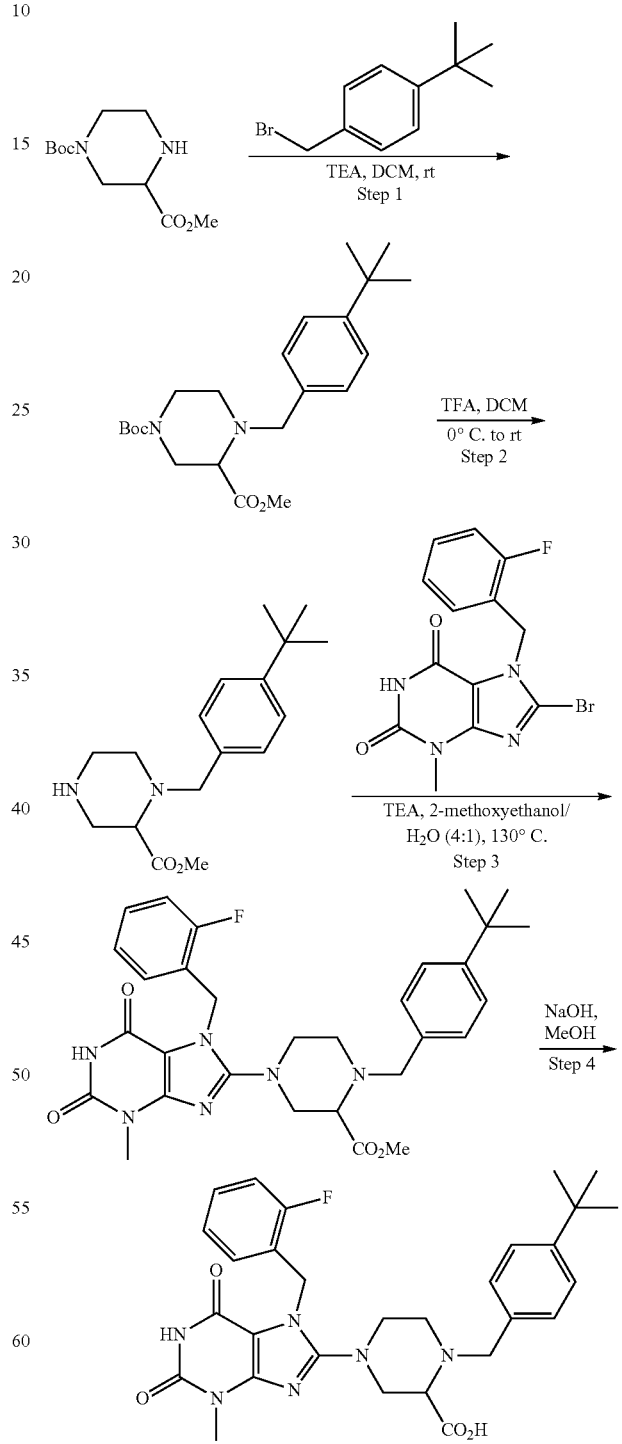

37 i. Step-1 and 2: Preparation of methyl 1-(4-(tert-butyl)benzyl)piperazine-2-carboxylate To a solution of 1-(bromomethyl)-4-tert-butyl-benzene (0.21 mL, 1.1 mmol) and TEA (0.16 mL, 1.1 mmol) in dry DCM (4 mL) was added 1-(tert-butyl) 3-methyl piperazine-1,3-dicarboxylate (250 mg, 1.0 mmol). After stirring at room temperature overnight, the reaction was diluted with H$_2$O (10 mL), extracted with DCM (2×20 mL). The organic layers were dried over Na$_2$SO$_4$, filtered, and concentrated in vacuo. The crude was purified via flash chromatography (0-10% EtOAc/hexanes) to give the dicarboxylate intermediate (150 mg, 37% yield) as a clear oil. To a cooled solution of 1-(tert-butyl) 3-methyl 4-(4-(tert-butyl)benzyl)piperazine-1,3-dicarboxylate (150 mg, 0.38 mmol) in DCM (2 mL) was added TFA (0.44 mL, 5.8 mmol) dropwise at 0° C. under argon. The solution was warmed to room temperature and stirred overnight. Upon completion, the solvent was removed and dried to give the desire product as a TFA salt (150 mg, 97%). $^1$H NMR (400 MHz, CDCl$_3$) δ 7.43-7.39 (m, 2H), 7.29-7.26 (m, 2H), 4.20 (d, J=13.3 Hz, 2H), 4.07 (dd, J=12.9, 6.7 Hz, 1H), 3.88 (s, 3H), 3.81 (dt, J=10.5, 5.2 Hz, 1H), 3.60 (s, 3H), 3.41 (t, J=10.2 Hz, 2H), 3.27 (s, 1H), 1.31 (s, 9H).

ii. Step-3: Preparation of methyl 1-(4-(tert-butyl)benzyl)-4-(7-(2-fluorobenzyl)-3-methyl-2,6-dioxo-2,3,6,7-tetrahydro-1H-purin-8-yl)piperazine-2-carboxylate A solution of 8-bromo-7-(2-fluorobenzyl)-3-methyl-1H-purine-2,6(3H,7H)-dione (88 mg, 0.25 mmol), methyl 1-(4-(tert-butyl)benzyl)piperazine-2-carboxylate (109 mg, 0.37 mmol), and TEA (0.12 mL, 0.87 mmol) in 2-methoxyethanol:H$_2$O (4:1, 1 mL) was heated at 130° C. for 18 h. The reaction was cooled to room temperature, diluted with saturated aqueous NaHCO$_3$ (5 mL), and extracted with DCM (3×5 mL). The organic layers were washed with brine (10 mL), dried over Na$_2$SO$_4$, filtered, and concentrated in vacuo. The crude was purified via flash chromatography (0-100% EtOAc/hexanes) to give the desired product (50 mg, 36%) which was carried forward in next step without characterization.

iii. Step-4: Preparation of 1-(4-(tert-butyl)benzyl)-4-(7-(2-fluorobenzyl)-3-methyl-2,6-dioxo-2,3,6,7-tetrahydro-1H-purin-8-yl)piperazine-2-carboxylic Acid (37)

To a solution of methyl 1-((4-tert-butylphenyl)methyl)-4-(7-((2-fluorophenyl)methyl)-3-methyl-2,6-dioxo-purin-8-yl)piperazine-2-carboxylate ester (50 mg, 0.09 mmol) in methanol (1 mL) was added 1N sodium hydroxide (1 mL) solution. The reaction was stirred at room temperature overnight. The reaction was then concentrated in vacuo, acidified to pH=3 with AcOH, and extracted with DCM (3×3 mL). The organic layers were washed twice with H$_2$O (3 mL) and once with brine (3 mL), then dried over Na$_2$SO$_4$, filtered, and concentrated in vacuo. The crude was purified via flash chromatography (0-9% MeOH/DCM) to give the desired compound 37 as a light tan solid. Yield: 29 mg (59%). $^1$H NMR (400 MHz, DMSO-d$_6$) δ 10.91 (s, 1H), 7.35-7.27 (m, 3H), 7.24-7.19 (m, 2H), 7.19-7.14 (m, 1H), 7.10 (td, J=7.5, 1.2 Hz, 1H), 6.94-6.88 (m, 1H), 5.35 (d, J=5.3 Hz, 2H), 3.87 (d, J=13.5 Hz, 1H), 3.64 (d, J=13.5 Hz, 1H), 3.48 (dd, J=11.9, 5.1 Hz, 1H), 3.32 (s, 3H), 3.25 (dd, J=11.9, 3.5 Hz, 2H), 3.10 (dd, J=19.9, 11.6 Hz, 3H), 2.97 (t, J=9.4 Hz, 1H), 2.38 (d, J=12.2 Hz, 1H), 1.26 (s, 9H). HR-ESIMS: m/z 549.2620 (M+H)$^+$ calcd. for C$_{29}$H$_{34}$FN$_6$O$_4$, found 549.2620. HPLC Purity=99% (Retention Time=10.9 min).

i. Synthesis of Compounds 38, 39, 41, 42, 45-48, 50

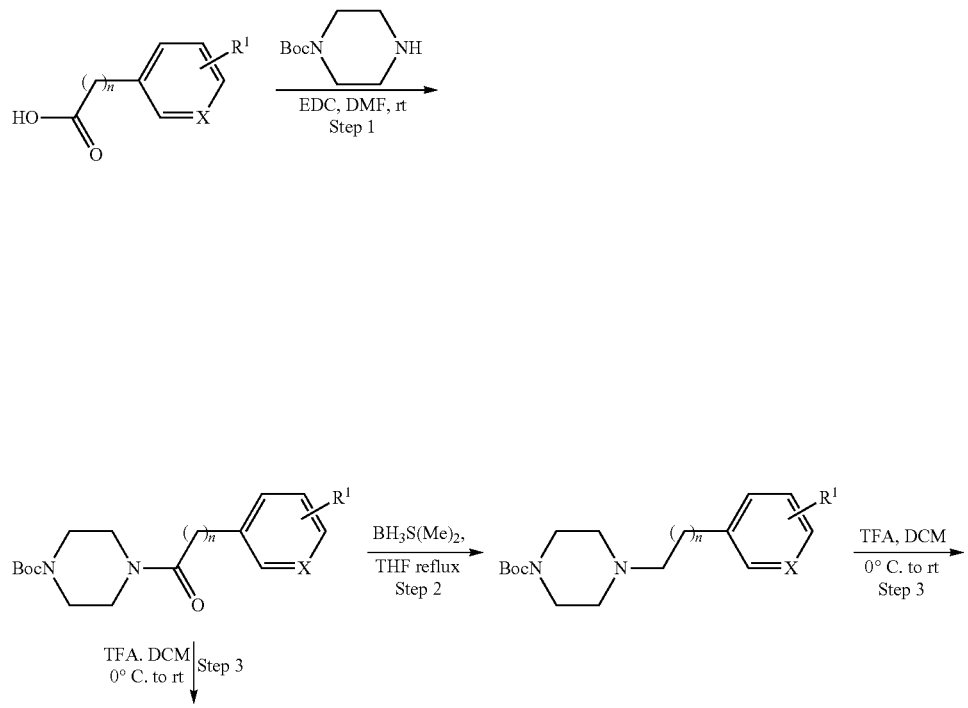

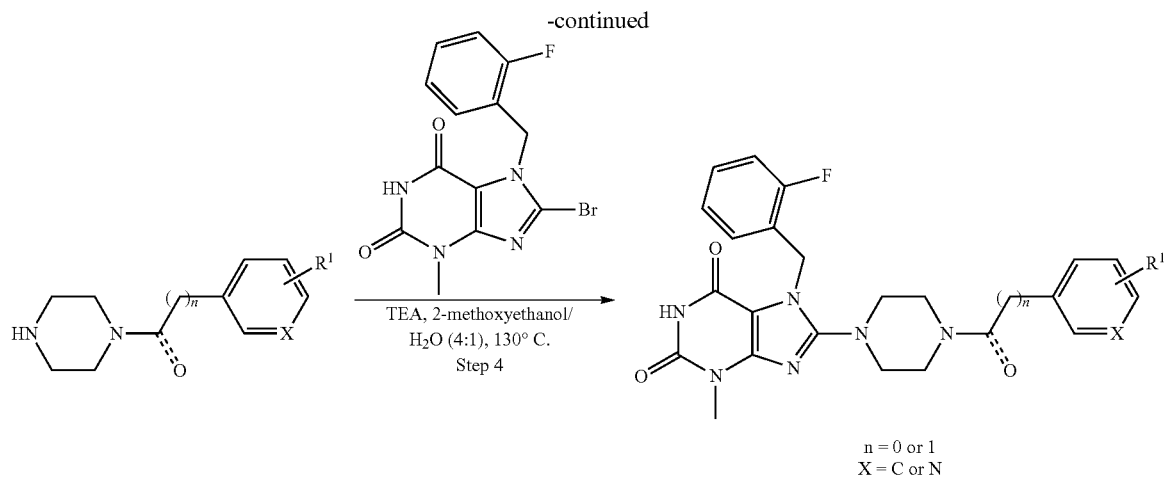

n = 0 or 1
X = C or N i. Step-1: General Procedure of Amide Coupling

To a stirred solution of tert-butyl piperazine-1-carboxylate (1 equiv.) and DMF (0.5 M), was added carboxylic acid (1.1 equiv.) followed by EDC (2.2 equiv.). The reaction mass was stirred at room temperature overnight. After completion, the reaction was diluted with $H_2O$ (5 mL) and extracted with DCM (3×5 mL). The organic layers were washed with brine, dried over $Na_2SO_4$, filtered, and concentrated in vacuo.

ii. Step-2: General Procedure of Amide Reduction

To a cooled solution of amide (1 equiv.) in THF (0.4 M) was added borane dimethyl sulfide complex solution in 2.0 M THF (1-3 equiv.) dropwise. The reaction was warmed to room temperature and refluxed for 2 h. The reaction was then quenched at 0° C. with MeOH. The solvent was evaporated and the white solids were washed with $Et_2O$, dried under vacuum, and carried forward without purification.

iii. Step-3: General Procedure of Boc Deprotection

To a cooled solution of piperazine carboxylate (1 equiv.) in dry DCM (0.3 M) at 0° C. was added TFA (30 equiv.) dropwise under argon. The solution was stirred at room temperature overnight. Evolution of gas was observed. The solution was concentrated in vacuo, $Et_2O$ was added and the white precipitates were collected by filtration and dried under vacuum.

iv. Step-4: General Procedure to Synthesize Compounds 38, 39, 41, 42, 45-48, 50

A mixture of 8-bromo-7-(2-fluorobenzyl)-3-methyl-1H-purine-2,6(3H,7H)-dione (1 equiv.), appropriate piperazine (1.1 equiv.), and TEA (1.5-3 equiv.) in 2-methoxyethanol/$H_2O$ (4:1, 0.25 M) was heated at 130° C. for 16 h. The reaction was cooled to room temperature, diluted with saturated aqueous $NaHCO_3$ (5 mL), and extracted with DCM (3×5 mL). Combined organic layers were washed with brine (5 mL), dried over anhydrous $Na_2SO_4$, filtered, and concentrated in vacuo. The crude product was purified on a pre-packed Silica gel column using Teledyne ISCO flash chromatographic system.

(6-(tert-Butyl)pyridin-3-yl)(piperazin-1-yl)methanone. Following Step-1, with tert-butyl piperazine-1-carboxylate (279 mg, 1.5 mmol), 6-(tert-butyl)nicotinic acid (296 mg, 1.6 mmol), and EDC (633 mg, 3.3 mmol) in DMF (3 mL), the crude was purified via flash chromatography (0-30% EtOAc/hexanes) to give the desired amide intermediate (431 mg, 81%). The amide intermediate (431 mg, 1.2 mmol) was subjected to Boc deprotection, following step 3, with TFA (2.9 mL, 37 mmol) in dry DCM (4 mL) to give the desire product as a white TFA salt (425 mg, 95%). $^1$H NMR (400 MHz, DMSO-$d_6$) δ 8.98 (s, 2H), 8.62 (ddd, J=2.4, 1.5, 0.9 Hz, 1H), 7.89-7.81 (m, 1H), 7.57-7.49 (m, 1H), 3.70 (s, 4H), 3.18 (s, 4H), 1.33 (d, J=0.6 Hz, 9H).

8-(4-(6-(tert-Butyl)nicotinoyl)piperazin-1-yl)-7-(2-fluorobenzyl)-3-methyl-3,7-dihydro-1H-purine-2,6-dione (45). Following Step-4, with 8-bromo-7-(2-fluorobenzyl)-3-methyl-1H-purine-2,6(3H,7H)-dione (88 mg, 0.25 mmol), (6-(tert-butyl)pyridin-3-yl)(piperazin-1-yl)methanone, TFA (143 mg, 0.30 mmol), and TEA (0.14 mL, 1.0 mmol) in 2-methoxyethanol:$H_2O$ (4:1, 1.25 mL), the resulting product was purified via flash chromatography (0-5% MeOH/DCM) to give the desired compound 45 as an ivory solid. Yield: 56 mg (43%). $^1$H NMR (400 MHz, DMSO-$d_6$) δ 10.96 (s, 1H), 8.54 (dd, J=2.3, 0.8 Hz, 1H), 7.77 (dd, J=8.2, 2.3 Hz, 1H), 7.48 (dd, J=8.2, 0.9 Hz, 1H), 7.36-7.28 (m, 1H), 7.20 (ddd, J=10.5, 8.3, 1.2 Hz, 1H), 7.13 (td, J=7.5, 1.2 Hz, 1H), 6.99 (td, J=7.7, 1.7 Hz, 1H), 5.39 (s, 2H), 3.67 (d, J=15.0 Hz, 2H), 3.40 (s, 2H), 3.31 (s, 3H), 3.19 (s, 4H), 1.30 (s, 9H). HR-ESIMS: m/z 520.2467 (M+H)$^+$ calcd. for $C_{27}H_{31}FN_7O_3$, found 520.2457. HPLC Purity=100% (Retention Time=12.0 min).

1-((6-(tert-butyl)pyridin-3-yl)methyl)piperazine. Following Step-2, with (6-(tert-butyl)pyridin-3-yl)(piperazin-1-yl) methanone, TFA (200 mg, 0.55 mmol) and borane dimethyl sulfide complex solution in 2.0 M THF (0.63 mL, 1.3 mmol) in THF (1.5 mL), the desired product was afforded as a white solid (130 mg, 89%) and carried out without purification. $^1$H NMR (400 MHz, DMSO-$d_6$) δ 8.41 (dd, J=2.3, 0.9 Hz, 1H), 7.62 (dd, J=8.1, 2.4 Hz, 1H), 7.39 (dd, J=8.1, 0.9 Hz, 1H), 3.52 (s, 2H), 3.03 (d, J=5.1 Hz, 4H), 2.51 (s, 4H), 1.28 (s, 9H).

8-(4-((6-(tert-Butyl)pyridin-3-yl)methyl)piperazin-1-yl)-7-(2-fluorobenzyl)-3-methyl-3,7-dihydro-1H-purine-2,6-dione (38). Following Step-4, with 8-bromo-7-(2-fluorobenzyl)-3-methyl-1H-purine-2,6(3H,7H)-dione (88 mg, 0.25 mmol), 1-((6-tert-butyl)pyridin-3-yl)methyl)piperazine (104 mg, 0.30 mmol), and TEA (35 µL, 0.25 mmol) in 2-methoxyethanol:H$_2$O (4:1, 1.25 mL), the resulting product was purified via flash chromatography (0-5% MeOH/DCM) to give the desired compound 38 as a white solid. Yield: 35 mg (28%). $^1$H NMR (400 MHz, DMSO-d$_6$) δ 10.92 (s, 1H), 8.39 (dd, J=2.4, 0.8 Hz, 1H), 7.61 (dd, J=8.2, 2.3 Hz, 1H), 7.38 (dd, J=8.1, 0.9 Hz, 1H), 7.32 (dddd, J=8.3, 7.3, 5.4, 1.7 Hz, 1H), 7.19 (ddd, J=10.6, 8.3, 1.2 Hz, 1H), 7.12 (td, J=7.5, 1.2 Hz, 1H), 6.98 (td, J=7.7, 1.7 Hz, 1H), 5.37 (s, 2H), 3.47 (s, 2H), 3.32 (s, 3H), 3.14 (t, J=4.9 Hz, 4H), 2.39 (t, J=4.9 Hz, 4H), 1.29 (s, 9H). HR-ESIMS: m/z 506.2674 (M+H)$^+$ calcd. for C$_{27}$H$_{33}$FN$_7$O$_2$, found 506.2682. HPLC Purity=98% (Retention Time=10.7 min).

tert-Butyl 4-(4-(2-cyanopropan-2-yl)benzoyl)piperazine-1-carboxylate. Following Step-1, with tert-butyl piperazine-1-carboxylate (270 mg, 1.4 mmol), 4-(2-cyanopropan-2-yl) benzoic acid (302 mg, 1.6 mmol), and EDC (611 mg, 3.2 mmol) in DMF (3 mL), the crude was purified via flash chromatography (0-30% EtOAc/hexanes) to give the desired product (443 mg, 85%). $^1$H NMR (400 MHz, DMSO-d$_6$) δ 7.60-7.55 (m, 2H), 7.48-7.43 (m, 2H), 3.56 (s, 2H), 3.33 (s, 6H), 1.69 (s, 6H), 1.39 (s, 9H).

2-Methyl-2-(4-(piperazin-1-ylmethyl)phenyl)propanenitrile. Following Step-2, with tert-butyl 4-(4-(2-cyanopropan-2-yl)benzoyl)piperazine-1-carboxylate (332 mg, 0.93 mmol) and borane dimethyl sulfide complex solution in 2.0 M THF (0.51 mL, 1.0 mmol) in THF (3.3 mL), the desired tert-butyl 4-(4-(2-cyanopropan-2-yl)benzyl)piperazine-1-carboxylate was afforded as a white solid. The amide intermediate (431 mg, 1.2 mmol) was subjected to Boc deprotection, following Step-3, with TFA (1.0 mL, 13 mmol) in dry DCM (2 mL) to give the desired product as a white solid (148 mg, 45% over 2 steps). $^1$H NMR (400 MHz, DMSO-d$_6$) δ 8.78 (s, 2H), 7.55 (d, J=8.1 Hz, 2H), 7.45 (d, J=7.9 Hz, 2H), 3.87 (s, 2H), 3.19 (s, 4H), 2.84 (s, 4H), 1.69 (s, 6H).

2-(4-((4-(7-(2-Fluorobenzyl)-3-methyl-2,6-dioxo-2,3,6,7-tetrahydro-1H-purin-8-yl)piperazin-1-yl)methyl)phenyl)-2-methylpropanenitrile (39). Following Step-4, with 8-bromo-7-(2-fluorobenzyl)-3-methyl-1H-purine-2,6(3H,7H)-dione (88 mg, 0.25 mmol), 2-methyl-2-(4-(piperazin-1-ylmethyl)phenyl)propanenitrile (89 mg, 0.25 mmol), and TEA (0.12 mL, 0.87 mmol) in 2-methoxyethanol:H$_2$O (4:1, 1.25 mL), the resulting product was purified via flash chromatography (0-100% EtOAc/hexanes) to give the desired compound 39 as a white solid. Yield: 37 mg (29%). $^1$H NMR (400 MHz, DMSO-d$_6$) δ 10.91 (s, 1H), 7.49-7.43 (m, 2H), 7.36-7.29 (m, 3H), 7.20 (ddd, J=10.6, 8.2, 1.2 Hz, 1H), 7.13 (td, J=7.5, 1.2 Hz, 1H), 6.98 (td, J=7.7, 1.7 Hz, 1H), 5.37 (s, 2H), 3.48 (s, 2H), 3.32 (s, 3H), 3.15 (dd, J=5.9, 3.6 Hz, 4H), 2.39 (t, J=5.0 Hz, 4H), 1.67 (s, 6H). HR-ESIMS: m/z 516.2518 (M+H)$^+$ calcd. for C$_{28}$H$_{31}$FN$_7$O$_2$, found 516.2517. HPLC Purity=100% (Retention Time=9.8 min).

tert-Butyl 4-(2-(2,5-dimethylphenyl)acetyl)piperazine-1-carboxylate. Following Step-1, with tert-butyl piperazine-1-carboxylate (186 mg, 1.0 mmol), 2-(2,5-dimethylphenyl) acetic acid (181 mg, 1.1 mmol), and EDC (422 mg, 2.2 mmol) in DMF (2 mL), the crude was purified via flash chromatography (0-50% EtOAc/hexanes) to give the desired product (254 mg, 76%). $^1$H NMR (400 MHz, CDCl$_3$) δ 7.06 (d, J=7.6 Hz, 1H), 6.99-6.95 (m, 1H), 6.93 (s, 1H), 3.65 (s, 4H), 3.42 (t, J=5.3 Hz, 2H), 3.37 (s, 2H), 3.30 (s, 2H), 2.28 (d, J=0.8 Hz, 3H), 2.23 (s, 3H), 1.61-1.57 (m, 2H), 1.46 (s, 9H).

1-(2,5-Dimethylphenethyl)piperazine. Following Step-2, with tert-butyl 4-(2-(2,5-dimethylphenyl)acetyl)piperazine-1-carboxylate (332 mg, 1.0 mmol) and borane dimethyl sulfide complex solution in 2.0 M THF (1.5 mL, 3.0 mmol) in THF (2.5 mL), the desired tert-butyl 4-(2,5-dimethylphenethyl)piperazine-1-carboxylate was afforded as a white solid and subjected to Boc-deprotection, following Step-3, with TFA (2.3 mL, 30 mmol) in DCM (3 mL) to give the desired product as a white TFA salt (210 mg, 96% over 2 steps). $^1$H NMR (400 MHz, DMSO-d$_6$) δ 9.10 (s, 1H), 7.07-6.98 (m, 2H), 6.98-6.93 (m, 1H), 3.57-3.47 (m, 1H), 3.41-3.30 (m, 3H), 3.28 (d, J=4.9 Hz, 2H), 3.14-2.96 (m, 3H), 2.93-2.79 (m, 2H), 2.23 (d, J=4.8 Hz, 6H).

8-(4-(2,5-Dimethylphenethyl)piperazin-1-yl)-7-(2-fluorobenzyl)-3-methyl-3,7-dihydro-1H-purine-2,6-dione (46). Following Step-4, with 8-bromo-7-(2-fluorobenzyl)-3-methyl-1H-purine-2,6(3H,7H)-dione (88 mg, 0.25 mmol), 1-(2,5-dimethylphenethyl)piperazine, TFA (125 mg, 0.38 mmol), and TEA (0.12 mL, 0.88 mmol) in 2-methoxyethanol:H$_2$O (4:1, 1.25 mL), the resulting product was purified via flash chromatography (0-5% MeOH/DCM) to give the desired compound 46 as a white solid. Yield: 82 mg (67%). $^1$H NMR (400 MHz, CDCl$_3$) δ 8.06 (s, 1H), 7.31-7.27 (m, 1H), 7.09 (ddd, J=5.9, 2.2, 0.7 Hz, 2H), 7.07-7.01 (m, 2H), 6.93 (d, J=7.9 Hz, 2H), 5.40 (s, 2H), 3.52 (s, 3H), 3.29-3.24 (m, 4H), 2.78-2.72 (m, 2H), 2.61-2.52 (m, 6H), 2.30-2.28 (m, 3H), 2.27 (s, 3H). HR-ESIMS: m/z 491.2565 (M+H)$^+$ calcd. for C$_{27}$H$_{32}$FN$_6$O$_2$, found 491.2558. HPLC Purity=98% (Retention Time=12.9 min).

1-(4-(tert-butyl)phenethyl)piperazine. Following Step-1, with tert-butyl piperazine-1-carboxylate (373 mg, 2.0 mmol), 2-(4-(tert-butyl)phenyl)acetic acid (423 mg, 2.2 mmol), and EDC (843 mg, 4.4 mmol) in DMF (5 mL), the crude was purified via flash chromatography (0-35% EtOAc/ hexanes) to give the desired carboxylate. Following Step-2, with tert-butyl 4-(2-(4-(tert-butyl)phenyl)acetyl)piperazine-1-carboxylate (303 mg, 0.84 mmol) and borane dimethyl sulfide complex solution in 2.0 M THF (1.2 mL, 2.5 mmol) in THF (2 mL), the desired tert-butyl 4-(4-(tert-butyl)phenethyl)piperazine-1-carboxylate was afforded as a white solid and subjected to Boc-deprotection as described in Step-3, with TFA (1.9 mL, 25 mmol) in DCM (2.5 mL) to give the desired product as a white TFA salt (300 mg, 79% over 3 steps). $^1$H NMR (400 MHz, DMSO-d$_6$) δ 9.07 (s, 1H), 7.37-7.30 (m, 2H), 7.23-7.14 (m, 2H), 3.43-3.01 (m, 10H), 2.86 (t, J=8.3 Hz, 2H), 1.26 (s, 9H).

8-(4-(4-(tert-Butyl)phenethyl)piperazin-1-yl)-7-(2-fluorobenzyl)-3-methyl-3,7-dihydro-1H-purine-2,6-dione (47). Following Step-4, with 8-bromo-7-(2-fluorobenzyl)-3-methyl-1H-purine-2,6(3H,7H)-dione (88 mg, 0.25 mmol), 1-(4-(tert-butyl)phenethyl)piperazine, TFA (135 mg, 0.38 mmol), and TEA (0.1 mL, 0.75 mmol) in 2-methoxyethanol: H$_2$O (4:1, 1.25 mL), the resulting product was purified via flash chromatography (0-75% EtOAc/hexanes) to give the desired compound 47 as a white solid. Yield: 80 mg (62%). $^1$H NMR (400 MHz, DMSO-d$_6$) δ 10.92 (s, 1H), 7.37-7.30 (m, 1H), 7.29-7.25 (m, 2H), 7.22 (ddd, J=10.6, 8.3, 1.2 Hz, 1H), 7.17-7.10 (m, 3H), 6.99 (td, J=7.7, 1.7 Hz, 1H), 5.38 (s, 2H), 3.33 (s, 3H), 3.15 (t, J=4.9 Hz, 4H), 2.66 (dd, J=9.6, 6.2 Hz, 2H), 2.47 (t, J=5.2 Hz, 4H), 1.25 (s, 9H). HR-ESIMS: m/z 519.2878 (M+H)$^+$ calcd. for C$_{29}$H$_{36}$FN$_6$O$_2$, found 519.2875. HPLC Purity=99% (Retention Time=14.5 min).

2-(2,5-Dimethylphenyl)-1-(piperazin-1-yl)ethan-1-one. Following the Boc-deprotection procedure described in Step-3, with tert-butyl 4-(2-(2,5-dimethylphenyl)acetyl)piperazine-1-carboxylate (250 mg, 0.75 mmol) and TFA (1.7 mL, 23 mmol) in DCM (3 mL), the desired product was afforded as a white TFA salt (240 mg, 92%). $^1$H NMR (400 MHz, DMSO-d$_6$) δ 8.93 (s, 1H), 7.03 (d, J=7.6 Hz, 1H), 6.94

(dd, J=7.7, 1.8 Hz, 1H), 6.86 (d, J=1.8 Hz, 1H), 3.67 (d, J=8.6 Hz, 6H), 3.10 (d, J=6.5 Hz, 4H), 2.23 (s, 3H), 2.13 (s, 3H).

8-(4-(2-(2,5-Dimethylphenyl)acetyl)piperazin-1-yl)-7-(2-fluorobenzyl)-3-methyl-3,7-dihydro-1H-purine-2,6-dione (48). Following Step-4, with 8-bromo-7-(2-fluorobenzyl)-3-methyl-1H-purine-2,6(3H,7H)-dione (88 mg, 0.25 mmol), 2-(2,5-dimethylphenyl)-1-(piperazin-1-yl)ethanone, TFA (95 mg, 0.28 mmol), and TEA (0.12 mL, 0.88 mmol) in 2-methoxyethanol:$H_2O$ (4:1, 1.25 mL), the resulting product was purified via flash chromatography (0-5% MeOH/DCM) to give the desired compound 48 as a light-tan solid. Yield: 70 mg (55%). $^1$H NMR (400 MHz, DMSO-$d_6$) δ 10.96 (s, 1H), 7.34 (tdd, J=7.5, 5.4, 1.8 Hz, 1H), 7.22 (ddd, J=10.7, 8.3, 1.2 Hz, 1H), 7.15 (td, J=7.5, 1.2 Hz, 1H), 7.04-6.99 (m, 2H), 6.92 (dd, J=8.0, 1.8 Hz, 1H), 6.85 (t, J=1.2 Hz, 1H), 5.41 (s, 2H), 3.65 (s, 2H), 3.54 (t, J=5.1 Hz, 4H), 3.33 (s, 3H), 3.12 (s, 4H), 2.22 (s, 3H), 2.12 (s, 3H). HR-ESIMS: m/z 505.2358 (M+H)$^+$ calcd. for $C_{27}H_{30}FN_6O_3$, found 505.2352. HPLC Purity=97% (Retention Time=13.5 min).

2-(4-(tert-butyl)phenyl)-1-(piperazin-1-yl)ethanone. Following the Boc-deprotection procedure described in Step-3, with tert-butyl 4-(2-(4-(tert-butyl)phenyl)acetyl)piperazine-1-carboxylate (300 mg, 0.83 mmol) and TFA (1.9 mL, 25 mmol) in DCM (2.5 mL), the desired product was afforded as a white TFA salt (173 mg, 55%). $^1$H NMR (400 MHz, CDCl$_3$) δ 7.37-7.32 (m, 2H), 7.15-7.09 (m, 2H), 3.87 (d, J=9.0 Hz, 2H), 3.70 (d, J=7.2 Hz, 4H), 3.07 (d, J=6.3 Hz, 2H), 2.81 (s, 2H), 1.30 (s, 9H).

8-(4-(2-(4-(tert-Butyl)phenyl)acetyl)piperazin-1-yl)-7-(2-fluorobenzyl)-3-methyl-3,7-dihydro-1H-purine-2,6-dione (50). Following Step-4, with 8-bromo-7-(2-fluorobenzyl)-3-methyl-1H-purine-2,6(3H,7H)-dione (88 mg, 0.25 mmol), 2-(4-(tert-butyl)phenyl)-1-(piperazin-1-yl)ethanone, TFA (140 mg, 0.38 mmol), and TEA (0.14 mL, 1.0 mmol) in 2-methoxyethanol:$H_2O$ (4:1, 1.25 mL), the resulting product was purified via flash chromatography (0-75% EtOAc/hexanes) to give the desired compound 50 as a white solid. Yield: 76 mg (57%). $^1$H NMR (400 MHz, DMSO-$d_6$) δ 10.95 (s, 1H), 7.38-7.27 (m, 3H), 7.20 (ddd, J=10.6, 8.3, 1.2 Hz, 1H), 7.16-7.09 (m, 3H), 7.00 (td, J=7.8, 1.7 Hz, 1H), 5.39 (s, 2H), 3.68 (s, 2H), 3.56-3.47 (m, 4H), 3.32 (s, 3H), 3.08 (dd, J=16.1, 5.3 Hz, 4H), 1.26 (s, 9H). HR-ESIMS: m/z 533.2671 (M+H)$^+$ calcd. for $C_{29}H_{34}FN_6O_3$, found 533.2670. HPLC Purity=100% (Retention Time=16.4 min).

tert-Butyl 4-(4-(2-hydroxypropan-2-yl)benzoyl)piperazine-1-carboxylate. Following Step-1, with tert-butyl piperazine-1-carboxylate (240 mg, 1.3 mmol), 4-(2-hydroxypropan-2-yl)benzoic acid (255 mg, 1.4 mmol), and EDC (543 mg, 2.8 mmol) in DMF (4 mL), the crude was purified via flash chromatography (0-80% EtOAc/hexanes) to give the desired product (412 mg, 91%). $^1$H NMR (400 MHz, DMSO-$d_6$) δ 7.54-7.50 (m, 2H), 7.36-7.32 (m, 2H), 5.08 (s, 1H), 3.36 (s, 8H), 1.43 (s, 6H), 1.41 (s, 9H).

1-(4-i-propylbenzyl)piperazine. Following Step-2, with tert-butyl 4-(4-(2-hydroxypropan-2-yl)benzoyl)piperazine-1-carboxylate (334 mg, 0.96 mmol) and borane dimethyl sulfide complex solution in 2.0 M THF (1.0 mL, 2.1 mmol) in THF (4 mL), the desired tert-butyl 4-(4-(2-hydroxypropan-2-yl)benzyl)piperazine-1-carboxylate was afforded as a white solid (118 mg, 37%). $^1$H NMR (400 MHz, CDCl$_3$) δ 7.53-7.49 (m, 2H), 7.34-7.31 (m, 2H), 4.06 (s, 2H), 3.74 (d, J=13.0 Hz, 4H), 2.85 (d, J=11.8 Hz, 2H), 2.69 (d, J=12.3 Hz, 2H), 1.60 (s, 6H), 1.42 (s, 9H). N-Boc piperazine intermediate (118 mg, 0.35 mmol) was then subjected to boc-deprotection, following Step-3, with TFA (0.8 mL, 10.6 mmol) in dry DCM (2 mL) to give the desired product as a white TFA salt (115 mg, 98%). $^1$H NMR (400 MHz, DMSO-$d_6$) δ 8.84 (s, 2H), 7.33 (d, J=7.9 Hz, 2H), 7.28 (d, J=7.9 Hz, 2H), 3.93 (s, 2H), 3.22 (s, 4H), 2.90 (dt, J=13.8, 6.9 Hz, 4H), 1.21 (s, 3H), 1.19 (s, 3H).

7-(2-Fluorobenzyl)-8-(4-(4-isopropylbenzyl)piperazin-1-yl)-3-methyl-3,7-dihydro-1H-purine-2,6-dione (41). A solution of 8-bromo-7-(2-fluorobenzyl)-1,3-dimethyl-1H-purine-2,6(3H,7H)-dione (74 mg, 0.21 mmol), 1-(4-i-propylbenzyl)piperazine, TFA (50 mg, 0.23 mmol), and $K_2CO_3$ (87 mg, 0.63 mmol) in NMP (2 mL) was irradiated at 110° C. under microwave conditions for 2 h. To the reaction mixture was added water (2 mL) and EtOAc (5 mL). The organic phase was separated and washed with water (3×3 mL). The organic layer was dried over $Na_2SO_4$, filtered, and concentrated in vacuo. The crude was purified via flash chromatography (0-100% EtOAc/hexanes) to give the desired compound 41 as a yellow solid. Yield: 34 mg (33%). $^1$H NMR (400 MHz, DMSO-$d_6$) δ 10.91 (s, 1H), 7.32 (tdd, J=7.3, 5.4, 1.7 Hz, 1H), 7.23-7.15 (m, 5H), 7.13 (td, J=7.5, 1.2 Hz, 1H), 6.98 (td, J=7.8, 1.7 Hz, 1H), 5.36 (s, 2H), 3.42 (s, 2H), 3.31 (s, 3H), 3.14 (t, J=4.8 Hz, 4H), 2.85 (hept, J=6.9 Hz, 1H), 2.37 (t, J=4.9 Hz, 4H), 1.18 (d, J=6.9 Hz, 6H). HR-ESIMS: m/z 491.2526 (M+H)$^+$ calcd. for $C_{27}H_{32}FN_6O_2$, found 491.2654. HPLC Purity=99% (Retention Time=10.1 min).

1-(4-(prop-1-en-2-yl)benzyl)piperazine. A mixture of tert-butyl 4-(4-(2-hydroxypropan-2-yl)benzyl)piperazine-1-carboxylate (50 mg, 0.15 mmol) and 4M HCl in dioxane (1 mL) was stirred at room temperature overnight. The white solids were collected, washed with Et$_2$O, and dried under vacuum to give the desired product (30 mg, 86%). $^1$H NMR (400 MHz, DMSO-$d_6$) δ 9.68 (s, 2H), 7.73-7.46 (m, 4H), 4.34 (s, 2H), 3.76 (s, 1H), 3.44 (s, 5H), 3.22 (s, 2H), 1.98 (s, 3H), 1.43 (s, 2H).

7-(2-Fluorobenzyl)-3-methyl-8-(4-(4-(prop-1-en-2-yl)benzyl)piperazin-1-yl)-3,7-dihydro-1H-purine-2,6-dione (42). A solution of 8-bromo-7-(2-fluorobenzyl)-1,3-dimethyl-1H-purine-2,6(3H,7H)-dione (53 mg, 0.15 mmol), 1-(4-(prop-1-en-2-yl)benzyl)piperazine (39 mg, 0.16 mmol), and $K_2CO_3$ (52 mg, 0.37 mmol) in NMP (1.5 mL) was irradiated at 140° C. under microwave conditions for 3 h. To the reaction mixture was added water (2 mL) and EtOAc (5 mL). The organic phase was separated and washed with water (3×3 mL). The organic layer was dried over $Na_2SO_4$, filtered, and concentrated in vacuo. The crude was purified via flash chromatography (0-100% EtOAc/hexanes) to give the desired compound 42 as an ivory solid. Yield: 15 mg (20%). $^1$H NMR (400 MHz, CDCl$_3$) δ 7.79 (s, 1H), 7.45-7.38 (m, 2H), 7.28-7.27 (m, 1H), 7.26-7.22 (m, 2H), 7.09-7.00 (m, 3H), 5.38 (s, 2H), 5.36 (dd, J=1.6, 0.8 Hz, 1H), 5.07 (p, J=1.5 Hz, 1H), 3.51 (d, J=3.8 Hz, 5H), 3.25-3.17 (m, 4H), 2.52-2.45 (m, 4H), 2.14 (dd, J=1.5, 0.8 Hz, 3H). HR-ESIMS: m/z 489.2408 (M+H)$^+$ calcd. for $C_{27}H_{30}FN_6O_2$, found 489.2407. HPLC Purity=99% (Retention Time=10.8 min).

j. Synthesis of 8-(4-(2-(4-(tert-butyl)phenyl)-2-oxoethyl)piperazin-1-yl)-7-(2-fluorobenzyl)-3-methyl-3,7-dihydro-1H-purine-2,6-dione (49)

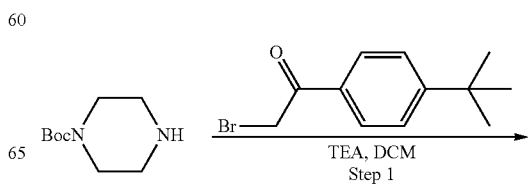

J=4.8 Hz, 4H), 1.29 (s, 9H). HR-ESIMS: m/z 533.2671 (M+H)+ calcd. for $C_{29}H_{34}FN_6O_3$, found 533.2658. HPLC Purity=98% (Retention Time=14.1 min).

k. Synthesis of 7-(2-fluorobenzyl)-8-(4-(4-(2-hydroxypropan-2-yl)benzyl)piperazin-1-yl)-3-methyl-3,7-dihydro-1H-purine-2,6-dione (40)

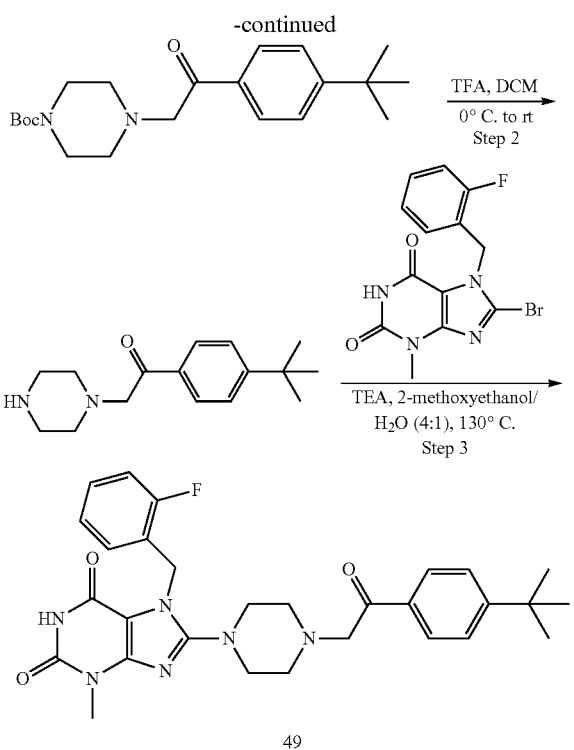

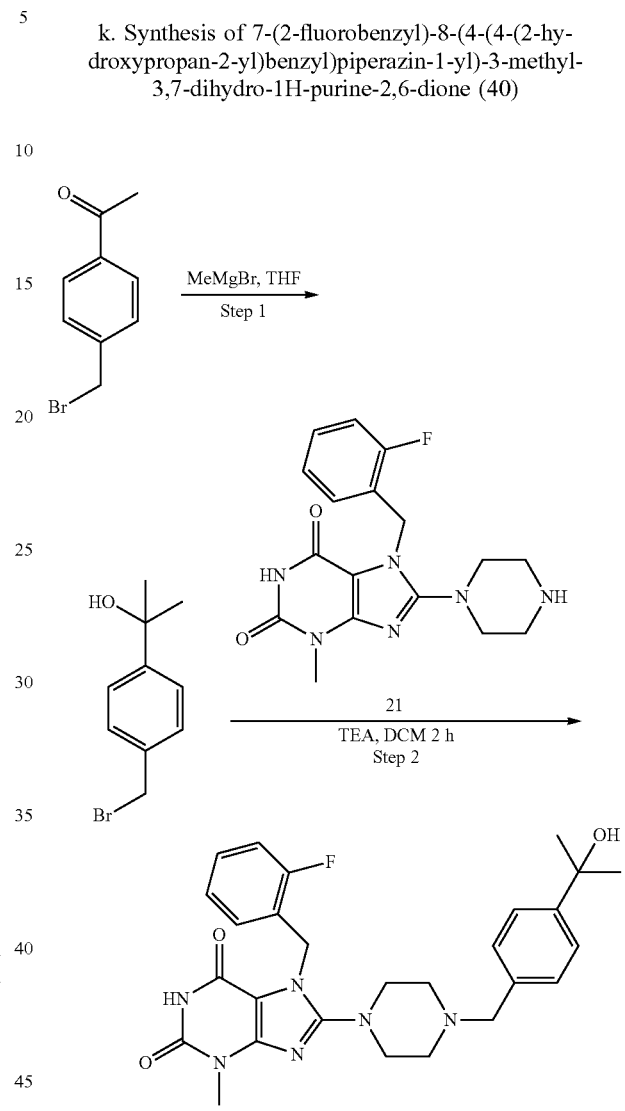

i. Step-1 and 2: Preparation of 1-(4-(tert-butyl)phenyl)-2-(piperazin-1-yl)ethan-1-one To a solution of 2-bromo-1-(4-(tert-butyl)phenyl)ethanone (281 mg, 1.1 mmol) and tert-butyl piperazine-1-carboxylate (186 mg, 1.0 mmol) in DCM (4 ml) was added TEA (0.15 mL, 1.1 mmol). The reaction was stirred at room temperature overnight. Upon completion, the solvent was evaporated and the crude was subjected to Boc-deprotection with TFA (1.8 mL, 23 mmol) and DCM to give the desired product as a white TFA salt (245 mg, 65% over 2 steps). ¹H NMR (400 MHz, DMSO-$d_6$) δ 8.84 (s, 1H), 7.93-7.89 (m, 2H), 7.58 (dd, J=8.6, 2.3 Hz, 2H), 4.46 (s, 1H), 3.26 (s, 4H), 3.07 (s, 3H), 1.31 (s, 9H).

ii. Step-3: Preparation of 8-(4-(2-(4-(tert-butyl)phenyl)-2-oxoethyl)piperazin-1-yl)-7-(2-fluorobenzyl)-3-methyl-3,7-dihydro-1H-purine-2,6-dione (49)

A solution of 8-bromo-7-(2-fluorobenzyl)-3-methyl-1H-purine-2,6(3H,7H)-dione (88 mg, 0.25 mmol), 1-(4-(tert-butyl)phenyl)-2-(piperazin-1-yl)ethanone, TFA (122 mg, 0.32 mmol), and TEA (0.14 mL, 1.0 mmol) in 2-methoxyethanol:H₂O (4:1, 1.25 mL) was heated at 130° C. for 16 h. The reaction was cooled to room temperature, diluted with saturated aqueous NaHCO₃ (5 mL), and extracted with DCM (3×5 mL). Combined organic layers were washed with brine (5 mL), dried over anhydrous Na₂SO₄, filtered, and concentrated in vacuo. The resulting product was purified via flash chromatography (0-5% MeOH/DCM) to give the desired compound 49 as a yellow solid. Yield: 63 mg (47%). ¹H NMR (400 MHz, DMSO-$d_6$) δ 10.93 (s, 1H), 7.93-7.88 (m, 2H), 7.55-7.49 (m, 2H), 7.34 (tdd, J=7.4, 5.4, 1.8 Hz, 1H), 7.21 (ddd, J=10.6, 8.3, 1.2 Hz, 1H), 7.14 (td, J=7.5, 1.2 Hz, 1H), 6.99 (td, J=7.7, 1.7 Hz, 1H), 5.38 (s, 2H), 3.84 (s, 2H), 3.32 (d, J=0.9 Hz, 3H), 3.16 (t, J=4.9 Hz, 4H), 2.57 (t, i. Step-1: Preparation of 2-(4-(bromomethyl)phenyl)propan-2-ol

To a solution of 1-(4-(bromomethyl)phenyl)ethanone (100 mg, 0.47 mmol) in THF (2 mL) at −78° C. was added a solution of 3 M Methylmagnesium bromide solution (0.23 mL, 0.70 mmol). The mixture was stirred for 30 min then warmed to room temperature and stirred overnight. The reaction was quenched with saturated NH₄Cl (4 mL), diluted with brine (4 mL), and extracted with EtOAc (3×10 mL). The organic layers were washed with water, dried over Na₂SO₄, filtered, and concentrated in vacuo. The crude was purified via flash chromatography (0-10% EtOAc/hexanes) to give the desired product (73 mg, 68%). ¹H NMR (400 MHz, CDCl₃) δ 7.49-7.44 (m, 2H), 7.39-7.34 (m, 2H), 4.50 (s, 2H), 1.58 (s, 6H).

ii. Step-2: Preparation of 7-(2-fluorobenzyl)-8-(4-(4-(2-hydroxypropan-2-yl)benzyl)piperazin-1-yl)-3-methyl-3,7-dihydro-1H-purine-2,6-dione (40)

To a solution of 7-(2-fluorobenzyl)-3-methyl-8-(piperazin-1-yl)-3,7-dihydro-1H-purine-2,6-dione (21) (100 mg, 0.28 mmol) and TEA (79 µL, 0.56 mmol) in dry DCM (4 mL) was added 2-(4-(bromomethyl)phenyl)propan-2-ol (70 mg, 0.31 mmol). After stirring at room temperature for 2 h, the reaction was diluted with H$_2$O (5 mL), extracted with DCM (2×10 mL), dried over Na$_2$SO$_4$, filtered, and concentrated in vacuo. The crude was purified via flash chromatography (0-10% MeOH/DCM) to give the desired compound 40 as a white solid. Yield: 44 mg (31%). $^1$H NMR (400 MHz, DMSO-d$_6$) δ 10.91 (s, 1H), 7.42-7.37 (m, 2H), 7.36-7.28 (m, 1H), 7.23-7.16 (m, 3H), 7.13 (td, J=7.5, 1.2 Hz, 1H), 7.01-6.94 (m, 1H), 5.36 (s, 2H), 4.93 (s, 1H), 3.44 (s, 2H), 3.32 (s, 3H), 3.14 (t, J=4.7 Hz, 4H), 2.38 (s, 4H), 1.40 (s, 6H). HR-ESIMS: m/z 507.2514 (M+H)$^+$ calcd. for C$_{27}$H$_{32}$FN$_6$O$_3$, found 507.2522. HPLC Purity=99% (Retention Time=8.3 min).

l. Synthesis of Compounds 43 and 44

DCM (3×3 mL). The organic layers were washed with brine (5 mL), dried over Na$_2$SO$_4$, filtered, and concentrated in vacuo.

8-(4-(2,5-Dimethylbenzoyl)piperazin-1-yl)-7-(2-fluorobenzyl)-3-methyl-3,7-dihydro-1H-purine-2,6-dione (43). Following the above procedure with 2,5-dimethylbenzoyl chloride (34 mg, 0.20 mmol), the crude material was purified via flash chromatography (0-70% EtOAc/hexanes) to give the desired compound 43 as a white solid. Yield: 60 mg (61%). $^1$H NMR (400 MHz, DMSO-d$_6$) δ 10.95 (s, 1H), 7.36-7.29 (m, 1H), 7.20 (ddd, J=10.6, 8.3, 1.2 Hz, 1H), 7.16-7.08 (m, 3H), 7.03-6.97 (m, 2H), 5.40 (s, 2H), 3.70 (s, 2H), 3.32 (s, 3H), 3.25-3.14 (m, 4H), 3.07 (s, 2H), 2.26 (d, J=0.8 Hz, 3H), 2.15 (s, 3H). HR-ESIMS: m/z 492.2227 (M+H)$^+$ calcd. for C$_{26}$H$_{28}$FN$_6$O$_3$, found 492.2230. HPLC Purity=99% (Retention Time=12.4 min).

8-(4-(4-(tert-Butyl)benzoyl)piperazin-1-yl)-7-(2-fluorobenzyl)-3-methyl-3,7-dihydro-1H-purine-2,6-dione (44). Following the above procedure with 4-(tert-butyl)benzoyl chloride (39 mg, 0.20 mmol), the crude material was purified

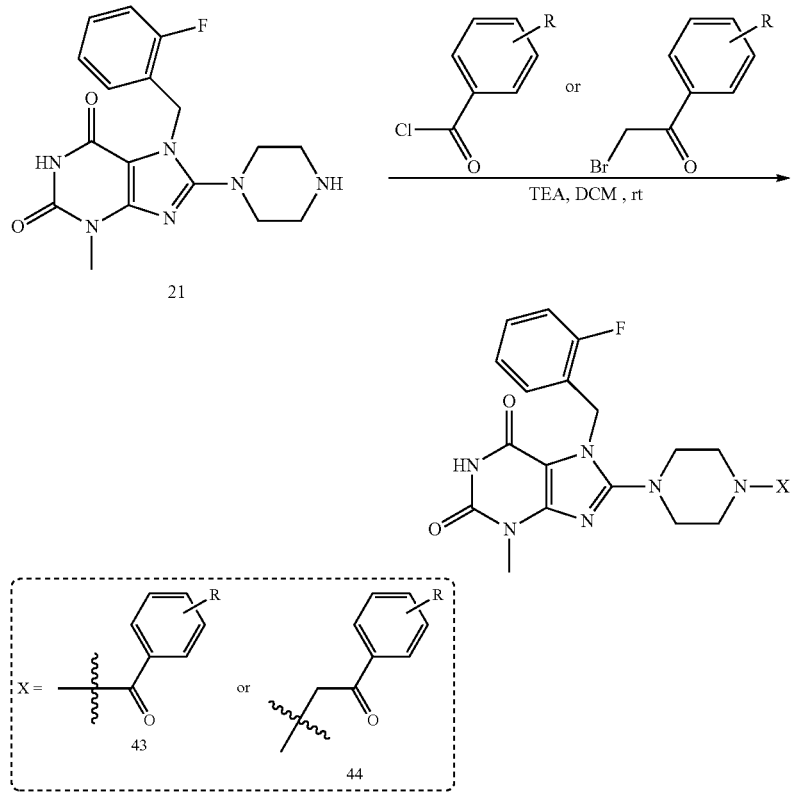

i. General Procedure to Compounds 43 and 44

To a solution 7-(2-fluorobenzyl)-3-methyl-8-(piperazin-1-yl)-1H-purine-2,6(3H,7H)-dione 21 (0.2 mmol) in DCM (2 mL) at 0° C. was added TEA (0.5 mmol) and appropriate benzoyl chloride (0.2 mmol) under argon. The reaction was warmed to room temperature and stirred overnight. The reaction was diluted with H$_2$O (5 mL) and extracted with via flash chromatography (0-70% EtOAc/hexanes) to give the desired compound 44 as a white solid. Yield: 86 mg (83%). $^1$H NMR (400 MHz, DMSO-d$_6$) δ 10.95 (s, 1H), 7.47-7.43 (m, 2H), 7.36-7.30 (m, 3H), 7.21 (ddd, J=10.5, 8.3, 1.2 Hz, 1H), 7.14 (td, J=7.5, 1.2 Hz, 1H), 7.01 (td, J=7.8, 1.7 Hz, 1H), 5.41 (s, 2H), 3.50 (s, 4H), 3.31 (s, 3H), 3.18 (s, 4H), 1.29 (s, 9H). HR-ESIMS: m/z 519.2514 (M+H)$^+$ calcd. for C$_{28}$H$_{32}$FN$_6$O$_3$, found 519.2517. HPLC Purity=98% (Retention Time=14.8 min).

m. Synthesis of 8-((2-((2,5-dimethylbenzyl)amino)ethyl)amino)-7-(2-fluorobenzyl)-3-methyl-3,7-dihydro-1H-purine-2,6-dione (63)

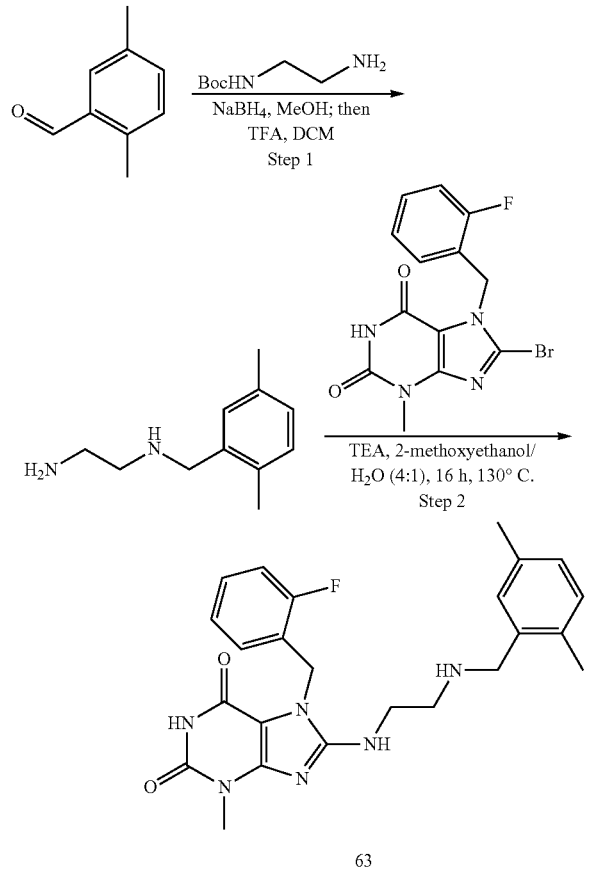

63 i. Step-1: Preparation of $N^1$-(2,5-dimethylbenzyl)ethane-1,2-diamine

To a solution of 2,5-dimethylbenzaldehyde (500 mg, 3.7 mmol) in MeOH (5 mL) was added tert-butyl (2-aminoethyl)carbamate (657 mg, 4.1 mmol) dropwise. The solution was stirred at room temperature overnight. The reaction was cooled to 0° C. and NaBH₄ (282 mg, 7.4 mmol) was added. The reaction was further stirred for 4 h and then quenched with H₂O (3 mL). Excess solvent was removed, and the remaining residue was extracted with DCM (3×10 mL). The organic layers were washed with brine, dried over Na₂SO₄, filtered, and concentrated in vacuo to give the desired carbamate as a clear oil. To a cooled solution of tert-butyl (2-((2,5-dimethylbenzyl)amino)ethyl)carbamate (100 mg, 0.36 mmol) in dry DCM (2 mL) was added TFA (0.83 mL, 11 mmol) dropwise under argon. The reaction was stirred at 0° C. for 30 min. then warmed to room temperature and stirred overnight. Upon completion, the solvent was removed and the crude was purified via flash chromatography (0-20% MeOH/DCM) to give the desired product as a TFA salt (100 mg, 95%). $^1$H NMR (400 MHz, CDCl₃) δ 7.09 (s, 1H), 7.03 (d, J=2.6 Hz, 2H), 4.02 (s, 2H), 3.47 (dd, J=4.3, 2.6 Hz, 2H), 3.28 (s, 4H), 2.23 (dd, J=9.0, 2.5 Hz, 6H).

ii. Step-2: Preparation of 8-((2-((2,5-dimethylbenzyl)amino)ethyl)amino)-7-(2-fluorobenzyl)-3-methyl-3,7-dihydro-1H-purine-2,6-dione (63)

A solution of 8-bromo-7-(2-fluorobenzyl)-3-methyl-1H-purine-2,6(3H,7H)-dione (88 mg, 0.25 mmol), $N^1$-(2,5-dimethylbenzyl)ethane-1,2-diamine, TFA (95 mg, 0.32 mmol), and TEA (0.12 mL, 0.87 mmol) in 2-methoxyethanol:H₂O (4:1, 1 mL) was heated at 130° C. for 16 h. The reaction was cooled to room temperature, diluted with saturated aqueous NaHCO₃ (5 mL), and extracted with DCM (3×5 mL). Combined organic layers were washed with brine (5 mL), dried over anhydrous Na₂SO₄, filtered, and concentrated in vacuo. The resulting product was purified via flash chromatography (0-5% MeOH/DCM) to give the desired compound 63 as a light-tan solid. Yield: 26 mg (23%). $^1$H NMR (400 MHz, DMSO-d₆) δ 10.61 (s, 1H), 7.30 (tdd, J=7.4, 5.4, 1.7 Hz, 1H), 7.20 (ddd, J=10.6, 8.2, 1.2 Hz, 1H), 7.09-7.06 (m, 1H), 7.05-7.03 (m, 1H), 6.99 (d, J=7.6 Hz, 1H), 6.90 (dd, J=7.6, 1.9 Hz, 1H), 6.76 (td, J=7.8, 1.7 Hz, 1H), 5.33 (s, 2H), 3.61 (s, 2H), 3.45 (q, J=6.0 Hz, 2H), 3.29 (s, 3H), 2.72 (t, J=6.3 Hz, 2H), 2.20 (d, J=5.1 Hz, 6H). HR-ESIMS: m/z 451.2252 (M+H)⁺ calcd. for $C_{24}H_{28}FN_6O_2$, found 451.2252. HPLC Purity=96% (Retention Time=9.3 min).

n. Synthesis of 8-(4-(4-(tert-butyl)benzyl)piperazin-1-yl)-7-(2-fluorobenzyl)-3,7-dihydro-1H-purine-2,6-dione (64)

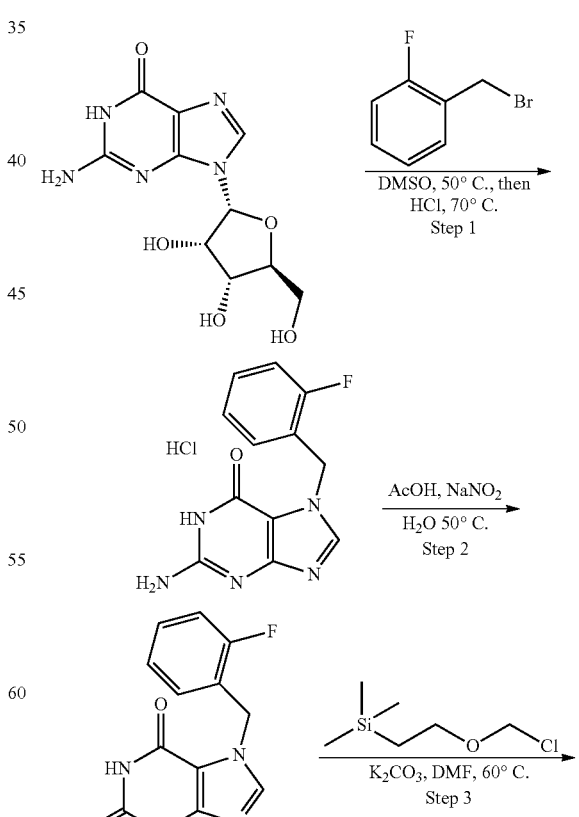

117

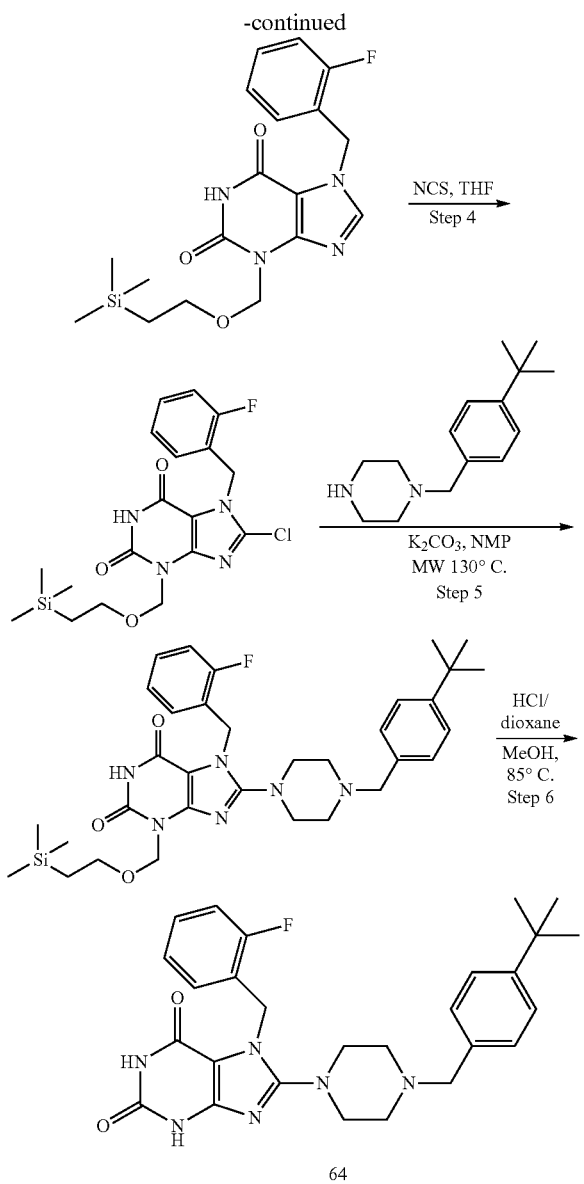

64 i. Step-1: Preparation of 2-amino-7-(2-fluorobenzyl)-1,7-dihydro-6H-purin-6-one Guanosine (1.0 g, 3.5 mmol) was dissolved in DMSO (5 mL) at 70° C. After cooling to room temperature, 1-(bromomethyl)-2-fluoro-benzene (1.1 mL, 8.8 mmol) was added in one portion and the solution was stirred at room temperature in a sealed flask for 4 h. Concentrated HCl (2.5 mL) was added to the stirred solution in one portion without cooling. After stirring for an additional 1 h, the reaction mixture was poured into well-stirred cold methanol (−10° C., 30 mL). The slowly formed white precipitate was filtered off and washed with cold MeOH to give the desired product (668 mg, 64%) as an HCl salt. $^1$H NMR (400 MHz, DMSO-d$_6$) δ 8.76 (s, 1H), 7.56 (s, 2H), 7.41 (dddd, J=8.3, 7.3, 5.5, 1.9 Hz, 1H), 7.33-7.22 (m, 2H), 7.19 (td, J=7.5, 1.2 Hz, 1H), 5.59 (s, 2H).

118 ii. Step-2: Preparation of 7-(2-fluorobenzyl)-3,7-dihydro-1H-purine-2,6-dione 2-amino-7-((2-fluorophenyl)methyl)-1H-purin-6-one (668 mg, 2.3 mmol) was dissolved in a mixture of acetic acid (15 mL) and water (2.5 mL) at 100° C. After cooling to 50° C., sodium nitrite (623 mg, 9.0 mmol) in water (2.5 mL) was added dropwise and stirring was continued for 4 h at room temperature. The precipitate formed up cooling and was collected by filtration, washed with Et$_2$O and dried under vacuum to give the desired product (303 mg, 51%) as a white solid. $^1$H NMR (400 MHz, DMSO-d$_6$) δ 11.71 (s, 1H), 10.87 (s, 1H), 8.03 (d, J=0.9 Hz, 1H), 7.41-7.34 (m, 1H), 7.26-7.20 (m, 1H), 7.19-7.14 (m, 2H), 5.50 (s, 2H).

iii. Step-3: Preparation of 7-(2-fluorobenzyl)-3-((2-(trimethylsilyl)ethoxy)methyl)-3,7-dihydro-1H-purine-2,6-dione A solution of 7-((2-fluorophenyl)methyl)-3H-purine-2,6-dione (600 mg, 2.3 mmol), 2-(trimethylsilyl)ethoxymethyl chloride (0.61 mL, 3.5 mmol), and K$_2$CO$_3$ (1.1 g, 8.1 mmol) in DMF (8 mL) was heated at 80° C. and stirred overnight. Upon completion, the reaction was cooled to room temperature, diluted with H$_2$O (8 mL), and extracted with EtOAc (3×20 mL). The crude was purified via flash chromatography (0-50% EtOAc/hexanes) to give the desired product (283 mg, 31%) as a beige solid.

iv. Step-4: Preparation of 8-chloro-7-(2-fluorobenzyl)-3-((2-(trimethylsilyl)ethoxy)methyl)-3,7-dihydro-1H-purine-2,6-dione To a solution of 7-((2-fluorophenyl)methyl)-3-(2-trimethylsilylethoxymethyl)purine-2,6-dione (230 mg, 0.59 mmol) in THF (4 mL) at 0° C. was added N-chlorosuccinimide (118 mg, 0.88 mmol) slowly. The reaction was stirred for 1 h before warming to room temperature and stirred overnight. Upon completion, solvent was evaporated and the crude was purified via flash chromatography (0-35% EtOAc/hexanes) to give the desired product (220 mg, 88%) as a white solid. $^1$H NMR (400 MHz, DMSO-d$_6$) δ 11.45 (s, 1H), 7.43-7.36 (m, 1H), 7.26 (ddd, J=10.7, 8.4, 1.2 Hz, 1H), 7.18 (td, J=7.5, 1.2 Hz, 1H), 7.09 (td, J=7.7, 1.8 Hz, 1H), 5.56 (s, 2H), 5.28 (s, 2H), 3.68-3.59 (m, 2H), 0.90-0.81 (m, 2H), −0.06 (s, 9H).

v. Step-5: Preparation of 8-(4-(4-(tert-butyl)benzyl)piperazin-1-yl)-7-(2-fluorobenzyl)-3-((2-(trimethylsilyl)ethoxy)methyl)-3,7-dihydro-1H-purine-2,6-dione A solution of 8-chloro-7-((2-fluorophenyl)methyl)-3-(2-trimethylsilylethoxymethyl)purine-2,6-dione (315 mg, 0.74 mmol), 1-((4-tert-butylphenyl)methyl)piperazine (258 mg, 1.1 mmol), and K$_2$CO$_3$ (205 mg, 1.5 mmol) in NMP (7 mL) was irradiated at 140° C. under microwave conditions for 3 h. Upon completion, the reaction was diluted with water (10 mL) and extracted with EtOAc (3×10 mL). The organic layers were washed with brine (10 mL), dried over Na$_2$SO$_4$, filtered, and concentrated in vacuo. The crude was purified via flash chromatography (0-35% EtOAc/hexanes) to the desired product (218 mg, 47%). $^1$H NMR (400 MHz, DMSO-d$_6$) δ 10.99 (s, 1H), 7.34-7.31 (m, 3H), 7.22-7.18 (m, 3H), 7.12 (td, J=7.5, 1.2 Hz, 1H), 6.95 (t, J=7.6 Hz, 1H), 5.37 (s, 2H), 5.28 (s, 2H), 3.68-3.61 (m, 2H), 3.14 (t, J=4.9 Hz, 4H), 2.36 (d, J=5.0 Hz, 5H), 1.26 (s, 9H), 0.91-0.81 (m, 2H), -0.06 (s, 9H).

vi. Step-6: Preparation of 8-(4-(4-(tert-butyl)benzyl)piperazin-1-yl)-7-(2-fluorobenzyl)-3,7-dihydro-1H-purine-2,6-dione (64)

To a solution of 8-(4-(4-(tert-butyl)benzyl)piperazin-1-yl)-7-(2-fluorobenzyl)-3-((2-(trimethylsilyl)ethoxy)methyl)-3,7-dihydro-1H-purine-2,6-dione (180 mg, 0.29 mmol) in methanol (1.5 mL) was added 4M HCl in dioxane (0.72 mL, 2.9 mmol). The reaction was heated at 85° C. and stirred overnight. Upon completion, the solvent was removed and the solids were dissolved in $H_2O$ (pH=3-5). The aqueous layer was basified with 1N NaOH and extracted with DCM (3×5 mL). The organic layers were washed with brine, dried over $Na_2SO_4$, filtered and concentrated in vacuo. The off-white solids were titurated with $Et_2O$ to give the desired compound 64. Yield: 86 mg (60%). $^1H$ NMR (400 MHz, DMSO-$d_6$) δ 11.58 (d, J=1.7 Hz, 1H), 10.73-10.67 (m, 1H), 7.50 (q, J=8.2 Hz, 4H), 7.35-7.26 (m, 1H), 7.18 (ddd, J=9.6, 8.3, 1.1 Hz, 1H), 7.11 (td, J=7.6, 1.2 Hz, 1H), 6.93 (dd, J=8.5, 6.9 Hz, 1H), 5.36 (s, 2H), 4.30 (d, J=5.1 Hz, 2H), 3.49 (d, J=13.3 Hz, 2H), 3.39 (s, 1H), 3.34-3.27 (m, 3H), 3.08 (d, J=11.4 Hz, 2H), 1.29 (s, 9H). HR-ESIMS: m/z 491.2565 (M+H)$^+$ calcd. for $C_{27}H_{32}FN_6O_2$, found 491.2564. HPLC Purity=95% (Retention Time=11.2 min).

3. Evaluation of Xanthine Analogs for Antiviral Activity

A summary of the anti-West Nile virus activity of representative xanthine analogs is shown in Table 1 below.

TABLE 1

| No. | Structure | MW | $EC_{90}$ (μM)* | $CC_{50}$ (μM)* |
|---|---|---|---|---|
| 1 | 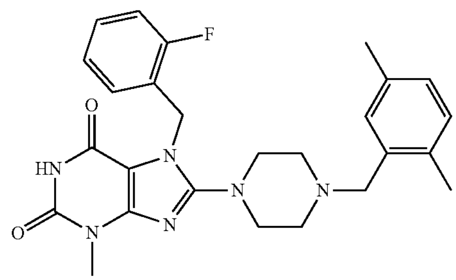 [SMILES: Cc1ccc(C)c(CN2CCN(c3nc4c(c(=O)[nH]c(=O)n4C)n3Cc3ccccc3F)CC2)c1] | 476.56 | 1.2 | 12 |
| 2 | 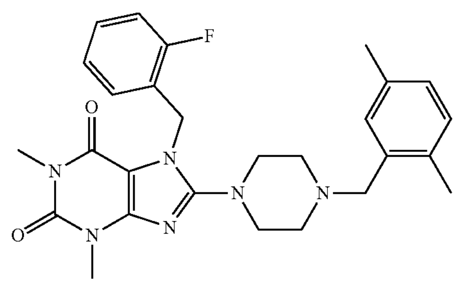 [SMILES: Cc1ccc(C)c(CN2CCN(c3nc4c(c(=O)n(C)c(=O)n4C)n3Cc3ccccc3F)CC2)c1] | 490.58 | 1.1 | >40 |
| 3 | 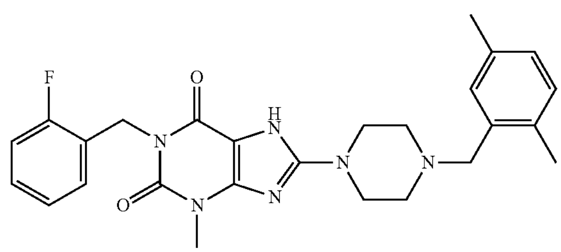 [SMILES: Cc1ccc(C)c(CN2CCN(c3nc4c([nH]3)c(=O)n(Cc3ccccc3F)c(=O)n4C)CC2)c1] | 476.56 | >10 | >40 |
| 4 | 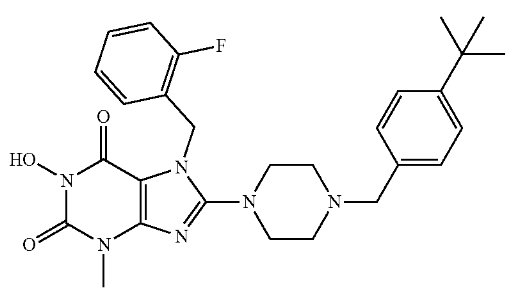 [SMILES: Cn1c(=O)n(O)c(=O)c2c1nc(N1CCN(Cc3ccc(C(C)(C)C)cc3)CC1)n2Cc1ccccc1F] | 520.61 | >30 | >40 |

TABLE 1-continued

| No. | Structure | MW | EC$_{90}$ (μM)* | CC$_{50}$ (μM)* |
|---|---|---|---|---|
| 5 | 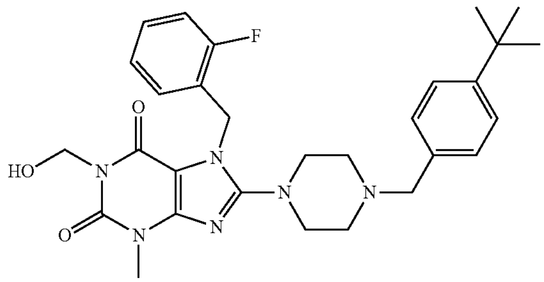 [SMILES: Cn1c(=O)n(CO)c(=O)c2c1nc(N1CCN(Cc3ccc(C(C)(C)C)cc3)CC1)n2Cc1ccccc1F] | 534.64 | 1.2 | 16.8 |
| 6 | 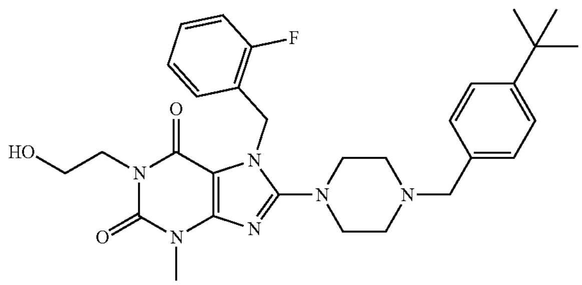 [SMILES: Cn1c(=O)n(CCO)c(=O)c2c1nc(N1CCN(Cc3ccc(C(C)(C)C)cc3)CC1)n2Cc1ccccc1F] | 548.66 | 6 | 12 |
| 7 | 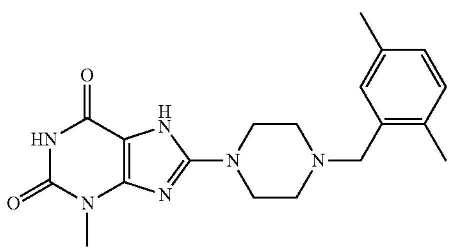 [SMILES: Cc1ccc(C)c(CN2CCN(c3nc4c([nH]3)c(=O)[nH]c(=O)n4C)CC2)c1] | 368.44 | >10 | ND |
| 8 | 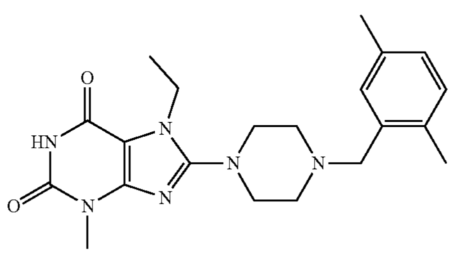 [SMILES: CCn1c(N2CCN(Cc3cc(C)ccc3C)CC2)nc2c1c(=O)[nH]c(=O)n2C] | 396.5 | >10 | >40 |
| 9 | 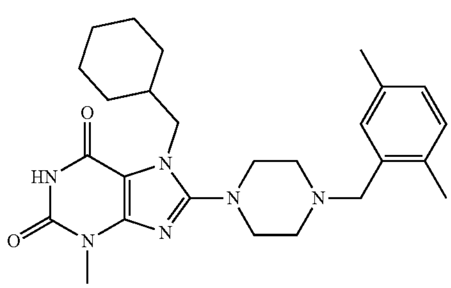 [SMILES: Cc1ccc(C)c(CN2CCN(c3nc4c(c(=O)[nH]c(=O)n4C)n3CC3CCCCC3)CC2)c1] | 464.61 | 4.4 | >40 |

TABLE 1-continued

| No. | Structure | MW | EC$_{90}$ (μM)* | CC$_{50}$ (μM)* |
|---|---|---|---|---|
| 10 | 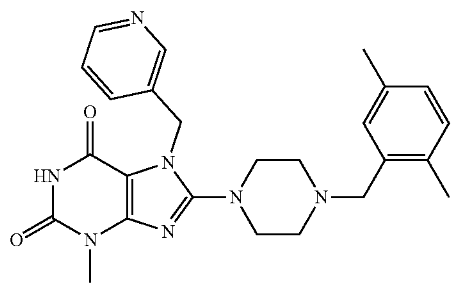 [SMILES: Cc1ccc(C)c(CN2CCN(c3nc4c(c(=O)[nH]c(=O)n4C)n3Cc3cccnc3)CC2)c1] | 459.55 | >10 | ND |
| 11 | 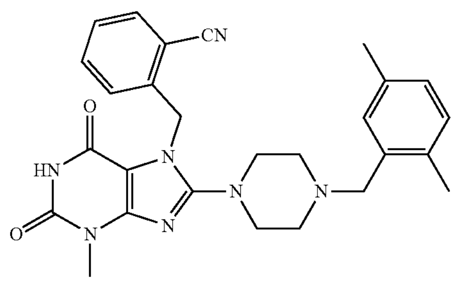 [SMILES: Cc1ccc(C)c(CN2CCN(c3nc4c(c(=O)[nH]c(=O)n4C)n3Cc3ccccc3C#N)CC2)c1] | 483.58 | 6.9 | >30 |
| 12 | 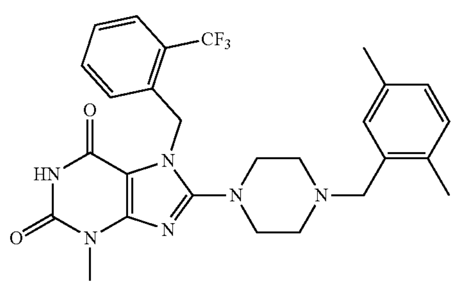 [SMILES: Cc1ccc(C)c(CN2CCN(c3nc4c(c(=O)[nH]c(=O)n4C)n3Cc3ccccc3C(F)(F)F)CC2)c1] | 526.56 | 1.1 | 12.0 |
| 13 | 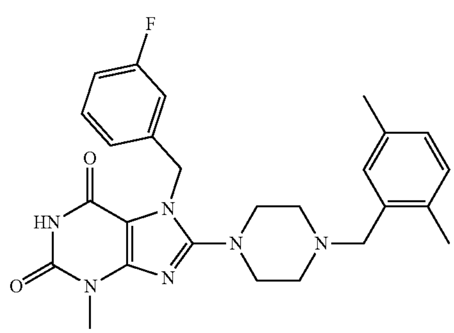 [SMILES: Cc1ccc(C)c(CN2CCN(c3nc4c(c(=O)[nH]c(=O)n4C)n3Cc3cccc(F)c3)CC2)c1] | 476.56 | 5.7 | >30 |
| 14 | 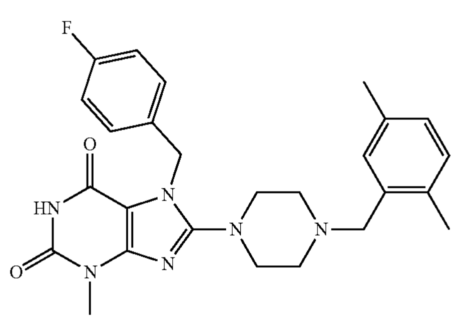 [SMILES: Cc1ccc(C)c(CN2CCN(c3nc4c(c(=O)[nH]c(=O)n4C)n3Cc3ccc(F)cc3)CC2)c1] | 476.56 | 6.1 | >30 |

TABLE 1-continued

| No. | Structure | MW | EC$_{90}$ (μM)* | CC$_{50}$ (μM)* |
|---|---|---|---|---|
| 15 | 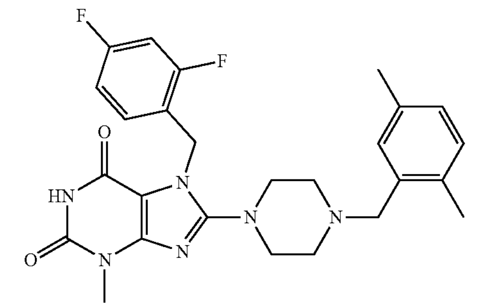 [SMILES: Cc1ccc(C)c(CN2CCN(c3nc4c(c(=O)[nH]c(=O)n4C)n3Cc3ccc(F)cc3F)CC2)c1] | 494.55 | >10 | >40 |
| 16 | 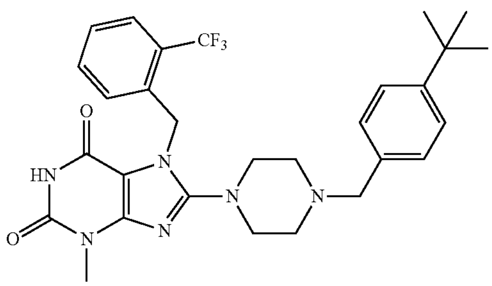 | 554.62 | 1.2 | 12.4 |
| 17 | 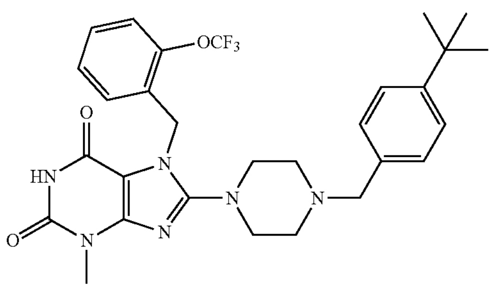 [SMILES: Cn1c(=O)[nH]c(=O)c2c1nc(N1CCN(Cc3ccc(C(C)(C)C)cc3)CC1)n2Cc1ccccc1OC(F)(F)F] | 570.62 | 1.2 | 10.2 |
| 18 | 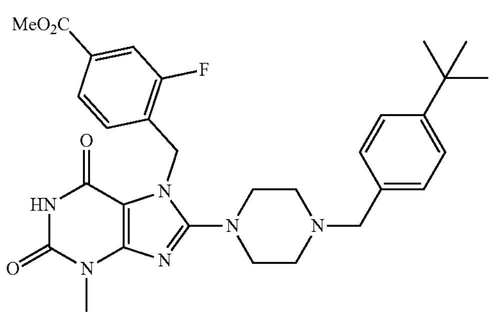 [SMILES: COC(=O)c1ccc(Cn2c(N3CCN(Cc4ccc(C(C)(C)C)cc4)CC3)nc3c2c(=O)[nH]c(=O)n3C)c(F)c1] | 562.65 | 5.2 | 21.4 |
| 19 | 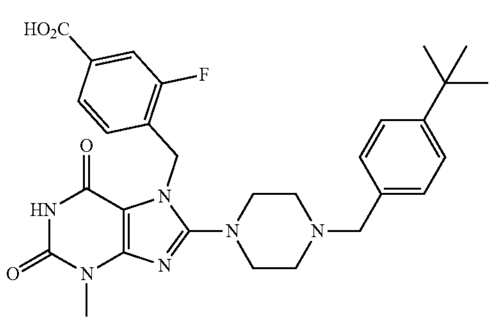 [SMILES: Cn1c(=O)[nH]c(=O)c2c1nc(N1CCN(Cc3ccc(C(C)(C)C)cc3)CC1)n2Cc1ccc(C(=O)O)cc1F] | 548.62 | >10 | >40 |

TABLE 1-continued
| No. | Structure | MW | EC$_{90}$ (μM)* | CC$_{50}$ (μM)* |
|---|---|---|---|---|
| 20 | 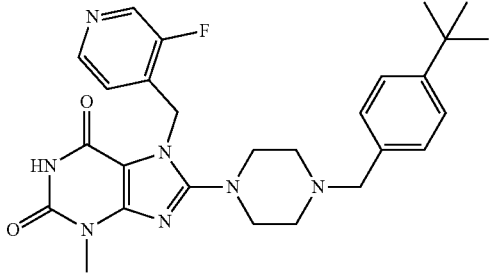 [SMILES: Cn1c(=O)[nH]c(=O)c2c1nc(N1CCN(Cc3ccc(C(C)(C)C)cc3)CC1)n2Cc1ccncc1F] | 505.6 | 2.6 | 22.1 |
| 21 | 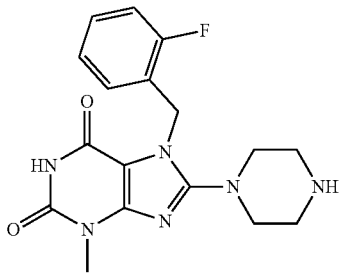 [SMILES: Cn1c(=O)[nH]c(=O)c2c1nc(N1CCNCC1)n2Cc1ccccc1F] | 358.38 | >10 | ND |
| 22 | 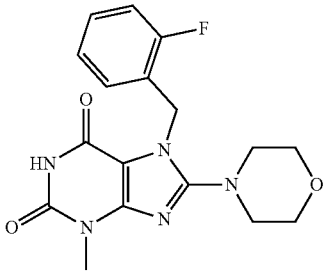 [SMILES: Cn1c(=O)[nH]c(=O)c2c1nc(N1CCOCC1)n2Cc1ccccc1F] | 359.36 | >10 | >40 |
| 23 | 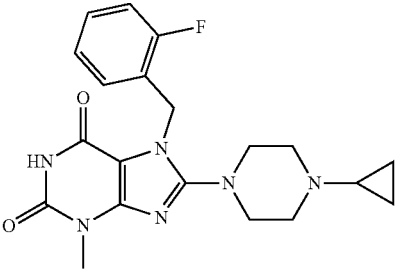 [SMILES: Cn1c(=O)[nH]c(=O)c2c1nc(N1CCN(C3CC3)CC1)n2Cc1ccccc1F] | 398.44 | >10 | ND |
| 24 | 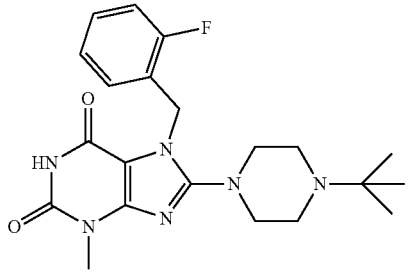 [SMILES: Cn1c(=O)[nH]c(=O)c2c1nc(N1CCN(C(C)(C)C)CC1)n2Cc1ccccc1F] | 414.49 | >10 | ND |

TABLE 1-continued

| No. | Structure | MW | EC$_{90}$ (μM)* | CC$_{50}$ (μM)* |
|---|---|---|---|---|
| 25 | 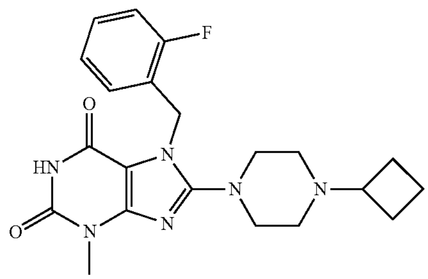 [SMILES: Cn1c(=O)[nH]c(=O)c2c1nc(N1CCN(C3CCC3)CC1)n2Cc1ccccc1F] | 412.47 | >10 | ND |
| 26 | 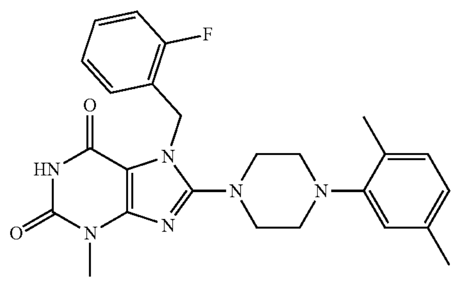 [SMILES: Cc1ccc(C)c(N2CCN(c3nc4c(c(=O)[nH]c(=O)n4C)n3Cc3ccccc3F)CC2)c1] | 462.53 | 4.5 | 2.8 |
| 27 | 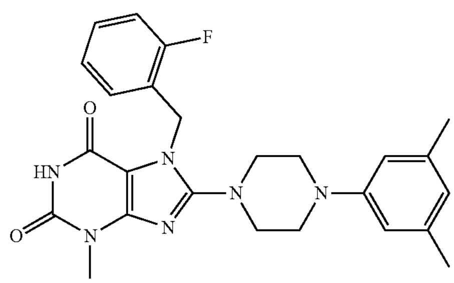 [SMILES: Cc1cc(C)cc(N2CCN(c3nc4c(c(=O)[nH]c(=O)n4C)n3Cc3ccccc3F)CC2)c1] | 462.53 | 10 | >30 |
| 28 | 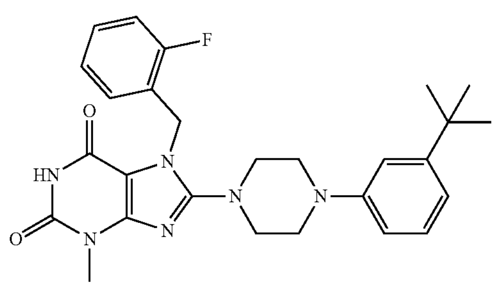 [SMILES: Cn1c(=O)[nH]c(=O)c2c1nc(N1CCN(c3cccc(C(C)(C)C)c3)CC1)n2Cc1ccccc1F] | 490.58 | 10 | >40 |
| 29 | 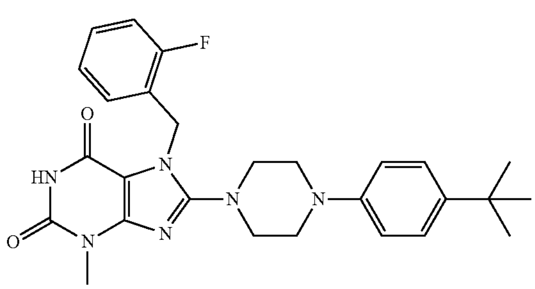 [SMILES: Cn1c(=O)[nH]c(=O)c2c1nc(N1CCN(c3ccc(C(C)(C)C)cc3)CC1)n2Cc1ccccc1F] | 490.58 | >10 | ND |

TABLE 1-continued
| No. | Structure | MW | EC$_{90}$ (μM)* | CC$_{50}$ (μM)* |
|---|---|---|---|---|
| 30 | 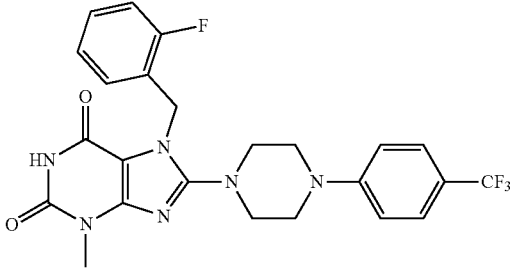 [SMILES: Cn1c(=O)[nH]c(=O)c2c1nc(N1CCN(c3ccc(C(F)(F)F)cc3)CC1)n2Cc1ccccc1F] | 502.47 | 6.5 | 12.9 |
| 31 | 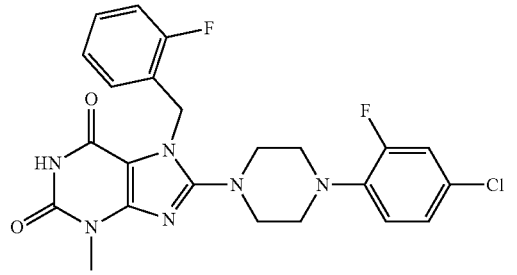 [SMILES: Cn1c(=O)[nH]c(=O)c2c1nc(N1CCN(c3ccc(Cl)cc3F)CC1)n2Cc1ccccc1F] | 486.91 | >10 | ND |
| 32 | 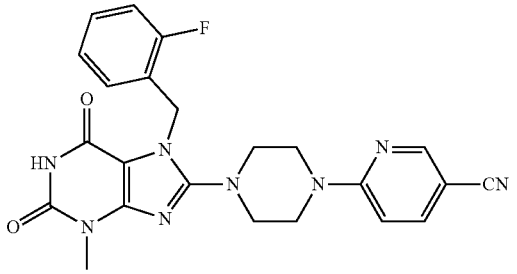 | 460.47 | >10 | ND |
| 33 | 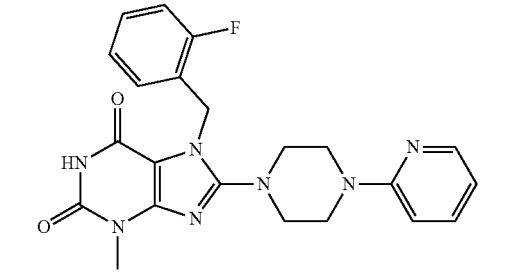 | 435.46 | >10 | ND |
| 34 | 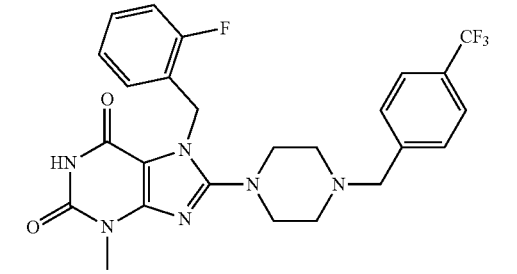 [SMILES: Cn1c(=O)[nH]c(=O)c2c1nc(N1CCN(Cc3ccc(C(F)(F)F)cc3)CC1)n2Cc1ccccc1F] | 516.5 | 9.4 | >30 |

TABLE 1-continued

| No. | Structure | MW | EC$_{90}$ (μM)* | CC$_{50}$ (μM)* |
|---|---|---|---|---|
| 35 | 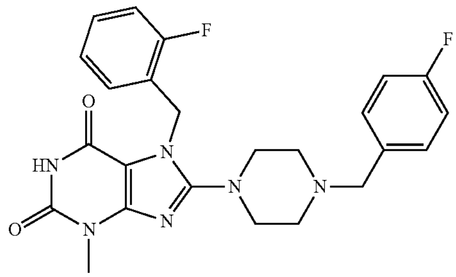 | 466.49 | 10.5 | >30 |
| 36 | 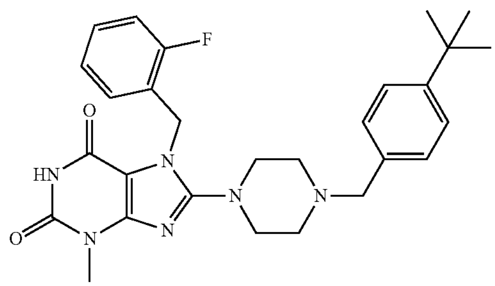 [SMILES: Cn1c(=O)[nH]c(=O)c2c1nc(N1CCN(Cc3ccc(C(C)(C)C)cc3)CC1)n2Cc1ccccc1F] | 504.61 | 0.87 | >30 |
| 37 | 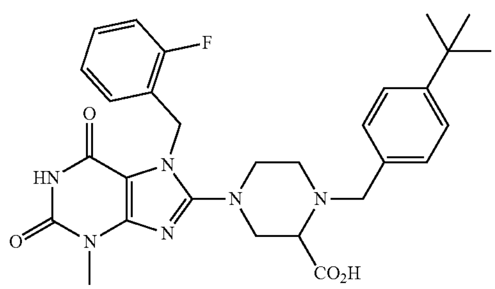 [SMILES: Cn1c(=O)[nH]c(=O)c2c1nc(N1CCN(Cc3ccc(C(C)(C)C)cc3)C(C(=O)O)C1)n2Cc1ccccc1F] | 548.62 | >10 | >40 |
| 38 | 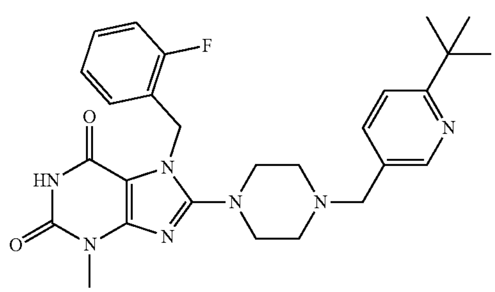 [SMILES: Cn1c(=O)[nH]c(=O)c2c1nc(N1CCN(Cc3ccc(C(C)(C)C)nc3)CC1)n2Cc1ccccc1F] | 505.6 | 16 | 34.2 |
| 39 | 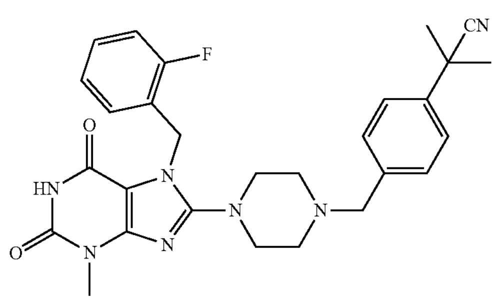 | 515.59 | >30 | >40 |

TABLE 1-continued

| No. | Structure | MW | EC$_{90}$ (µM)* | CC$_{50}$ (µM)* |
|---|---|---|---|---|
| 40 | 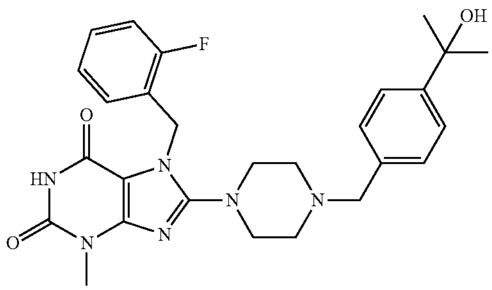 [SMILES: Cn1c(=O)[nH]c(=O)c2c1nc(N1CCN(Cc3ccc(C(C)(C)C#N)cc3)CC1)n2Cc1ccccc1F] | 506.58 | >10 | >40 |
| 41 | 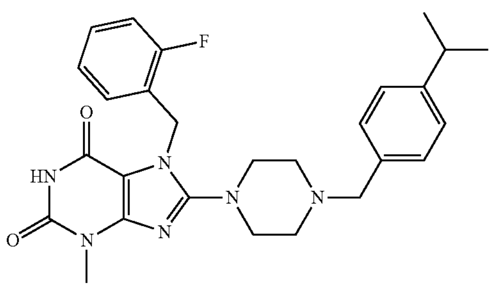 [SMILES: CC(C)c1ccc(CN2CCN(c3nc4c(c(=O)[nH]c(=O)n4C)n3Cc3ccccc3F)CC2)cc1] | 490.58 | 1.1 | 24 |
| 42 | 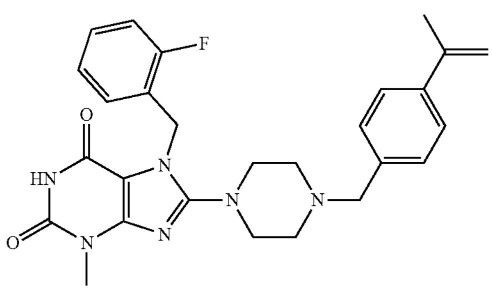 [SMILES: C=C(C)c1ccc(CN2CCN(c3nc4c(c(=O)[nH]c(=O)n4C)n3Cc3ccccc3F)CC2)cc1] | 488.57 | 2.1 | 22 |
| 43 | 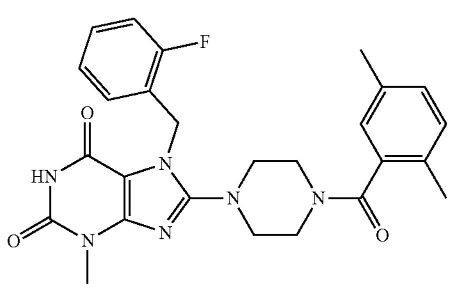 [SMILES: Cc1ccc(C)c(C(=O)N2CCN(c3nc4c(c(=O)[nH]c(=O)n4C)n3Cc3ccccc3F)CC2)c1] | 490.54 | >10 | >40 |
| 44 | 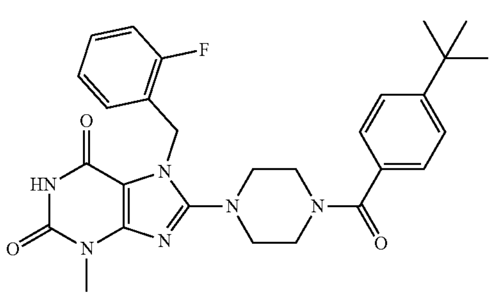 [SMILES: Cn1c(=O)[nH]c(=O)c2c1nc(N1CCN(C(=O)c3ccc(C(C)(C)C)cc3)CC1)n2Cc1ccccc1F] | 518.59 | 8.8 | >30 |

TABLE 1-continued

| No. | Structure | MW | EC$_{90}$ (μM)* | CC$_{50}$ (μM)* |
|---|---|---|---|---|
| 45 | 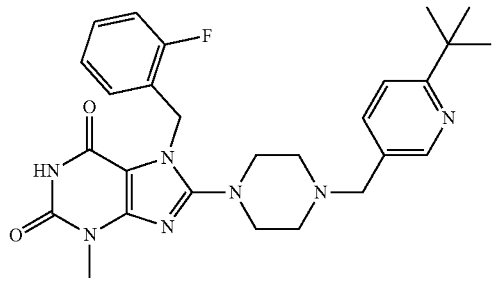 [SMILES: Cn1c(=O)[nH]c(=O)c2c1nc(N1CCN(Cc3ccc(C(C)(C)C)nc3)CC1)n2Cc1ccccc1F] | 519.58 | >10 | ND |
| 46 | 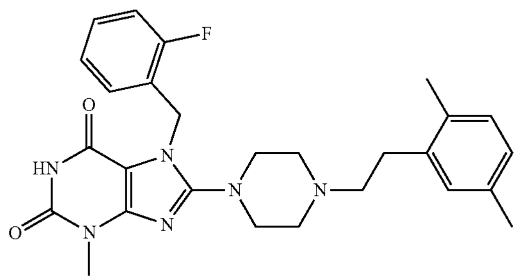 [SMILES: Cc1ccc(C)c(CCN2CCN(c3nc4c(c(=O)[nH]c(=O)n4C)n3Cc3ccccc3F)CC2)c1] | 490.58 | 10.2 | ND |
| 47 | 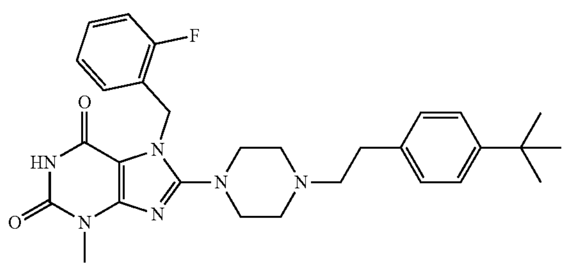 [SMILES: Cn1c(=O)[nH]c(=O)c2c1nc(N1CCN(CCc3ccc(C(C)(C)C)cc3)CC1)n2Cc1ccccc1F] | 518.64 | 13.6 | ND |
| 48 | 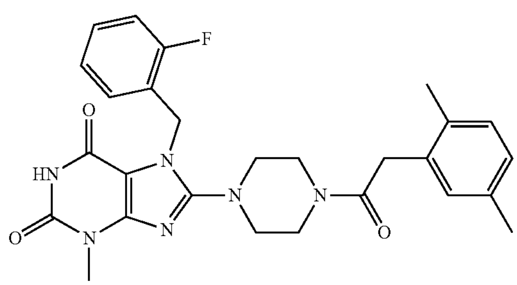 [SMILES: Cc1ccc(C)c(CC(=O)N2CCN(c3nc4c(c(=O)[nH]c(=O)n4C)n3Cc3ccccc3F)CC2)c1] | 504.57 | >10 | ND |
| 49 | 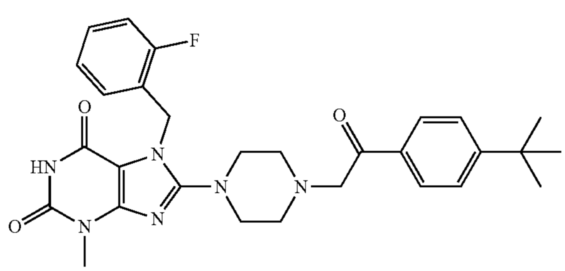 [SMILES: Cn1c(=O)[nH]c(=O)c2c1nc(N1CCN(CC(=O)c3ccc(C(C)(C)C)cc3)CC1)n2Cc1ccccc1F] | 532.62 | >10 | ND |

TABLE 1-continued

| No. | Structure | MW | EC$_{90}$ (μM)* | CC$_{50}$ (μM)* |
|---|---|---|---|---|
| 50 | 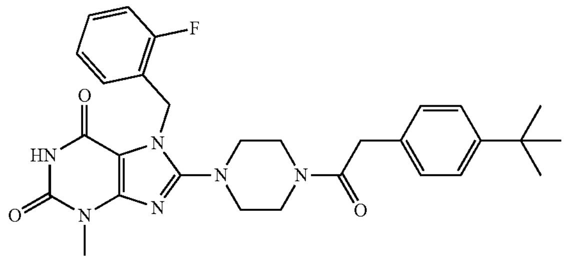 [SMILES: Cn1c(=O)[nH]c(=O)c2c1nc(N1CCN(C(=O)Cc3ccc(C(C)(C)C)cc3)CC1)n2Cc1ccccc1F] | 532.62 | 3.7 | >30 |
| 51 | 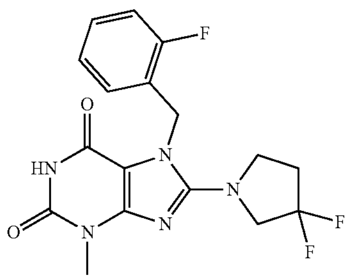 [SMILES: Cn1c(=O)[nH]c(=O)c2c1nc(N1CCC(F)(F)C1)n2Cc1ccccc1F] | 379.34 | >10 | ND |
| 52 | 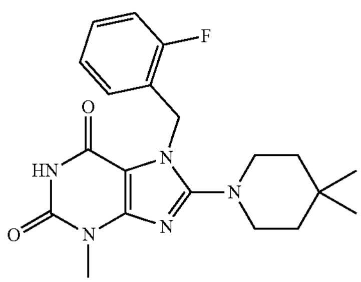 [SMILES: Cn1c(=O)[nH]c(=O)c2c1nc(N1CCC(C)(C)CC1)n2Cc1ccccc1F] | 385.44 | 3.9 | >30 |
| 53 | 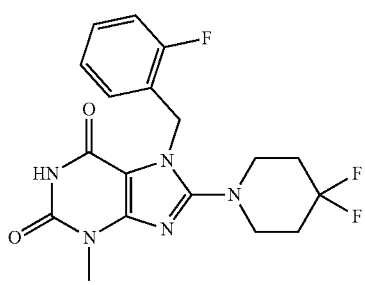 [SMILES: Cn1c(=O)[nH]c(=O)c2c1nc(N1CCC(F)(F)CC1)n2Cc1ccccc1F] | 393.37 | >10 | ND |
| 54 | 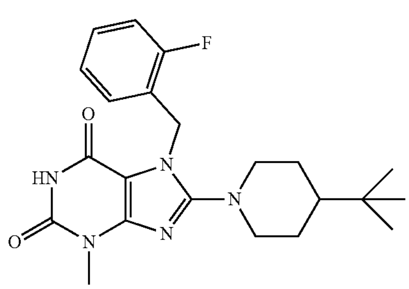 [SMILES: Cn1c(=O)[nH]c(=O)c2c1nc(N1CCC(C(C)(C)C)CC1)n2Cc1ccccc1F] | 413.5 | 1.5 | 22<br>20 |

TABLE 1-continued

| No. | Structure | MW | EC$_{90}$ (μM)* | CC$_{50}$ (μM)* |
|---|---|---|---|---|
| 55 | 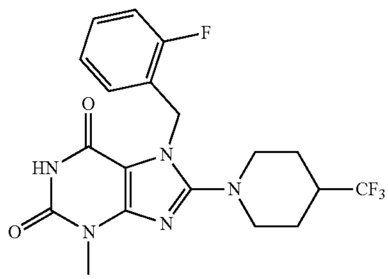 [SMILES: Cn1c(=O)[nH]c(=O)c2c1nc(N1CCC(C(F)(F)F)CC1)n2Cc1ccccc1F] | 425.39 | >10 | ND |
| 56 | 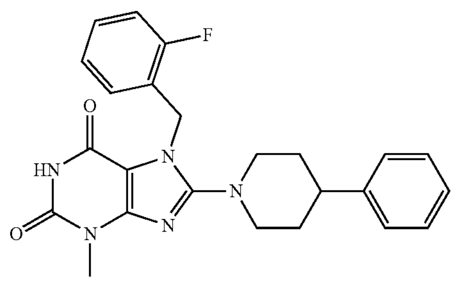 [SMILES: Cn1c(=O)[nH]c(=O)c2c1nc(N1CCC(c3ccccc3)CC1)n2Cc1ccccc1F] | 433.49 | 2.4 | 10.7 |
| 57 | 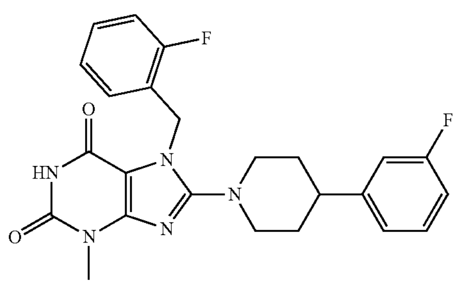 [SMILES: Cn1c(=O)[nH]c(=O)c2c1nc(N1CCC(c3cccc(F)c3)CC1)n2Cc1ccccc1F] | 451.48 | 4.4 | >30 |
| 58 | 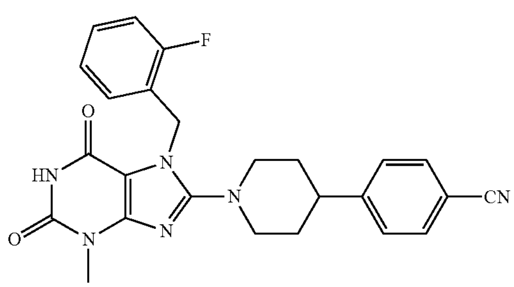 [SMILES: Cn1c(=O)[nH]c(=O)c2c1nc(N1CCC(c3ccc(C#N)cc3)CC1)n2Cc1ccccc1F] | 458.5 | >10 | ND |
| 59 | 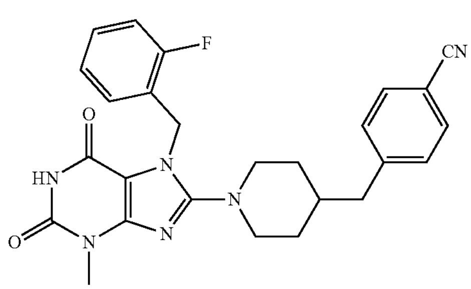 [SMILES: Cn1c(=O)[nH]c(=O)c2c1nc(N1CCC(Cc3ccc(C#N)cc3)CC1)n2Cc1ccccc1F] | 472.52 | >10 | ND |

TABLE 1-continued

| No. | Structure | MW | EC$_{90}$ (μM)* | CC$_{50}$ (μM)* |
|---|---|---|---|---|
| 60 | 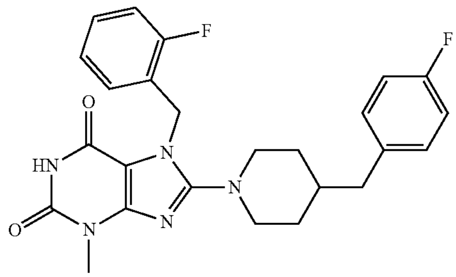 [SMILES: Cn1c(=O)[nH]c(=O)c2c1nc(N1CCC(Cc3ccc(F)cc3)CC1)n2Cc1ccccc1F] | 465.5 | >10 | ND |
| 61 | 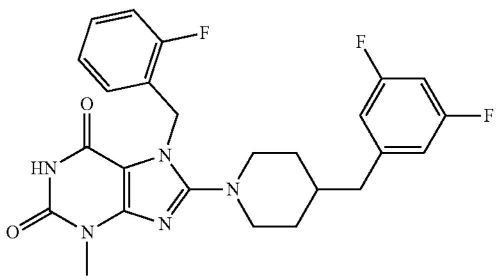 [SMILES: Cn1c(=O)[nH]c(=O)c2c1nc(N1CCC(Cc3cc(F)cc(F)c3)CC1)n2Cc1ccccc1F] | 483.5 | >10 | ND |
| 62 | 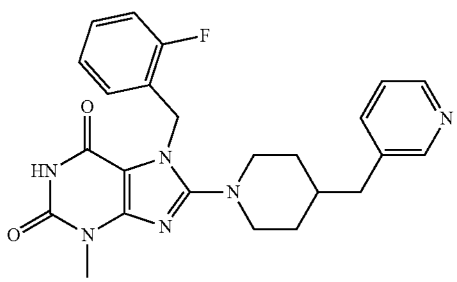 [SMILES: Cn1c(=O)[nH]c(=O)c2c1nc(N1CCC(Cc3cccnc3)CC1)n2Cc1ccccc1F] | 448.5 | 12.4 | ND |
| 63 | 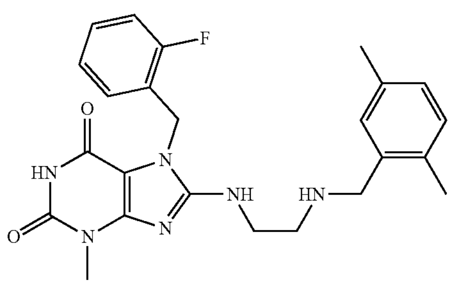 [SMILES: Cc1ccc(C)c(CNCCNc2nc3c(c(=O)[nH]c(=O)n3C)n2Cc2ccccc2F)c1] | 450.52 | >10 | ND |
| 64 | 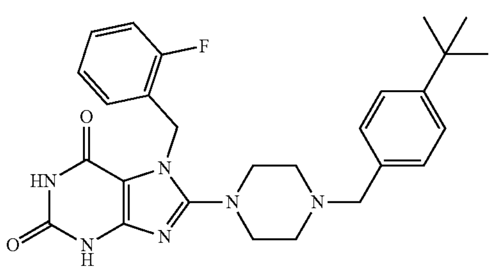 [SMILES: CC(C)(C)c1ccc(CN2CCN(c3nc4[nH]c(=O)[nH]c(=O)c4n3Cc3ccccc3F)CC2)cc1] | 490.58 | 9 | 10 |

*Tested in HEK293 cells; EC$_{90}$ = effective concentration to inhibit 90% of virus; in cell viability assay 50% cytotoxicity concentration (CC$_{50}$); ND = Not Determined It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure:

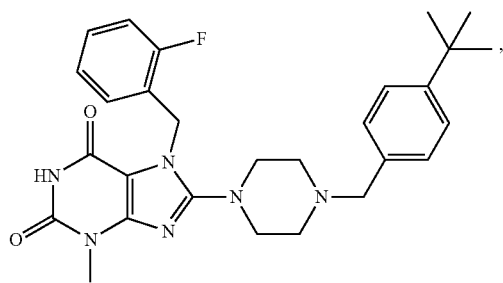 [SMILES: Cn1c(=O)[nH]c(=O)c2c1nc(N1CCN(Cc3ccc(C(C)(C)C)cc3)CC1)n2Cc1ccccc1F ; ","]

or a pharmaceutically acceptable salt thereof.

2. A pharmaceutical composition comprising a therapeutically effective amount of a compound having a structure:

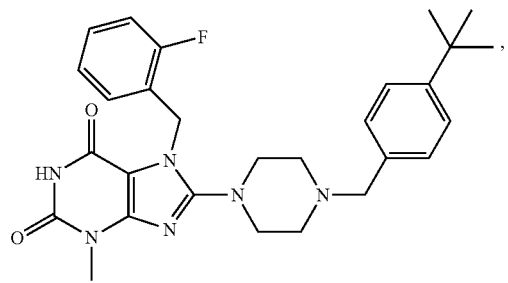 [SMILES: Cn1c(=O)[nH]c(=O)c2c1nc(N1CCN(Cc3ccc(C(C)(C)C)cc3)CC1)n2Cc1ccccc1F ; ","]

or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 11,578,073 B2
APPLICATION NO. : 16/905857
DATED : February 14, 2023
INVENTOR(S) : Ashish Kumar Pathak et al.

Page 1 of 1

It is certified that error appears in the above-identified patent and that said Letters Patent is hereby corrected as shown below:

In the Specification

Column 1, replace Lines 14-17 after the heading "STATEMENT REGARDING FEDERALLY SPONSORED RESEARCH" with the following:
--"This invention was made with government support under AI142759 and U19 AI109680 awarded by the National Institutes of Health. The government has certain rights in the invention."--

Signed and Sealed this
Twenty-sixth Day of August, 2025

Coke Morgan Stewart
*Acting Director of the United States Patent and Trademark Office*